US010620188B2

(12) United States Patent
Abassi et al.

(10) Patent No.: US 10,620,188 B2
(45) Date of Patent: *Apr. 14, 2020

(54) USING IMPEDANCE-BASED CELL RESPONSE PROFILING TO IDENTIFY PUTATIVE INHIBITORS FOR ONCOGENE ADDICTED TARGETS OR PATHWAYS

(71) Applicant: ACEA Biosciences, Inc., San Diego, CA (US)

(72) Inventors: Yama A. Abassi, San Diego, CA (US); Li Zhao, San Diego, CA (US); Ning Ke, San Diego, CA (US); Xiaobo Wang, San Diego, CA (US); Xiao Xu, San Diego, CA (US)

(73) Assignee: ACEA Biosciences, Inc., San Diego, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 15/612,688

(22) Filed: Jun. 2, 2017

(65) Prior Publication Data
US 2017/0269062 A1    Sep. 21, 2017

Related U.S. Application Data

(63) Continuation of application No. 13/403,976, filed on Feb. 23, 2012, which is a continuation-in-part of
(Continued)

(51) Int. Cl.
*C40B 30/04* (2006.01)
*G01N 33/50* (2006.01)
(Continued)

(52) U.S. Cl.
CPC ......... *G01N 33/5014* (2013.01); *C12Q 1/002* (2013.01); *G01N 33/5011* (2013.01);
(Continued)

(58) Field of Classification Search
None
See application file for complete search history.

(56) References Cited

U.S. PATENT DOCUMENTS 2,656,508 A   10/1953   Coulter
3,259,842 A    7/1966   Coulter et al.
(Continued)

FOREIGN PATENT DOCUMENTS

EP   1138758 A1   10/2001
EP   1195432 B1    6/2004
(Continued)

OTHER PUBLICATIONS

Aravanis et al. "A Genetically Engineered Cell-Based Biosensor for Functional Classification of Agents," Biosensors & Bioelectronics, 2001, 16:571-577.
(Continued)

*Primary Examiner* — Christian C Boesen
(74) *Attorney, Agent, or Firm* — Wagenknecht IP Law Group PC

(57) ABSTRACT

Methods of identifying whether a biologically active agent affects an oncogene addicted pathway within a cancer cell, by introducing a biologically active agent suspected of affecting an oncogene addicted pathway to a first well and a negative control to a second well, and introducing a stimulating agent that stimulates the oncogene addicted pathway to both wells; monitoring cell-substrate impedance of the two wells and optionally determining cell indices from impedance values; generating an impedance based curve for each of the two wells from the impedance values or from the cell indices; comparing the impedance-based curves to determine a degree of similarity; and if significantly different concluding the biologically active agent affects the oncogene addicted pathway within the cancer cells.

20 Claims, 42 Drawing Sheets

Related U.S. Application Data application No. 11/198,831, filed on Aug. 4, 2005, now Pat. No. 8,263,375, said application No. 11/198,831 is a continuation-in-part of application No. 11/055,639, filed on Feb. 9, 2005, now Pat. No. 7,560,269, which is a continuation-in-part of application No. 10/987,732, filed on Nov. 12, 2004, now Pat. No. 7,192,752, and a continuation-in-part of application No. 10/705,447, filed on Nov. 10, 2003, now Pat. No. 7,470,533, said application No. 10/987,732 is a continuation-in-part of application No. 10/705,615, filed on Nov. 10, 2003, now Pat. No. 7,459,303, said application No. 11/055,639 is a continuation-in-part of application No. PCT/US2005/004481, filed on Feb. 9, 2005, said application No. 13/403,976 is a continuation-in-part of application No. PCT/US2004/037696, filed on Nov. 12, 2004.

(60) Provisional application No. 61/445,762, filed on Feb. 23, 2011, provisional application No. 60/519,567, filed on Nov. 12, 2003, provisional application No. 60/435,400, filed on Dec. 20, 2002, provisional application No. 60/469,572, filed on May 9, 2003, provisional application No. 60/542,927, filed on Feb. 9, 2004, provisional application No. 60/548,713, filed on Feb. 27, 2004, provisional application No. 60/614,601, filed on Sep. 29, 2004, provisional application No. 60/598,608, filed on Aug. 4, 2004, provisional application No. 60/630,071, filed on Nov. 22, 2004, provisional application No. 60/689,422, filed on Jun. 10, 2005, provisional application No. 60/598,609, filed on Aug. 4, 2004, provisional application No. 60/613,872, filed on Sep. 27, 2004, provisional application No. 60/647,189, filed on Jan. 26, 2005, provisional application No. 60/647,075, filed on Jan. 26, 2005, provisional application No. 60/660,829, filed on Mar. 10, 2005, provisional application No. 60/660,898, filed on Mar. 10, 2005.

(51) Int. Cl.
  *C12Q 1/00* (2006.01)
  *G01N 33/543* (2006.01)

(52) U.S. Cl.
  CPC ..... *G01N 33/5041* (2013.01); *G01N 33/5438* (2013.01); *C40B 30/04* (2013.01); *G01N 2333/4716* (2013.01)

(56) References Cited

U.S. PATENT DOCUMENTS

| | | |
|---|---|---|
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah et al. |
| 5,278,048 A | 1/1994 | Parce et al. |
| 5,284,753 A | 2/1994 | Goodwin |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Mueller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 6/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadler et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Xu et al. |
| 9,709,548 B2 | 7/2017 | Wang et al. |
| 10,012,636 B2 | 7/2018 | Wang et al. |
| 10,067,121 B2 | 9/2018 | Abassi et al. |
| 2002/0032531 A1 | 3/2002 | Mansky et al. |
| 2002/0076690 A1 | 6/2002 | Miles et al. |

(56) References Cited

U.S. PATENT DOCUMENTS

| | | |
|---|---|---|
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2005/0014130 A1 | 1/2005 | Liu et al. |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer et al. |
| 2006/0216203 A1 | 9/2006 | Fuller et al. |
| 2006/0240490 A1 | 10/2006 | Lee |
| 2007/0042347 A1 | 2/2007 | Rosen et al. |
| 2007/0087333 A1 | 4/2007 | Gruters et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2009/0017465 A1 | 1/2009 | Xu et al. |
| 2009/0142790 A1 | 6/2009 | Fang et al. |
| 2009/0241698 A1 | 10/2009 | Biksacky |
| 2010/0029506 A1 | 2/2010 | Wang et al. |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0295253 A1 | 11/2012 | Abassi et al. |
| 2012/0322050 A1 | 12/2012 | Abassi et al. |
| 2013/0123136 A1 | 5/2013 | Abassi et al. |
| 2014/0203818 A1 | 7/2014 | Wang et al. |
| 2015/0125894 A1 | 5/2015 | Laing et al. |
| 2015/0185206 A1 | 7/2015 | Abassi et al. |
| 2015/0231634 A1 | 8/2015 | Szita et al. |
| 2017/0205391 A1 | 7/2017 | Li et al. |
| 2017/0315131 A1 | 11/2017 | Xu et al. |
| 2017/0370907 A1 | 12/2017 | Abassi et al. |
| 2018/0246079 A1 | 8/2018 | Wang et al. |

FOREIGN PATENT DOCUMENTS

| | | |
|---|---|---|
| EP | 1 040 345 B1 | 3/2006 |
| EP | 2213721 A1 | 8/2010 |
| EP | 2291645 | 9/2015 |
| WO | 1996/001836 A1 | 1/1996 |
| WO | 1999/066329 A1 | 12/1999 |
| WO | 2000/37628 A1 | 6/2000 |
| WO | 2000/70343 A2 | 11/2000 |
| WO | 2000/071669 A1 | 11/2000 |
| WO | 2001/025769 A3 | 4/2001 |
| WO | 2001/038873 A3 | 5/2001 |
| WO | 2001/79529 A1 | 10/2001 |
| WO | 2002/004943 A3 | 1/2002 |
| WO | 2002/042766 A3 | 5/2002 |
| WO | 2003/016887 A3 | 2/2003 |
| WO | 2004/010103 A2 | 1/2004 |
| WO | 2005/005979 A1 | 1/2005 |
| WO | 2005/047482 A2 | 5/2005 |
| WO | 2005/077104 A2 | 8/2005 |
| WO | 2006/017762 A2 | 2/2006 |
| WO | 2009/137440 A1 | 11/2009 |
| WO | 2010/129725 A1 | 11/2010 |
| WO | 2011/146531 A1 | 11/2011 |
| WO | 2012/043820 A1 | 4/2012 |
| WO | 2014/085727 A1 | 6/2014 |
| WO | 2017/068421 A1 | 4/2017 |
| WO | 2017/087945 A1 | 5/2017 |

OTHER PUBLICATIONS

Baumann et al. "Microeletronic Sensor System for Microphysiological Application on Living Cells," Sensors & Accuators, 1999, B55:77-89.

Becker et al. "Separation of Human Breast Cancer Cells from Blood by Differential Dielectric Affinity," Cell Biology, 1995, 92:960-964.

Berens et al. "The Role of Extracellular Matrix in Human Astrocytoma Migration and Proliferation Studied in a Microliter Scale Assay," Clinical & Experimental Metastasis, 1994, 12(6)405-415.

Bergveld, P."A Critical Evaluation of Direct Electrical Protein Detection Methods," Biosensors & Bioelectronics, 1991, 6:55-72.

Bierberich et al. "Neuronal Differentiation and Synapse Formation of PC12 and Embryonic Stem Cells on Interdigitated Microelectrode Arrays Contact Structures for Neuron-to-Electrode Signal Transmission (NEST)," Biosensors and Bioelectronics, 2004,19:923-931.

Burnett et al. "Fluoresence Imaging of Electrically Stimulated Cells," Journal of Biomolecular Screening, 2003, 8(6)660-667.

Burns et al. "Neutrophil Transendothelial Migration is Independent of Tight Junctions and Occurs Preferentially at Tricellular Corners," Journal of Immunology, 1997, 2893-2903.

Ciambrone et al. "Cellular Dielectric Spectroscopy: A Powerful New Approach to Label-Free Cellular Analysis," Journal of Biomolecular Screening, 2004, 9(6)467-480.

Connolly et al. "An Extracellular Microelectrode Array for Monitoring Electrogenic Cells in Culture," Biosensors & Bioelectronics, 1999, 5:223-234.

Duan et al. "Separation-Free Sandwich Enzyme Immunoassays Using Microporous Gold Electrodes and Self-Assembled Monolayer/Immobilized Capture Antibodies," Analytical Chemistry, 1994, 66(9)1369-1377.

Ehret et al. "Monitoring of Cellular Behaviour by Impedance Measurements on Interdigitated Electrode Structures," Biosensors & Bioelectronics, 1997, 12(1)29-41.

Ehret et al. "On-Line Control of Cellular Adhesion with Impedance Measurements Using Interdigitated Electrode Structures," Medical & Biological Engineering & Computing, 1998, 36:365-370.

Falk et al. "A 48-Well Micro Chemotaxis Assembly for Rapid and Accurate Measurement of Leukacyte Migration," Journal of Immunological Methods, 1980, 33:239-247.

Fuhr et al. "Positioning and Manipulation of Cells and Microparticles Using Miniaturized Electric Field Traps and Travelling Waves," 1995, Sensors & Materials, 7(2)131-146.

Gaiever et al. "Monitoring Fibroblast Behavior in Tissue Culture with an Applied Electric Field," Proc. Natl. Acad. Sci. USA, 1984, 81:3761-3764.

Gaiever et al. "Micromotion of Mamalian Cells Measured Electrically," Proc. Natl. Acad. Sci. USA, 1991, 88:7896-7900.

Gutmann et al. "Evidence for Different ABC-Transporters in Caco-2 Cells Modulating Drug Uptake," Pharmaceutical Research, 1999, 16(3)402-407.

Hadjout et al. "Automated Real-Time Measurement of Chemotactic Cell Motility," Biotechniques, 2001, 31:1130-1138.

Henning et al. "Approach to a Multiparametric Sensor-Chip-Based Tumor Chemosensitivity Assay," Anti-Cancer Drugs, 2001, 12:21-32.

Hidalgo et al. "Characterization of the Human Colon Carcinoma Cell Line (Caco-2) as a Model System for Intestinal Epithelial Permeability," Gastroenterology, 1989, 96:736-749.

Huang et al. "Dielectrophoretic Cell Separation and Gene Expression Profiling on Microelectronic Chip Arrays," Analytical Chemistry, Jul. 15, 2002, 74(14)3362-3371.

Hug, Thomas S. "Biophysical Methods for Monitoring Cell-Substrate Interactions in Drug Discovery," Assay and Drug Devevelopment Technologies, Nov. 3, 2003, 1(3)479-488.

Keese et al. "Real-Time Impedance Assay to Follow the Invasive Activities of Metastatic Cells in Culture," Biotechniques, 2002, 33:842-850.

(56) References Cited

OTHER PUBLICATIONS

Kleinman et al. "Basement Membrane Complexes With Biological Activity," Biochemistry, 1986, 26:312-318.
Kowolenko et al. "Measurement of Macrophage Adherence and Spreading with Weak Electric Fields," Journal of Immunological Methods, 1990, 127:71-77.
Larsen et al. "Somatic Cell Counting with Silicon Apertures," Micro Total Analysis Systems, 2000, 103-106.
Wang et al. "Electronic Manipulation of Cells on Microchip-Based Devices," Biochip Technology, 2001, pp. 135-159, Harwood Academic Publishers, Philadelphia, PA, USA.
"Neuro Probe AA96, AB96, AC96 Chemotaxis Chambers," Neuro Probe, [retrieved from the internet] http://www.neuroprobe.com/protocol/pt_96a.html, 5 pgs.
"Detect Cell Migration and Invasion in a Homogeneous Fluorescent Assay System," BD Biosciences, [retrieved from the internet] http://www.bdbiosciences.com/discovery_labware/Products/inserts/BD_Falcon_HTS_fluoroblok_inserts/individual_fluoroblok_inserts/index.html, 2004.
"Cell Migration Studies with TECAN Systems," TECAN, Sep. 1999, [retrieved from the internet] http://www.tecan.com/migration_introl.pdf, 10 pgs.
"Automated Cell Monitoring Instrument," Applied BioPhysics, 2002, [retrieved from the internet] http://www.biophysics.com/pages/front.html, 1 page.
Wegener et al. "Electric Cell-Substrate Impedance Sensing System (ECIS) as a Noninvasive Means to Monitor the Kinetics of Cell Spreading to Artificial Surfaces," Experimental Cell Research, 2000, 259:158-166.
Banach et al. "Development of Electrical Activity in Cardiac Myocyte Aggregates Derived from Mouse Embryonic Stem Cells," Am J Physiol Heart Circ Physiol, 2003, 284: H2114-H2123.
Hescheler et al. "Determination of Electrical Properties of ES Cell-derived Cardiomyocytes Using MEAs," Journal of Electrocardiology, 2004, vol. 37, Suppl.
Horvath et al. "Monitoring of Living Cell Attachment and Spreading Using Reverse Symmetry Waveguide Sensing," Applied Physics Letters, 2005, 86:071101.
Neher, Erwin. "Molecular Biology Meets Microelectronics," Nature Biotechnology, 2001, 19:114.
Oka et al. "A New Planar Multielectrode Array for Extracellular Recording: Application to Hippocampal Acute Slice," Journal of Neurosciences Methods, 1999, 93(1)61-67, Elsevier Science, B.V.
Slaughter et al. "Artificial Neural Network for Temporal Impedance Recognition of Neurotoxins," 2006 International Joint Conference on Neural Networks, Jul. 16-21, 2006, 2001-2008.
Klauke et al. "Extracellular Recordings of Field Potentials from Single Cardiomyocytes," Biophysical Journal, Oct. 2006, 91:2543-2551.
Lo et al. "Abstract C1.00268: Effect of cMet Inhibitor on HGF-Induced Ovarian Carcinoma Cell Migration," American Physical Societal March Meeting, 2010, Portland Oregon, vol. 55, poster session.
Lin et al. "Electroporation Microchips for In Vitro Gene Transfection," Journal of Micromechanics and Microengineering, 2011, 11:542-547.
Lin et al. "Simulation and Experimental Demonstration of the Electric Field Assisted Electroporation Microchip for In Vitro Gene Delivery," Miniaturisation for Chemistry, Biology & Bioengineering, 2004, 4:104-108.
Lo et al. "Monitoring Motion of Confluent Cells in Tissue Culture," Experimental Cell Research, 1993, 204:102-109.
Lo et al. "pH change in Pulsed CO2 Incubators Cause Periodic Changes in Cell Morphology," Experimental Cell Research, 1994, 213:391-397.
Lo et al. "Impedance Analysis of MDCK Cells Measured by Electric Cell-Substrate Impedance Sensing," Biophysical Journal, 1995, 69:2800-2807.
Loffert et al. "Multiplex PCR with Qiagen," QiagenNews, 1997, 4:15-18.
Luong et al. "Monitoring Motility, Spreading, and Mortality of Adherent Insect Cells Using Impedance Sensor," Analytical Chemistry, Apr. 15, 2001, 73(8)1844-1848.
Mitra et al. "Electric Measurements Can Be Used to Monitor the Attachment and Spreading of Cells in Tissue Culture," Biotechniques, 1991, 11(4)504-510.
Miyata et al. "New Wound-Healing Model Using Cultured Corneal Endothelial Cells," Japanese Journal of Opthalmology, 1990 34:257-266.
Nerurkar et al. "The Use of Surfactants to Enhance the Permeability of Peptides Through Caco-2 Cells by Inhibition of an Apically Polarized Efflux System," Pharmaceutical Research, 1996, 13(4)528-534.
Ong et al. "Remote Query Resonant-Circuit Sensors for Monitoring of Bacteria Growth," Sensors, 2002, 2:219-222.
Pancrazio et al. "Portable Cell-Based Biosensor System for Toxin Detection," Sensors and Actuators, 1998, 853:179-185.
Patolsky et al. "Detection of Single Based DNA Mutations by Enzyme-Amplified Electronic Transduction," Nature Biotechnology, 2001, 19:253-257.
Bethig et al. "Positive and Negative Dielectrophoretic Collection of Colloidal Particles Using Interdigitated Castellated Microelectrodes," Appl Phys, 1992, 24:881-888.
Richards et al. "A Modified Microchamber Method for Chemotaxis and Chemokinesis," Immunological Communications, 1984, 13(1)49-62.
Rishpon et al. "An Amperometric Enzyme-Channeling Immunosensor," Biosensors & Bioelectronics, 1997, 12(3)195-204.
Simpson et al. "Whole-Cell Biocomputing," Trends in Biotechnology, 2001, 19:317-323.
Sohn et al. "Capacitance Cytometry: Measuring Biological Cells One by One," Proc. Nat. Acad. Sci., 2001, 97(20)10687-10690.
Stenger et al. "Detection of Physiologically Active Compounds Using Cell-Based Biosensors," Trends in Biotechnology, 2001, 19:304-309.
Svetlicic et al. "Charge Displacement by Adhesion and Spreading of a Cell," Bioelectrochemistry, 2000, 53:79-86.
Tiruppathi et al. "Electrical Method for Detection of Endothelial Cell Shape Change in time: Assessment of Endothelial Barrier Function," Proc. Natl. Acad. Sci. USA, 1992, 89:7919-7923.
Wang et al. "Cell Separation by Dielectrophoretic Field-Flow-Fractionation," Analytical Chemistry, 2000, 72:832-839.
Wang et al. "Selective Dielectrophoretic Confinement of Bioparticles in Potential Energy Wells," Applied Physics, 1993, 26:1278-1285.
Nang et al. "Dielectrophoretic Manipulation of Cells Using Spiral Electrodes," Biophysical Journal, 1997, 72:1887-1899.
Wang et al. "A Theoretical Method of Electrical Field Analysis for Dielectrophoretic Electrode Arrays Using Green's Theorem," Applied Physics, 1996, 30:1649-1660.
Wang et al. Separation of Polystyrene Microbeads Using Dielectrophoretic Gravitational Field-Flow-Fractionation, Biophysical Journal, 1998, 74:2689-2701.
EP05786773 European Extended Search Report dated Mar. 21, 2013.
Warburg, "Ueber die Polarisationscapacitat des Platins," Ann. Phys., 1901, 6:125-135.
Wegener et al. "Use of Electrochemical Impedance Measurements to Monitor Beta-Adrenergic Stimulation of Bovine Aortic Endothelial Cells," European Journal of Physiology, 1999, 437:925-934.
Wolf et al. "Monitoring of Cellular Signalling and Metabolism with Modular-Sensor Technique," Biosensors and Bioelectronics, 1998, 13:501-509.
Xiao et al. "On-line Monitoring of Cell Growth and Cytotoxicity Using Electric Cell-Substrate Impedance Sensing (ECIS)," Biotechnol. Prog, 2003, 19(3)1000-1005.
Xiao et al. "An In-Depth Analysis of Electric Cell-Substrate Impedance Sensing to Study the Attachment and Spreading of Mammalian Cells," Analytical Chemistry, 2002, 74:1333-1339.
Xiao et al. "Assessment of Cytotoxicity Using Electric Cell-Substrate Impedance Sensing," Analytical Chemistry, 2002, 74:5748-5753.

(56) References Cited

OTHER PUBLICATIONS

Yamauchi et al. "Spatially and Temporally Controlled Gene Transfer by Eletrcoporation into Adherent Cells on Plasma DNA-Loaded Eletrodes," Nucleic Acids Research, 2004, 32(22)1-8.
Yang et al. "Cell Separation on Microfabricated Electrodes Using Dielectrophoretic/Gravitational Field-Flow-Fractionation," Analytical Chemistry, 1999, 71:911-918.
Mohr et al. "Performance of a Thin Film Microelectrode Array for Monitoring Electrogenic Cells In Vitro," Sensors and Actuators, 1996, B34:265-269.
Cady et al. "Electrical Impedance Measurements: Rapid Method for Detecting and Monitoring Microorganisms," Journal of Clinical Microbiology, 1978, 7(3)265-272.
"Molecular Viewer," New Products page, Dec. 20, 2002, Science 298:2409.
Berdondini et al. "High-Density Electrode Array for Imaging In Vitro Electrophysiological Activity," Biosensors and Bioelectronics, 2005, 21:167-174.
Chang et al. "Impedimetric Monitoring of Cell Attachment on Interdigitated Microelectrodes," Sensors and Actuators, 2005, B 105:159-163.
Yang et al. "A novel Microfluidic Impedance Assay for Monitoring Endothelin-Induced Cardiomyocyte Hypertrophy," Biosensors and Bioelectronics, 2007, 22:1688-1693.
PCT/US2009/033801 International Search Report and Written Opinion dated Jul. 9, 2010.
PCT/US2009/042787 International Search Report and Written Opinion dated Jun. 24, 2009.
PCT/US2011/036877 International Search Report dated Sep. 2, 2011.
PCT/US2013/072439 International Search Report dated Feb. 19, 2014.
PCT/US2005/034561 International Preliminary Report on Patentability dated Mar. 27, 2007.
PCT/US2005/034561 International Search Report dated Sep. 27, 2006.
PCT/US2005/027943 International Preliminary Report on Patentability dated Apr. 11, 2007.
PCT/US2005/027943 International Search Report and Written Opinion dated Mar. 21, 2007.
PCT/US2004/037696 International Search Report dated May 16, 2005.
PCT/US2005/04481 International Search Report dated Sep. 12, 2005.
EP05722991 Extended European Search Report dated Apr. 3, 2009.
EP11193882 Extended European Search Report dated Apr. 5, 2012.
EP13171137 Extended European Search Report dated Aug. 16, 2013.
EP05786773 Extended European Search Report dated Mar. 21, 2013.
EP05852157 Extended European Search Report dated Sep. 13, 2011.
EP058122680 Extended European Search Report dated Sep. 7, 2011.
EP03748948 Extended European Search Report dated Mar. 12, 2007.
CA2556219 Office Action dated Aug. 9, 2010.
CA2575573 Office Action dated Apr. 4, 2012.
EP09743420 European Search Report dated Nov. 26, 2013.
Kloss et al. "Microcavity Array (MCA)-Based Biosensor Chip for Functional Drug Screening of 3D Tissue Models" Biosensors and Bioelectronics, 2008, 23:1473-1480.
Steinem et al. "Impedance and Shear Wave Resonance Analysis of Ligand-Receptor Interactions at Functionalized Surfaces and of Cell Monolayers," Biosensors & Bioelectronics, 1997, 12(8)787-808.
Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.
Yu et al. "Real-Time Monitoring of Morphological Changes in Living Cells by Electronic Cell Sensor Arrays: An Approach to Study G Protein-Coupled Receptors," Analytical Chemistry, 2006, 78:35-43.
Xing et al. "Dynamic Monitoring of Cytotoxicity on Microelectronic Sensors" Chemical Resarch in Toxicology, 2005, 18(2)154-161.
Blagbrough et al. "Polyamines and Novel Polyamine Conjugates Interact with DNA in Ways That Can be Exploited in Non-Viral Gene Therapy," Biochemical Society Transactions, 2003, 31(2)397-406.
Bonetta, Laura, "The Inside Scoop—Evaluating Gene Delivery Methods," Nature Methods, Nov. 2005, 2(11) 875-883.
Hapala, Ivan, "Breaking the Barrier: Methods for Reversible Permeabilization of Cellular Membranes," Critical Reviews in Biotechnology, 1997, 17(2)105-122.
Luan et al. "Clustering of Time-Course Gene Expression Data Using a Mixed-Effects Model with B-Splines," Bioinformatics, 2003, 19(4)474-482.
Nicolazzi et al. "Cationic Lipids for Transfection," Current Medicinal Chemistry, 2003, 10:1263-1277.
Rabow et al. "Mining the National Cancer Institute's Tumor-Screening Database: Identification of Compounds with Similar Cellular Activities," Journal of Medicinal Chemistry, 2002, 45(4)818-840.
HP 4284A Precision LCR Meter Operation Manual, Aug. 1998, Hewlett Packard, 6th Edition, p. 1-460.
EP10772804.0 Extended European Search Report dated Oct. 27, 2017.
PCT/US2016/063066 ISR and WO dated Jan. 30, 2017.
PCT/US2018/044774 ISR and WO dated Oct. 23, 2018.
Fusenig et al. "The Need for a Worldwide Consensus for Cell Line Authentication: Experience Impletementing a Mandatory Requirement at the International Journal of Cancer". PLOS Biology, Apr. 17, 2017, 15(4) p. e2001438 pp. 1-13.

A

B

USING IMPEDANCE-BASED CELL RESPONSE PROFILING TO IDENTIFY PUTATIVE INHIBITORS FOR ONCOGENE ADDICTED TARGETS OR PATHWAYS

CROSS REFERENCE TO RELATED APPLICATIONS

This is continuation of U.S. patent application Ser. No. 13/403,976, filed Feb. 23, 2012, which claims priority to U.S. provisional patent application 61/445,762 filed Feb. 23, 2011.

U.S. patent application Ser. No. 13/403,976 is also a continuation in part of U.S. patent application Ser. No. 11/198,831, filed Aug. 4, 2005, now U.S. Pat. No. 8,263,375, which is a continuation-in-part of U.S. patent application Ser. No. 11/055,639, filed Feb. 9, 2005, now U.S. Pat. No. 7,560,269, which is a continuation-in-part of U.S. patent application Ser. No. 10/987,732, filed Nov. 12, 2004, now U.S. Pat. No. 7,192,752, which claims priority to U.S. provisional patent application 60/519,567, filed Nov. 12, 2003. U.S. patent application Ser. No. 13/403,796 is also a continuation-in-part of PCT patent application PCT/US04/37696, filed Nov. 12, 2004. All of the applications referred to in this paragraph are incorporated by reference in their entireties herein.

U.S. patent application Ser. No. 10/987,732 is itself a continuation-in-part of U.S. patent application Ser. No. 10/705,447, filed Nov. 10, 2003, now U.S. Pat. No. 7,470,533, which claims priority to U.S. provisional patent application 60/435,400, filed Dec. 20, 2002; and U.S. provisional patent application 60/469,572, filed May 9, 2003. All of the applications referred to in this paragraph are incorporated by reference in their entireties herein.

U.S. patent application Ser. No. 10/987,732 is also a continuation-in-part of U.S. patent application Ser. No. 10/705,615, filed Nov. 10, 2003, now U.S. Pat. No. 7,459,303, which claims priority to U.S. provisional patent application 60/435,400, filed Dec. 20, 2002; and U.S. provisional patent application 60/469,572, filed May 9, 2003. All of the applications referred to in this paragraph are incorporated by reference in their entireties herein.

U.S. patent application Ser. No. 11/055,639, also claims priority to U.S. provisional patent application 60/542,927 filed Feb. 9, 2004; U.S. provisional patent application 60/548,713, filed Feb. 27, 2004, and U.S. provisional patent application 60/614,601, filed Sep. 29, 2004. All of the applications referred to in this paragraph are incorporated by reference in their entireties herein.

U.S. patent application Ser. No. 11/198,831 is a continuation-in-part of PCT patent application PCT/US05/04481, filed Feb. 9, 2005. U.S. patent application Ser. No. 11/198,831 also claims benefit of priority to U.S. provisional patent application 60/598,608, filed Aug. 4, 2004, U.S. provisional patent application 60/630,071, filed Nov. 22, 2004, U.S. provisional patent application 60/689,422, filed Jun. 10, 2005, U.S. provisional patent application 60/598,609, filed Aug. 4, 2004, U.S. provisional patent application 60/613,872, filed Sep. 27, 2004, U.S. provisional patent application 60/647,189, filed Jan. 26, 2005, U.S. provisional patent application 60/647,075, filed Jan. 26, 2005, U.S. provisional patent application 60/660,829, filed Mar. 10, 2005, and U.S. provisional patent application 60/660,898 filed on Mar. 10, 2005. All of the applications referred to in this paragraph are incorporated by reference in their entireties herein.

TECHNICAL FIELD

This invention relates to the field of cell-based assays. In particular, the invention provides methods to screen and identify putative inhibitors for oncogenes and their signal pathways using impedance-based devices.

BACKGROUND OF THE INVENTION

Understanding the transformation of a normal cell to cancerous cell continues to be a very active area of research both for delineating the underlying molecular mechanisms involved in both genesis and maintenance of cancer as well as developing therapies which may help prevent or manage cancerous growth. While the precise molecular mechanisms leading to emergence of cancer is still being revealed, it is generally agreed that a handful of key genes which serve to regulate growth, proliferation, survival, migration and demise of cells are involved. These genes are typically of two broad classes referred to as either oncogenes or tumor suppressor genes. Both classes of genes under normal circumstances play key roles in regulating cellular processes mentioned above. However, due to certain mutations or over expression these genes are either constitutively activated (as in the case of kinases) or inactivated in the case of tumor suppressor genes such as PTEN.

While the general consensus has been that cancer is typically the result of multiple lesions that act in concert to maintain and support cancerous growth and metastasis, work over the last decade is providing evidence that at least certain kinds of cancers may depend on only a single oncogene or oncogenic pathway for growth, proliferation and survival. This hypothesis is referred to as oncogene addiction and as a corollary to this hypothesis it can be postulated targeting these key oncogenes for drug development may provide a window of opportunity for cancer treatment. Thus oncogne addiction may present the "Achilles' heel" of cancer which may be exploited therapeutically. A profound implication of this hypothesis is that switching off this crucial pathway upon which cancer cells have become dependent should have devastating effects on the cancer cell while sparing normal cells that are not similarly addicted.

Tumor dependency on the well-studied "classical" oncogenes, such as transcription factor MYC and GTPase RAS, has been demonstrated in variety of experimental models (Felsher and Bishop 1999; Wu et al. 2007; Chin et al. 1999; Fisher et al 2001).

Activated kinases have been shown to be the "Achilles' heel" of many cancers (Sharma S. V. and Settleman J. Genes Dev. 2007 21:3214-3231). A kinase is a type of enzyme that transfer phosphate groups from high-energy donor molecules, such as ATP, to specific substrates, a process referred to as phosphorylation. One of the largest groups of kinases are protein kinases, which act on and modify the activity of specific proteins. More than 500 different protein kinases have been identified in human; of this 11% are known to be receptor tyrosine kinases (RTKs). Various other kinase act on small molecules such as lipids, carbohydrates, amino acids and nucleotides, either for signaling or prime them for metabolic pathway. In addition to the functions in normal tissues/organs, many kinses also play more specialized roles in a host of human diseases including cancer. A subset of kinases (also referred to as oncogenic kinases), when dysregulated, can cause tumor formation/growth and further contribute to tumor maintenance and progression. Thus, oncogenic kinases represent one of the largest and most attractive groups of targets for cancer intervention and drug development.

ABL and platelet-derived growth factor receptor (PDGFR) tyrosine kinase, which are targets of imatinib, are often activated by chromosomal translocations (BCR-ABL, TEL-ABL, TEL-PDGFR). Tumor cell lines harboring these activated ABL and PDGFR become addicted to them for their survival and undergo apoptosis following inactivation of these two concogenes. The clinical success of imatinib in treating chronic myelogenous leukemia (CML) and gastrointestinal stromal tumor (GIST) is the first examples of oncogene addiction in the context of cancer therapy. Imatinib, which also inhibits the KIT receptor tyrosine kinase, cause apoptosis of small cell lung cancer (SCLC) cell lines addicted to the autocrine loop created by the expression of KIT as well as its ligand, stem cell factor in these cells in culture or xenografts. Additionally, mutations in KIT in GIST renders these cells addicted to the KIT oncoprotein, and its inactivation leads to apoptosis of the tumor cells.

Oncogene addiction also contributes to the clinal success of agents that target HER2. The HER2 oncogene is amplified in 25-30% of breast cancers, suggesting that these tumors may be addicated to HER2. Consistent with this hypothesis, breast cancer cells in culture or grown as xenografts are preferentially growth inhibited by HER2 inhibition. These finding led to the clinical success of HER2 targeted antibodies, Trastuzumab/Herceptin and Pertuzumab in treatment of patients with HER2-positive metastatic breast cancer.

The use of selective epidermal growth factor receptor (EGFR) kinase inhibitors in lung cancer treatment presents another example of onocogene addiction that has yielded clinical success. Mutations of the kinase domain of EGFR are found in a 10-20% non-small cell lung cancer (NSCLC), and significant clinical responses to EGFR inhibitors (gefitinib and erlotinib) have been well correlated to such mutations. Glioblastomas harboring EGFR gene amplification and deletion mutations appear to be addicted to these EGFR activating mutations.

The use of mutant specific b-Raf (V600E) inhibitor (Vemurafenib/PLX4032) in treatment of late-stage melanoma presents another example of onocogene addiction that has yielded clinical success. About 60% of melanomas have V600E mutation. PLX4032 has been shown to cause apoptosis in these melanoma cell lines (Hatzivassiliou, et al. Nature 2010 464:431-5). And the growth of a melanoma cell line A375 has been shown to be inhibited by silencing the bRAF gene by short hairpin RNA (Sala, et al. Mol. Cancer Res. 2008 6:751-9).

The use of ALK kinase inhibitor in NSLC treatment is another clinical success utilizing oncogene addiction concept. About 4% of patients with NSCLC have a chromosomal rearrangement that generates a fusion gene between EML4 (echinoderm microtubule-associated protein-like 4) and ALK (anaplastic Lymphoma kinase) and about 60% of Anaplastic Large Cell Lymphomas (ALCL) have a chromosomal translocation that results a fusion gene between NPM (nucloplasmin) and ALK. Both fusions result in constitutive kinase activity that contributes to carcinogenesis and seems to drive the malignant phenotype. ALK mutations are also thought to be important in driving the malignant phenotype in about 15% of cases of neuroblastoma, a rare form of central neverous system cancer that occurs almost exclusively in very young children. Crizotinib/PF02341066 has successfully shown to cause tumor shrinkage or stabilizing disease in 90% of patients carrying the ALK fusion gene (Hem Onc Today 2010-06-05).

In addition to the clinical successes of a few kinase inhibitors to which tumor cells have become addicted, more clinical data indicates that this phenomenon may be apply to a large number of other kinases. For examples, MET gene amplifications, as well mutations and abnormal expression of the MET signaling pathway have been observed in a significant fraction of gastric cancers, lung cancers and prostate cancers. The fibroblast growth factor receptor 3 (FGFR3) is activated in 15% of multiple myelomas by chromosomal translocation. Aurora kinases are frequently amplified in a diverse array of human cancers such as leukemia, colon and pancreatic tumors. Genetic aberrations of PI3K, which lead to constitutive activation, are commonly observed in human cancers (Bader et al. Nature Review 2005 5: 921-9). Lastly, the RET oncogene is frequently mutated in medullary thyroid carcinomas and subset of papillary thyroid cancers. It has been shown that inactivation of these mutated kinase by a variety of methods in different systems typically results in growth inhibition of tumor cell death.

Recent studies have shown that additional classes of genes that may also confer a state of dependency in cancer when dysregulated. For example, oncogenic RNAs ("oncomirs") have emerged as important players in cancer. The role of oncomirs in oncogene addition is demonstrated by the fact that antisense inhibition of these oncomirs led to apoptosis of lunger cancer cells overexpressing the corresponding oncomirs (Matsubara et al. Oncogene 2007 26: 6099-6105.)

In order to develop therapies for targeting key oncogenes involved in cancer, it is important to establish both in vitro and in vivo models that can be used for screening and evaluation of lead compounds. One of the advantages for developing in vitro oncogene addiction models is that certain cancer cell lines continue to maintain the oncogene addiction state even when cultured in petri-dishes or microtiter plates. The oncogene addiction status of these cell lines can be evaluated by using tool compounds or other reagents which inhibit the oncogene and typically results in cytostasis or apoptosis. Various molecular biological or cellular biological methods could be used to assay or evaluate the response of these oncogene addicted cells to various tool compounds or other reagents.

SUMMARY OF THE INVENTION

Using impedance-based cell response profiling approach, we have determined that inhibition of key oncogenes in oncogene addicted cell lines leads to generation of unique time-dependent cellular profiles (TCRPs). These TCRPs are dependent on the cell line and the oncogene to which the cell line is addicted to. Thus we have developed methods for exploiting these TCRPs for screening purposes using our proprietary impedance-based platform technology in conjunction with compound libraries to identify small molecule inhibitors which may target oncogenes or oncogne pathways for addiction.

Alternatively, the oncogene of interest can be overexpressed or isogenically expressed in certain cell lines to mimic the oncogene addicted state. In this regard using impedance based TCRP approach can allow for identification of unique signatures which is generated only when treated with unique inhibitors of the oncogene of interest. This signature can be compared to normal expression of the wildtype form of the oncogene (in normal cells or a cell line) referred to as protooncogene to specifically identify TCRPs unique to the oncogene.

Both of the approaches described above, either using oncogene addicted cell lines, isogenic cell lines expressing oncogenes at levels similar to those in natural cancer cells, or certain cell lines overexpressing oncogenes recombinantly and treating with specific tool compounds and reagents and identifying unique TCRPs hold the promise of identifying unique small molecule inhibitors or other type of inhibitors that can potentially be used for cancer drug development.

The present invention provides methods for time-dependent cell response profiling (TCRP) of oncogene addicted cell lines for identification of small molecule inhibitors of oncogenes or oncogene addicted pathways. The methods of the present invention include real-time impedance monitoring of cellular responses of oncogene addicted cells, cell lines or oncogene overexpressing cells or cell lines to biologically active agents and comparing the responses to non-oncogene addicted cells or non-oncogene overexpressing cells, respectively.

The impedance-based system of the present invention provides numerous benefits over the currently used techniques. First, the signature activity profiles are derived from a single well without any extensive manipulations such as washing, fixation, lysing and staining. Second, impedance measurements are based on the inherent cellular response to compounds such as modulation of cell viability, morphology and or adhesion, and therefore preclude the need for engineering the cell with reporter proteins such as GFP or luciferase. Thirdly, impedance-based technology can monitor both short and long term responses and therefore capture the entire cellular response to a specific modulation of oncogene activated pathways and provide a signature response for modulation of the oncogene or oncogene pathway. This is a key difference between impedance-based technology and other standard techniques which do not distinguish between the temporal modulation of oncogene pathways or other pathways but instead rely on endpoint assays. Indeed, the present invention includes using either oncogene addicted cells, isogenic cell lines expressing oncogenes at levels similar to those in natural cancer cells, or certain cell lines overexpressing oncogenes recombinantly and monitoring TCRP to biologically active agents and comparing them with either non-oncogene addicted cells or cells which do not overexpress oncogenes.

In one aspect of the present invention a method of generating a TCRP for the modulation of oncogene addicted cells using a known biologically active agent, which targets the oncogene. The method includes determining the impedance-based TCRP for oncogene-addicted cells in response to the known biologically active agent relative to vehicle control, determining the impedance-based TCRP for non-oncogene-addicted cells in response to the known biologically active agent relative to vehicle control, and comparing the impedance-based TCRP for oncogene addicted cells and non-oncogene-addicted cells in response to the known biologically active agent relative to their corresponding vehicle controls, and if significantly different, categorizing the TCRP of the oncogene addicted cells in response to the known biologically active agent as signature profile for inhibition of oncogene or oncogene addicted pathway.

In one embodiment the method includes, providing a system for monitoring cell-substrate impedance comprising a plurality of impedance monitoring wells; adding oncogene addicted cells comprising an active oncogene addicted pathway to at least two wells and adding non-oncogene addicted cells that lack the active oncogene addicted pathway to at least two other wells; monitoring impedance of the at least four wells over a period of time to obtain impedance values and optionally determining cell indices from the impedance values; introducing at least one known biologically active agent known to affect the oncogene addicted pathway to at least one well having the oncogene addicted cells and to at least one well having the non-oncogene addicted cells, and introducing a vehicle control to another well having the oncogene addicted cells and to another well having the non-oncogene addicted cells, wherein the introductions occur after at least one impedance value for the corresponding well is obtained; generating an impedance-based curve from the impedance values or from the cell indices for each of the at least four wells; comparing the impedance-based curves between wells having the oncogene addicted cells to determine a time dependent cellular response profile (TCRP) in oncogene addicted cells, and comparing the impedance based curves between the non-oncogene-addicted cells to determine a time dependent cellular response profile (TCRP) in non-oncogene addicted cells; and comparing the time dependent cellular response profiles (TCRPs) between oncogene addicted cells and non-oncogene addicted cells; and if significantly different, categorizing the time dependent cellular response profile (TCRP) in oncogene addicted cells as a signature time dependent cellular profile (TCRP) characterized as modulating an oncogene addicted pathway.

A variety of oncogene addicted cells may be used with the methods, including those selected from the group consisting of a cancer cell, optionally a lung cancer cell, a gastric cancer cell, a melanoma cell, an epidermoid cell, a colon cancer cell, a neuroblastoma cell, and a virus infected cell. Oncogene addicted cells can be those that overexpress an oncogene in an oncogene addicted pathway or can be isogenic cells that express an oncogene at a level similar to that of a natural cancer cell.

While the modulation of a variety of oncogene addicted pathways can be monitored, and distinguished from one another among these include a cMET pathway, an EGFR pathway, a PDGFR pathway, an ALK pathway, a P13K pathway, a serine/threonine kinase pathway, and a b-Raf pathway. As such, the methods are particularly useful when the at least one known biologically active agent is an inhibitor of a kinase selected from the group consisting of cMET, EGFR, PDGFR, ALK, P13K, a serine/threonine kinase, and b-Raf. Further analysis of the oncogene addicted pathway can be achieved when the at least one known biologically active agent is provided in different concentrations to a same cell type in different wells to generate a dose response curve, to determine an EC50, or determine an IC50.

While the method can obtain a plurality of single TCRPs, when the at least one biologically agent includes a multitude of biologically active agents a library of signature time dependent response profiles (TCRPs) can be produced, which may be used for subsequent screening of an unknown agent or pathway. To this end the method can further include comparing the signature TCRPs between the multitude of biologically active agents to identify a library of unique signature TCRPs.

In another embodiment, a method of identifying whether a biological agent affects an oncogene addicted pathway is provided, which includes providing a system for monitoring cell-substrate impedance comprising a plurality of impedance monitoring wells; adding oncogene addicted cells comprising an active oncogene addicted pathway to at least two wells; monitoring impedance of the at least two wells over a time period to obtain impedance values and optionally determining cell indices from the impedance values; introducing an unknown biologically active agent which is suspected of affecting the oncogene addicted pathway to one well and introducing a vehicle control to another well, wherein the introductions occur after at least one impedance value for the corresponding well is obtained; generating impedance-based curves from the impedance values or cell indicies from each well; comparing the impedance-based curves between the unknown biologically active agent and vehicle control, and if sufficiently similar, comparing the impedance base curve of the unknown biologically active agent to a library of signature time dependent response profiles (TCRPs) obtained from a multitude of known biologically active agents optionally obtained by the method as set forth above; and if sufficiently similar, identifying the unknown biologically active agent as affecting a same oncogene addicted pathway similarly as the corresponding known biologically active agent; or if not sufficiently similar, catagorzing the unknown biologically active agent as a new signature time dependent response profile (TCRP) in the library.

In another aspect of the invention a method of identifying whether a biological agent affects an oncogene addicted pathway is provided, which includes: providing a system for monitoring cell-substrate impedance comprising a plurality of impedance monitoring wells; adding oncogene addicted cells comprising an active oncogene addicted pathway to at least two wells; monitoring impedance of the at least two wells over a time period to obtain impedance values and optionally determining cell indices from the impedance values; introducing at least one known biologically active agent known to affect the oncogene addicted pathway to one well and introducing an unknown biologically active agent suspected of affecting the oncogene affected pathway to another well, wherein the introductions occur after at least one impedance value for the corresponding well is obtained; generating impedance-based curves from the impedance values or cell indicies from each well; comparing the impedance-based curves between the at least one known biologically active agent and the unknown biologically active agent, and if sufficiently similar, concluding the unknown biologically active agent affects a same oncogene addicted pathway similarly as the at least one known biologically active agent.

A variety of oncogene addicted cells may be used with the methods, including those selected from the group consisting of a cancer cell, optionally a lung cancer cell, a gastric cancer cell, a melanoma cell, an epidermoid cell, a colon cancer cell, a neuroblastoma cell, and a virus infected cell. Oncogene addicted cells can be those that overexpress an oncogene in an oncogene addicted pathway or can be isogenic cells that express an oncogene at a level similar to that of a natural cancer cell.

While the modulation of a variety of oncogene addicted pathways can be monitored, and distinguished from one another among these include a cMET pathway, an EGFR pathway, a PDGFR pathway, an ALK pathway, a P13K pathway, a serine/threonine kinase pathway, and a b-Raf pathway. As such, the methods are particularly useful when the at least one known biologically active agent is an inhibitor of a kinase selected from the group consisting of cMET, EGFR, PDGFR, ALK, P13K, a serine/threonine kinase, and b-Raf. Further analysis of the oncogene addicted pathway can be achieved when the at least one known biologically active agent and/or the unknown biologically active agent are provided in different concentrations to a same cell type in different wells to generate a dose response curve, to determine an EC50, or determine an IC50.

In another embodiment a method of generating a time dependent cellular response profile (TCRP) for the modulation of an oncogene addicted pathway through the use of a cell population overexpressing an oncogene and a known biologically active agent is provided. The method includes: providing a system for monitoring cell-substrate impedance comprising a plurality of impedance monitoring wells; adding a population of cells overexpressing an oncogene forming part of an oncogene addicted pathway to at least two wells and adding parental cells to at least two other wells; monitoring impedance of the at least four wells over a period of time to obtain impedance values and optionally determining cell indices from the impedance values; introducing at least one known biologically active agent which affects the expression of the oncogene to at least one well of cells overexpressing the oncogene and to at least one well of parental cells, and introducing a vehicle control to another well of cells overexpressing the oncogene and to another well of parental cells, wherein the introductions occur after at least one impedance value for the corresponding well is obtained; generating an impedance-based curve from the impedance values or cell indicies for each of the wells; comparing the impedance-based curves between wells having the cells overexpressing the oncogene to determine a time dependent response profile for cells overexpressing the oncogene and comparing the impedance-based curves between the wells having parental cells to determine a time dependent response profile for parental cells; comparing the time dependent cellular response profiles between cells overexpressing the oncogene and parental cells; and if significantly different, categorizing the cellular response profile in overexpressing cells as a signature profile for modulation of an oncogene or oncogene addicted pathway.

In another aspect of the present invention, a method of identifying unknown biologically active agents which target specific oncogene or oncogene addicted pathways is provided. The method includes: providing a system for monitoring cell-substrate impedance having a plurality of impedance monitoring wells; adding oncogene addicted cells (or cells overexpressing oncogenes or cells isogenically expressing oncogenes) to at least two wells; monitoring impedance of the at least two wells over a time period and optionally determining cell indices from impedance values; introducing at least one known biologically active agent which targets the oncogene to one well and at least one unknown biologically active agent to another well, wherein the introductions occur after at least one impedance value for the corresponding well is obtained; generating impedance-based curves from the impedance values from each well to obtain a TCRP for both the known and unknown biologically active agents; comparing the impedance-based TCRPs between the known biologically active agent and unknown biologically active agent and if similar the compound is considered a hit which may also target the oncogene or oncogene addicted pathway.

In still another embodiment, a method of identifying whether a biological agent affects an oncogene addicted pathway is provided, which includes: providing a system for monitoring cell-substrate impedance comprising a plurality of impedance monitoring wells; adding a population of cells overexpressing an oncogene forming part of an oncogene addicted pathway to at least two wells; monitoring impedance of the at least two wells over a time period to obtain impedance values and optionally determining cell indices from the impedance values; introducing a known biologically active agent known to affect the oncogene addicted pathway to one well and introducing an unknown biologically active agent suspected of affecting the oncogene addicted pathway to another well, wherein the introductions occur after at least one impedance value for the corresponding well is obtained; generating impedance-based curves from the impedance values or cell index curves from each well; comparing the impedance-based curves between the known biologically active agent and the unknown biologically active agent, and if sufficiently similar, concluding the unknown biologically active agent affects a same oncogene addicted pathway similarly to the known biologically active agent.

(H1047R). (B) The parental cell line, 10T1/2 tva, did not show sharp decreases (within 10 min of compound addition) in CI upon PI3K inhibition.

Figure 31:
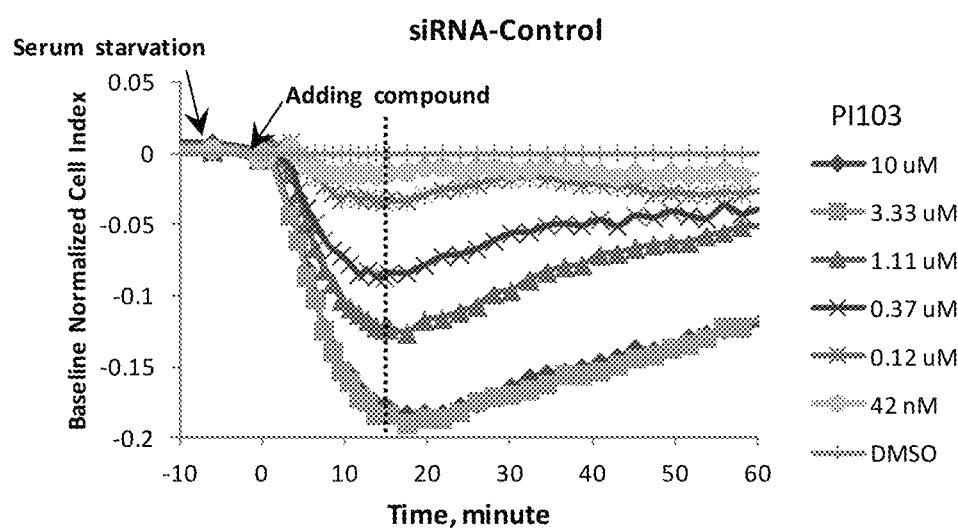
Figure 31:
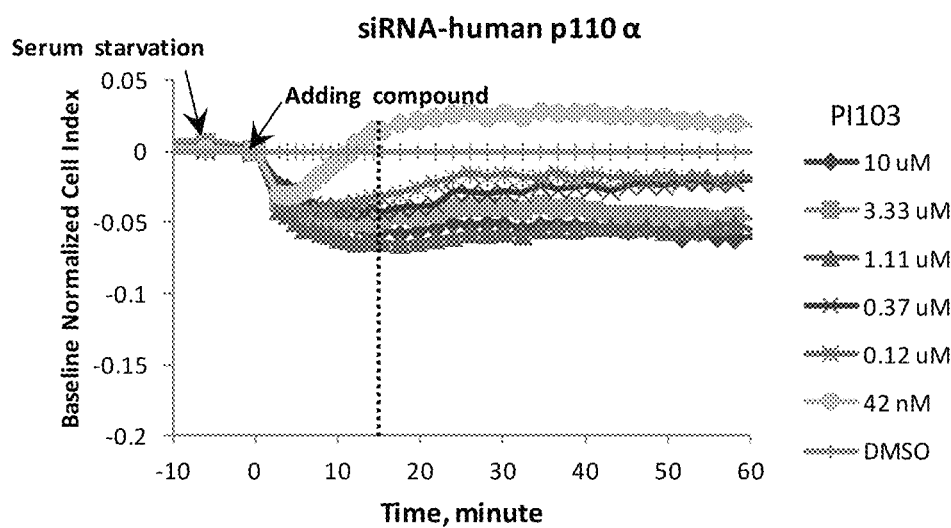

FIG. 31 shows the effect of PI3K inhibitor on the engineered mouse fibroblast cell line, 10T1/2 expressing human p110α (H1047R) with and without siRNA knockdown of human p110α. Cells were serum starved for 5 hour. The cell index was normalized at time of compound addition. At the indicated time point of treatment, increasing concentrations of PI103 (0-10 uM) was added to the cells and the cell responses were monitored. (A) 10T1/2 tva-H1047R in the presence of control siRNA showed show sharp decreases (within 10 min of compound addition) in CI upon PI3K inhibition. Plotting the normalized CI responses (10 min post compound addition) versus the corresponding log concentration allows for calculation of the IC50 of PI3K for the mutant p110α (H1047R). (B) 10T1/2 tva-H1047R in the presence of siRNA targeting human p110α showed no sharp decrease (within 10 min of compound addition) in CI upon PI3K inhibition.

Figure 32:
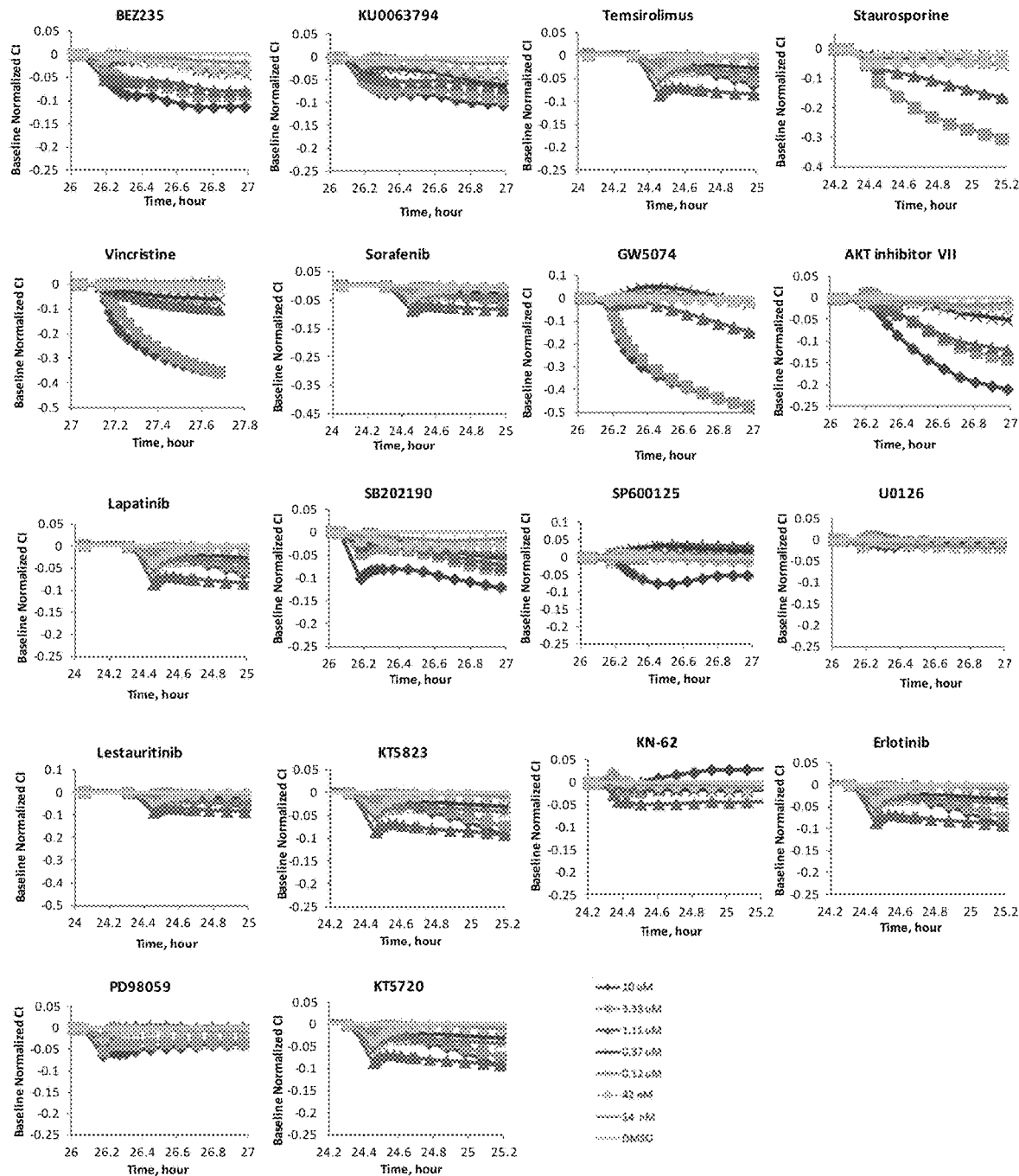

FIG. 32 shows impedance-based time-dependent cellular profiles (TCRPs) of 10T1/2 tva-H1047R in response to a panel of protein kinase inhibitors on xCelligence system (Roche/ACEA). The cell index (CI) was normalized at time of compound addition. At the indicated time point of treatment, increasing concentrations of BEZ235, KU0063794, Temsirolimus, Staurosporine, vincristine, sorafenib, GW5074, AKT inhibitor VIII, Lapatinib, SB202190, SP600125, U0126, Lestaurtinib, KT5823, CaM kinase inhibitor-KN-62, Erlotinib, PD98059 and KT5720 (from 0 to 10 uM) were added to the cells and the cell responses were monitored.

Figure 33:
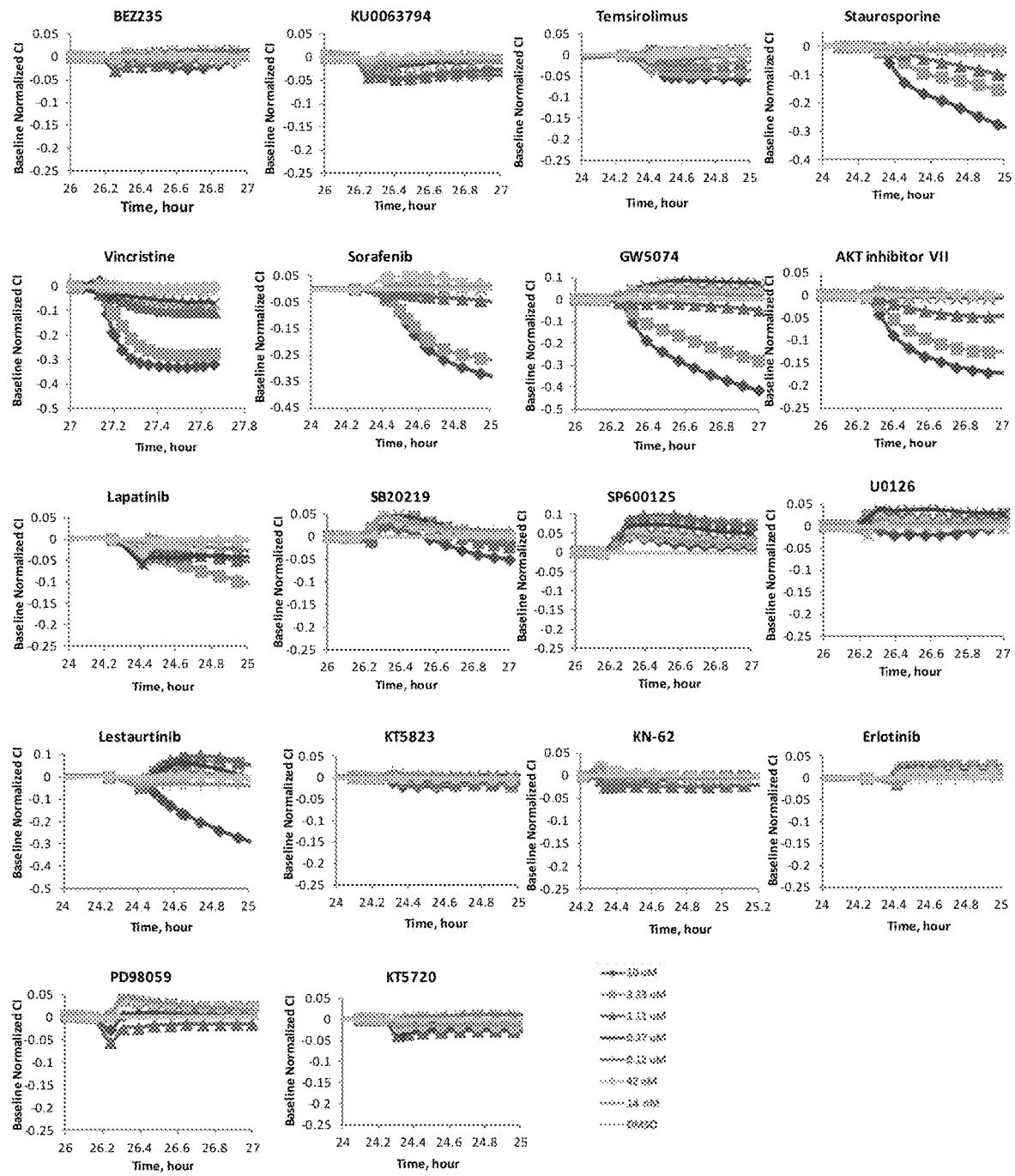

FIG. 33 shows time-dependent cellular profiles (TCRPs) of 10T1/2 tva in response to a panel of protein kinase inhibitors on xCelligence system (Roche/ACEA). The cell index (CI) was normalized at time of compound addition. At the indicated time point of treatment, increasing concentrations of BEZ235, KU0063794, Temsirolimus, Staurosporine, vincristine, sorafenib, GW5074, AKT inhibitor VIII, Lapatinib, SB202190, SP600125, U0126, Lestaurtinib, KT5823, CaM kinase inhibitor-KN-62, Erlotinib, PD98059 and KT5720 (from 0 to 10 uM) were added to the cells and the cell responses were monitored.

Figure 34:
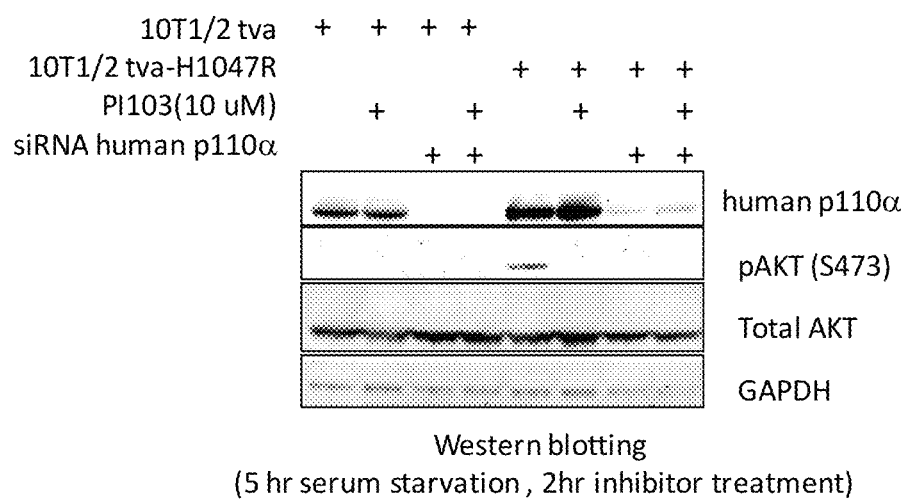

FIG. 34 is the Western blot showing the knockdown efficiency of siRNA targeting human p110α. Both 10T1/2 tva-H1047R and its parental cell line 10T1/2 tva were serum starved for 5 hours and treated with and without PI3K inhibitor, PI103 for 2 hours. Cells were lysed and subject to Western analyses. PI103 at 10 uM efficiently inhibited PI3K downstream signal (AKT phosphorylation). Equal intensity of GAPDH bands indicated equal protein loading.

Figure 35:
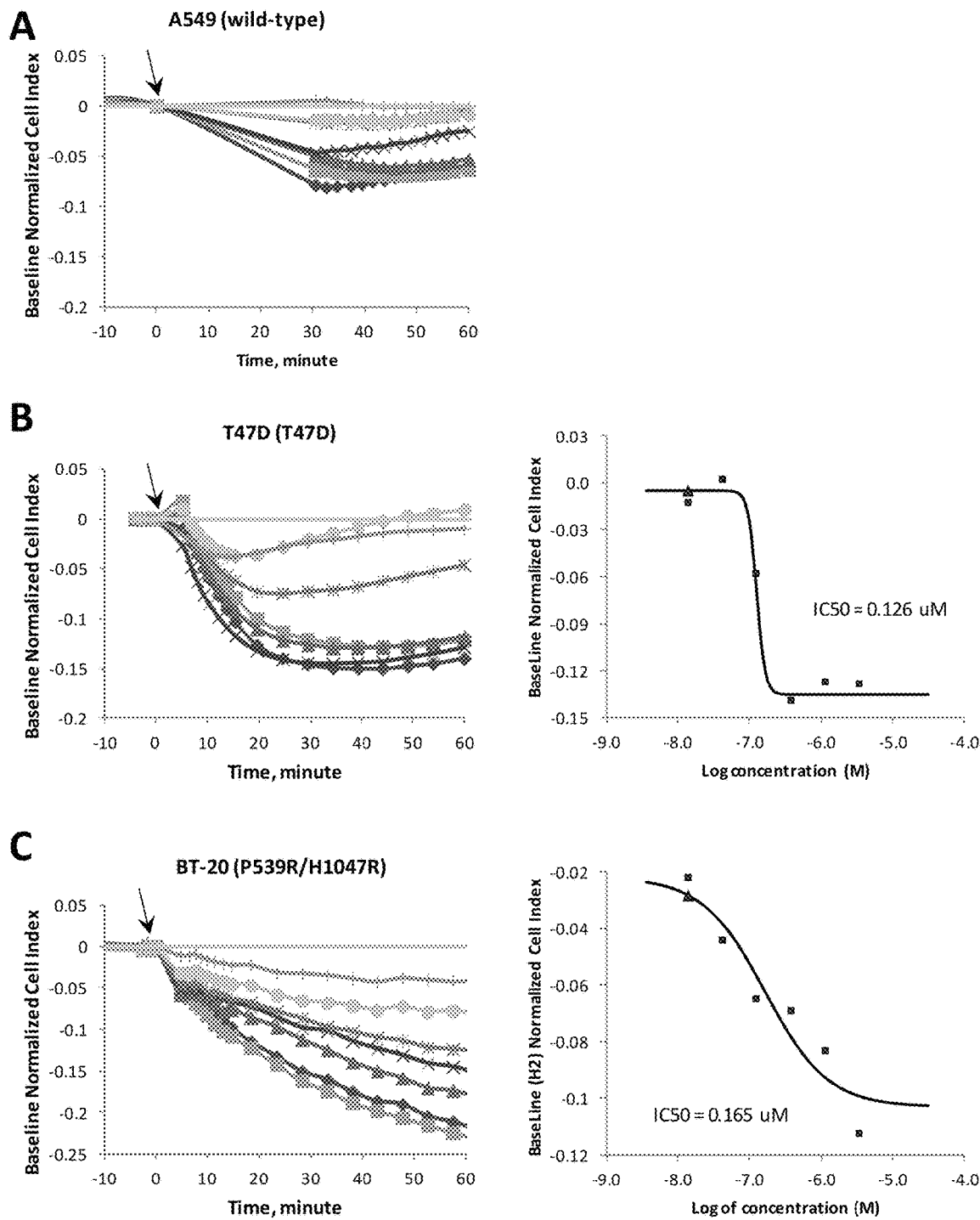

FIG. 35 shows effect of PI3K inhibitor on p110α wild-type cell line (A) A549 and mutant cell lines (B) T77D (T47D) and (C) BT20 (P539R/H1047R). Cells were serum starved for 5 hour. The cell index was normalized at time of compound addition. At the indicated time point of treatment, increasing concentrations of PI103 (0-10 uM) was added to the cells and the cell responses were monitored. Plotting the normalized CI responses responses (10 min post compound addition) versus the corresponding log concentration allows for calculation of the IC50 of PI103 for the mutant p110α T47D and P539R/H1047R.

DETAILED DESCRIPTION OF THE INVENTION

A. Definitions

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

As used herein, "biocompatible membrane" means a membrane that does not have deleterious effects on cells, including the viability, attachment, spreading, motility, growth, or cell division.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

As used herein, "each well contains . . . serially different concentration of a test compound" means that each well contains a test compound with a serially diluted concentrations, e.g., an one-tenth serially diluted concentrations of 1 M, 0.1 M, 0.01 M, etc.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus dose concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks. In another example, a test compound may result in a change in cell morphology, which can be monitored or measured by cell-substrate impedance. Thus, cell-substrate impedance and cell index may follow a dose-dependent relationship on the concentration of the test compound. One may construct dose-response by plotting the maximum change in cell-substrate impedance or maximum change in cell index after adding the test compound at each compound concentration to the cells with respect to the cell-substrate impedance or cell index prior to the addition of the test compound. From such dose-response curve, one may derive important parameters such as EC50 or IC50 of the test compound.

As used herein, "sample" refers to anything which may contain a moiety to be isolated, manipulated, measured, quantified, detected or analyzed using apparatuses, microplates or methods in the present application. The sample may be a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

An "agent" or "test agent" is any compound whose activity or direct or indirect effect or effects on cells is investigated in any assay. A test agent can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, an antibody, a nucleic acid, or any combination of these. An agent for testing, such as a known agent or an unknown agent can be a synthetic compound, a naturally occurring compound, a derivative of a naturally-occurring compound, etc. Thus the specific structure of an agent can be known or unknown. In one application of the present invention, an agent is capable of, or is suspected of, being capable of modulating an oncogene addicted pathway. In another application of present invention, an agent is capable of, or is suspected of, inducing expression or inhibiting expression of an oncogene such as through modulation of transcription, translation or the like. In still another application, an agent is capable of, or is suspected of, interacting with cells (for example, binding to cell surface receptor, or inhibiting certain intracellular signal transduction pathway, or activating cells).

A "known biologically active agent" is a compound for which at least one activity is known. In the present invention, a known agent preferably is a compound for which one or more direct or indirect effects on oncogene addicted cells are known. Preferably, the structure of a known biologically active agent is known, but this need not be the case. Preferably, the mechanism of action of a known compound on cells is known, for example, the effect or effects of a known biologically active agent on cells can be, as nonlimiting examples, stimulation or inhibition of an oncogene addicted pathway.

A "Cell Index" or "CI" is a parameter that can be derived from measured impedance values and that can be used to reflect the change in impedance values. There are a number of methods to derive or calculate Cell Index. A "Normalized Cell Index" at a given time point is calculated by dividing the Cell Index at the time point by the Cell Index at a reference time point. Thus, the Normalized Cell Index is 1 at the reference time point. Description of "cell index", "normalized cell index", "delta cell-index" and "cell change index" can be found in U.S. patent application Ser. Nos. 10/705,447, 10/987,732 and 11/055,639, and in U.S. Pat. No. 7,192,752, herein incorporated by reference for all description and disclosure regarding these parameters including "cell index", "normalized cell index", "delta cell-index" and "cell change index".

As used herein, "activities" of a kinase means the kinase activities (phosphorylation capability) or its binding activities to it substrates/cofactors/partners.

As used herein, "impedance-based curves" refer to curves generated from impedance values, cell indicies, cell change indices, or normalized cell indices over time. An impedance based curve over time for a particular agent and a cell population is also referred to as a time dependent cellular response profile (TCRP).

As used herein, "significant difference between impedance based curves" is a difference being defined as any changes relative to two curves are greater or equal to 2% of impedance value or Cell Index value at any given time point. Preferably, impedance-based curves for a biologically active agent being "significantly different" from that of the control means that at at least one time point in the curves, there are greater than 2%, greater than 3%, greater than 5%, greater than 10%, greater than 15%, or greater than 20% differences between impedance values or cell index values for biologically active agents and the control. Even more preferably, impedance-based or cell index-based curves for a biologically active agent being "significantly different" from that of the control refers to that at multiple time points in the curves, there are greater than 2%, greater than 3%, greater than 5%, greater than 10%, greater than 15%, or greater than 20% differences between impedance values or cell index values for biologically active agents and the control. There are other ways to determine whether impedance-based or cell index-based curves for a biologically active agent is "significantly different" from that of the control. For example, if the "correlation coefficient" between two curves is less than a pre-determined value (for example, 0.7 or 70%), then the two curves under comparison are termed "significantly different". In this example, this pre-determined value for "having the significance difference" may be different for different applications. In another example, if the values for "a single characteristic parameter" for two curves differ by more than a pre-determined value (for example, 10%), then the two curves under comparison are termed "significantly different". Similar to the example above, this pre-determined value for "having the significance difference" may be different for different applications. In yet another example, if the distance between two curves is larger than a pre-determined value, then the two curves under comparison are termed "significantly different". Like the above two examples, the pre-determined value for "having the significance difference" may be different for different applications. One aspect of the present invention is directed to a method for comparing and categorizing cell responses to biologically active agents. Thus, the time periods used for comparing impedance-based curves or cell index curves to determine whether "significant difference" exists are generally time periods after cells being treated with biologically active agents or the control.

As used herein, "two impedance-based curves are 'sufficiently similar'" means that when comparing these curves for their similarity using a mathematical calculation method, the calculated result meets a "similarity threshold". For example, when "correlation coefficient" is used to calculate the similarity between two curves, the two curves are "sufficiently similar" if the correlation coefficient between the two curves is more than 0.9 (90%). Here, 0.9 (90%) is a "similarity threshold". The similarity threshold may attain different values (for example, 0.95 or 0.87), depending on specific application conditions of the invention. In another example, "single characteristic parameter" is used to calculate the similarity between two curves. Two curves are "sufficiently similar" if values for such characteristic parameter for the two curves differ less than 10%. Here, 10% is a similarity threshold. The similar threshold may have other values (for example, 5% or 12%), depending on specific application conditions of the invention. In still another example, "distance between curves" is calculated for comparing two curves and for determining similarity between curves. In this case, two curves are "sufficiently similar" if distance between the two curves is smaller than a "similarity threshold value". Like the above two example, the similarity threshold may have different values, depending on specific application conditions of the invention. Since the determination of whether two curves are sufficiently similar is for the purpose of comparing and categorizing cell responses to biologically active agents, the time periods used for comparing impedance-based curves, which may include cell index curves, to determine whether "sufficient similarity" exists are generally time periods after cells being treated with biologically active agents or the control.

As used herein, "two curves have 'sufficient similarity'" means that the two curves are sufficiently similar.

B. Devices and Systems for Monitoring Cell-Substrate Impedance and Methods for Calculating Cell Index (CI)

The methods of the present invention utilize impedance-based systems for monitoring or detecting changes in impedance in response to the exposure or introduction of one or more biologically active agents to cells. Suitable impedance-based devices are those that are capable of detecting changes in impedance of a cell population. Detecting changes in impedance of cells requires the cells to attach to the electrode array during at least partial time in the experiment test. For example, cells may attach to the electrode array before the treatment with biologically active agents and its attachment status may or may not be affected by biologically active agents. In another example, cells do not attach to the electrode array before the treatment with biologically active agents and cells become attached to the electrode array after being exposed to biologically active agents. Thus, the substrate must be biocompatible with the cell or cell population.

Generally, impedance-based devices include a conductive electrode array fabricated on a non-conductive substrate and operably connected to an impedance analyzer. A computer loaded with appropriate software may be used to operate the system and may also be used in analysis of impedance measurements, such as in the generation or comparison of impedance-based. More specifically, the impedance-based device may include a nonconducting substrate; two or more electrode arrays fabricated on the substrate, where each of the two or more electrode arrays comprises two electrode structures; and at least two connection pads, each of which may be located on an edge of the substrate. In preferred embodiments the electrode array is planar or substantially planar.

Preferably, each electrode array of the device has approximately uniform electrode resistance across the entire array. In some embodiments, the substrate of the device has a surface suitable for attaching a biological molecule or organic compound (such as covalently or noncovelently bonding). The substrate may also be suitable for a attaching a cell where cell attachment or spreading on the substrate can result in a detectable change in impedance between or among the electrode structures within each electrode array.

An electrode array may be two or more electrode structures that are constructed to have dimensions and spacing such that they can, when connected to a signal source, operate as a unit to generate an electrical field in the region of spaces around the electrode structures. An electrode structure refers to a single electrode, particularly one with a complex structure (for example, an electrode structure can comprise two or more electrode elements that are electrically connected together). In devices utilized with the present invention, an electrode array comprises two electrode structures, each of which comprises multiple electrode elements, or substructures. In preferred embodiments of the present invention, the electrode structures of each of the two or more electrode arrays of a device have substantially the same surface area. In preferred embodiments of a device of the present invention, each of the two or more electrode arrays of a device comprise two electrode structures, and each electrode structure comprises multiple electrode elements. Each of the two electrode structures of an electrode array is connected to a separate connection pad that may be located at the edge of the substrate.

Thus, in devices of the present invention, for each of the two or more electrode arrays of the device, the first of the two electrode structures is connected to one of the two or more connection pads, and the second of the two electrode structures is connected to another of the two or more connection pads. Preferably, each array of a device is individually addressed, meaning that the electrical traces and connection pads of the arrays are configured such that an array can be connected to an impedance analyzer in such a way that a measuring voltage can be applied across a single array at a given time by using switches (such as electronic switches).

Each electrode array of the device has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

For a device utilized with the present invention, preferred arrangements for the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the array, the field strength is related to the potential difference between the nearest point on a first electrode structure of the array and the nearest point on a second electrode structure of the array. It is therefore desirable to have similar electric potential drops across the electrode elements and across the electrode buses of a given array. Based on this requirement, it is preferred to have an approximately uniform electrode resistance distribution across the whole array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Devices of the present invention are designed such that the arrays of the device have an approximately uniform distribution across the whole array. This can be achieved, for example, by having electrode structures and electrode buses of particular spacing and dimensions (lengths, widths, thicknesses and geometrical shapes) such that the resistance at any single location on the array is approximately equal to the resistance at any single other location on the array. In most embodiments, the electrode elements (or electrode structures) of a given array will have even spacing and be of similar thicknesses and widths, the electrode buses of a given array will be of similar thicknesses and widths, and the electrode traces leading from a given array to a connection pad will be of closely similar thicknesses and widths. Thus, in these preferred embodiments, an array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In preferred embodiments of the present invention, a device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments of the present invention, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in parent U.S. patent application Ser. No. 10/705,447, herein incorporated by reference for all disclosure on fabrication and design of electrically conductive trace on substrates.

Appropriate electronic connection means such as metal clips engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. patent application Ser. No. 10/705,447, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

In some embodiments a portion of the surface of the substrate is modified to include some coated molecules. Examples of coated molecules that may be desired include those that are involved or may be involved in cell adhesion or cell spreading. The present invention includes a variety of coated molecules including a DNA molecule, an RNA molecule, a protein, a polypeptide and oligopeptide and the like. Molecules of particular interest may include an antibody, a ligand, a peptide, a receptor, one or more proteins or compounds present in the extracellular matrix (ECM), a molecule or compound capable of binding an integrin, a cell surface receptor and the like. In some embodiments a peptide such as an arginine-glycine-aspartic acid (RGD) motif or some form thereof is the coated molecule. The present invention also includes coated molecules that are agonists or antagonists for a cell surface receptor involved in cell adhesion, including integrins, growth factor receptors, E-cadherins, N-cadherins, PECAMS and ICAMS.

The modification may ultimately result in a coated surface or a surface that is coated at least in part with a coated molecule. The coated portion may represent a first portion, a second portion and the like. The region may also be referred to as a test portion or a control portion depending on the assay. When utilizing wells with the present invention, an inner surface of the wells may be coated at least in part with a coated molecule. The coated molecules may interact with the substrate in any suitable fashion. For example, the coated molecules may be covalently bound, ionically bound, bound by Van der Waals forces and the like to the substrate or electrode. The coated molecules may be attached directly to the substrate or electrode or may be attached via an intermediate structure. As a nonlimiting example, coated molecules may be bound by incubating the coated molecule in a suitable medium such as phosphate buffered saline (PBS), borate buffered saline (BBS) and the like. Alternatively, an intermediate such as poly-L-lysine may be applied to the substrate then attached to the coated molecules.

Descriptions of electrode arrays used for impedance measurement that apply to the devices of the present invention are described in U.S. patent application Ser. No. 10/705,447, herein incorporated by reference for all disclosure relating to electrode arrays (or structural units), electrode structures, electrode materials, electrode dimensions, and methods of manufacturing electrodes on substrates.

Preferred electrode arrays for devices of the present invention include arrays comprising two electrode structures, such as, for example, spiral electrode arrays and interdigitated arrays. In some preferred devices of the present invention, electrode arrays are fabricated on a substrate, in which the arrays comprises two electrode structures, each of which comprises multiple circle-on-line electrode elements, in which the electrode elements of one structure alternate with the electrode elements of the opposite electrode structure. In a preferred embodiment the electrical circuitry includes gold-coated interdigitated microelectrodes (or electrode structures) in a circle-on-line geometry. Although, additional electrode geometries are possible, the circle-on-line geometry maximizes the coverage area in a single microtiter well with maximal sensitivity.

Preferably, the electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an array of the present device of the present invention are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

A device of the present invention can include one or more fluid-impermeable receptacles, which serve as wells. Such receptacles may be reversibly or irreversibly attached to or formed within the substrate or portions thereof (such as, for example, wells formed as in a microtiter plate). In another example, the device of the present invention includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. patent application Ser. No. 10/705,447, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device of the present invention is associated with a fluid-impermeable container or receptacle, such as, for example, a well. Preferably, the device of the present invention is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some preferred embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in U.S. patent application Ser. Nos. 10/705,447, 10/987,732, 11/055,639, and U.S. Pat. No. 7,192,752, all herein incorporated by reference for disclosure of multiwell impedance measurement devices, including their design, composition, and manufacture. A device of the present invention preferably has between 2 and 1,536 wells, more preferably between 4 and 384 wells, and even more preferably, between 16 and 96 wells, all or less than all or which are associated with electrode arrays. In the preferred embodiments cells are added to 16, 24, 96, 384 or 1536 wells since these are commonly available well configurations.

In some preferred embodiments, commercial tissue culture plates can be adapted to fit a device of the present invention. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

C. Methods for Performing Real-Time Cell-Based Screening Using Real-Time Cell Electronic Sensing (RT-CES) System The present invention provide cell-based assays that can be performed in real time to assess cell proliferation, cell growth, cell death, cell morphology, cell membrane properties (for example, size, morphology, or composition of the cell membrane) cell adhesion, and cell motility. Thus the assays can be cytotoxicity assays, proliferation assays, apoptosis assays, cell adhesion assays, cell activation or stimulation assays, anti-cancer compound efficacy assays, receptor-ligand binding or signal transduction analysis, assays of cytoskeletal changes, assays of cell structural changes (including but not limited to, changes in cell membrane size, morphology, or composition), cell quantification, cell quality control, time-dependent cytotoxicity profiling, assays of cell differentiation or de-differentiation, detection or quantitation of neutralizing antibodies, specific T-cell mediated cytotoxic effect assays, assays of cell adhesivity, assays of cell-cell interactions, analysis of microbial, viral, or environmental toxins, etc.

The assays are real-time assays in the sense that cell behavior or cell status being assayed can be assessed continuously at regular or irregular intervals. Cell behaviors, cell responses, or cell status can be assayed and the results recorded or displayed within seconds to minutes of their occurrence. The cell response during an assay can be monitored essentially continuously over a selected time period. For example, a culture can be monitored every five to fifteen minutes for several hours to several days after addition of a reagent. The interval between impedance monitoring, whether impedance monitoring is performed at regular or irregular intervals, and the duration of the impedance monitoring assay can be determined by the experimenter.

Thus, the cell-based impedance assays of the present invention avoid inadvertently biased or misleading evaluation of cell responses due to the time point or time points chosen for sampling or assaying the cells. In addition, the assays do not require sampling of cell cultures or addition of reagents and thus eliminate the inconvenience, delay in obtaining results, and error introduced by many assays.

In brief, for measurement of cell-substrate or cell-electrode impedance using the technology of the present invention, cell-substrate impedance monitoring devices are used that have microelectrode arrays with appropriate geometries fabricated onto the bottom surfaces of wells such as microtiter plate wells, or have a similar design of having multiple fluid containers (such as wells) having electrodes fabricated on their bottom surfaces facing into the fluid containers. Cells are introduced into the fluid containers of the devices, and make contact with and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals can be measured automatically and in real time, and can be converted to digital signals for processing and for analysis.

Preferably, cell-substrate impedance assays are performed using a system of the present invention that comprises a device of the present invention, an impedance monitor, a device station that comprises electronic circuitry and engages the device and the impedance analyzer, and a software program that controls the device station and records and analyzes impedance data.

Using a system of the present invention, a cell index can optionally be automatically derived and provided based on measured electrode impedance values. The cell index obtained for a given well reflects: 1) how many cells are attached to the electrode surfaces in this well, and 2) how well (tightly or extensively) cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

The general approach to impedance monitoring for for performing cell-based assays, includes: a) providing a cell-substrate impedance monitoring device of the present invention that comprises two or more electrode arrays, each of which is associated with a fluid container of the device; b) attaching the device to an impedance monitor; c) introducing cells into one or more fluid containers of the device; and d) monitoring cell-substrate impedance of at least one of the fluid containers that comprises an electrode array and cells. Preferably, impedance is monitored from the at least one fluid container to obtain impedance measurements at at least three time points. Preferably, impedance measurements or impedance values derived from impedance measurements from at least three time points are plotted versus time to generate one or more impedance curves for the one or more fluid containers. In a related aspect of the present invention, a method is provided for performing cell-based assays in an impedance-monitoring system, comprising: a) providing a cell-substrate impedance monitoring system of the present invention that comprises a device having two or more electrode arrays, each of which is associated with a well of the device; b) introducing cells into one or more wells of the device; and c) monitoring cell-substrate impedance of at least one of the wells that comprises an electrode array and cells. Preferably, impedance is monitored from the one or more wells of the device to obtain impedance measurements at at least three time points. Preferably, impedance measurements or impedance values derived from impedance measurements from at least three time points are plotted versus time to generate one or more impedance curves for the one or more wells.

The method can be used to assay cell status, where cell status includes, but is not limited to, cell attachment or adhesion status (e.g. the degree of cell spread, the attachment area of a cell, the degree of tightness of cell attachment, cell morphology) on the substrate including on the electrodes, cell growth or proliferation status; number of viable cells and/or dead cells in the well; cytoskeleton change and re-organization and number of cells going through apoptosis and/or necrosis. The cell-based assays that be performed with above methods include, but are not limited to, cell adhesion, cell apoptosis, cell differentiation, cell proliferation, cell survival, cytotoxicity, cell morphology detection, cell quantification, cell quality control, time-dependent cytotoxicity profiling, IgE-mediated cell activation or stimulation, receptor-ligand binding, viral and bacterial toxin mediated cell pathologic changes and cell death, detection and quantification of neutralizing antibodies, specific T-cell mediated cytotoxic effect, and cell-based assays for screening and measuring ligand-receptor binding.

In preferred embodiments of this aspect of the present invention, cells are added to at least two fluid containers of a device, each of which comprises an electrode array, and impedance is monitored from at least two wells that comprise cells and an electrode array.

Cells are typically added to the wells of the device by transferring a cell suspension into the desired well. Cells may be added to at least two, at least three or more of the wells as desired by the particular study. Thus, cells may be added to all wells or less than all wells. In various embodiments, cells are added to 2, 4, 16, 96, 384 or 1,586 wells. Cells may be incubated within the wells, such as to allow the cells sufficient time to settle down to the electrode array. In other embodiments incubation permits a cell population to stabilize and thus provide a baseline impedance value that does not significantly vary. Cells may be incubated or cultivated in the wells overnight, over multiple nights or over weeks depending on the desired experiment. Cells, such as those derived from a cell line, may be seeded in one or more wells then incubated until a desired population is reached. Alternatively, cells such as those isolated from a human may be added to wells upon isolation and incubated less than one 24 hour day, 6 hours, 2 hours, 1 hour or less than 1 hour prior to beginning an experiment.

With respect to the cells themselves, since the methods permit the generation and catagorization of signature time dependent response profiles, the present methods may utilize a variety of oncogene addicted cells having different or similar oncogenic pathways. Among some of the oncogene addicted cells that may be used include a cancer cell, a lung cancer cell, a gastric cancer cell, a melanoma cell, an epidermoid cell, a colon cancer cell, a neuroblastoma cell, and a virus infected cell. In some embodiments, the oncogene addicted cells are isogenic cells that express an oncogene at a level similar to that of a natural cancer cell. Cells expressing the following oncogene addicted pathways are of particularl interest: a cMET pathway, an EGFR pathway, a PDGFR pathway, an ALK pathway, a P13K pathway, a serine/threonine kinase pathway, and a b-Raf pathway. The skilled artisan will appreciate that the cells may be primary cells, cells isolated from tumors, cell lines and the like. Further, the cells are preferably mammalian and most preferably human; however, other primates are also acceptable including murine or mouse, dog, pig, cow and the like.

Impedance may be monitored over a predetermined or variable period of time. Preferably impedance monitoring begins prior to the addition of a biologically active agent and may begin prior to the addition of a cell suspension to the well. Impedance monitoring may assist in determining the point in which cells are suited for the introduction of a biologically active agent. In the preferred embodiment impedance is monitored continuously over time and does not require specific time point measurements. Impedance is preferably measured in real time. Suitable time periods may be predetermined such as over a desired number of seconds, minutes, hours, days, weeks and the like or impedance may be monitored until the user decides to stop impedance monitoring, such as at some time after treatment of cells with biologically active agents when no change or no significant change in impedance value occurs.

In an exemplary embodiment, cell culture medium is first added to the wells of microtiter plate, which are integrated with the gold microelectrodes in each well (also referred to as an "E-Plate") to measure background or baseline impedance and calculate the Cell Index. The cells are then added to the wells of the E-Plate at pre-determined density and are continuously monitored to observe initial cell attachment and cell proliferation for any time period, for example, about 16-24 hours, prior to addition of biologically active agents to cells. The stage of cell attachment and growth prior to biologically active agent addition serves as cell type specific cell growth profile, which is informative for quality control purposes. This information can be used to assess cell health and ensure consistency between cells in different wells in the same E-Plate or across different E-Plates in different experiments.

It has been found that normalizing curves to the last time point of impedance measurement prior to biologically active agent introduction allows for better comparison of cell index curves. Thus, at the last time pint of impedance measurement prior to biologically active agent introduction, normalized cell index values for all the wells is one, irrespective of exact number of cells in any wells. Any difference in changes in normalized cell index values after introduction of biologically active agents between different wells are associated only with differences in cells responding to the treatment of biologically active agents.

In preferred embodiments, impedance monitoring begins before the addition of a biologically active agent. Although nonlimiting, once the cells reach a predetermined or desired Cell Index, one or more biologically active agents are added to one or more wells and preferably a control is added to a second well. The time between cell seeding to introduction of biologically active agents may vary depending on the health of the cell(s), proliferation rate of the cells, lineage and the like. Typically about 16-24 hours for time between cell seeding to introduction of biologically active agents is sufficient, with increased or decreased times also within the scope of the present invention. After introduction of biologically active agents, the interaction between biologically active agents with cells cultivated on the microelectrodes may result in modulation of cell number, cell adhesion quality and cell morphology and therefore may result in changes in the Cell Index.

Biologically active agents are those that have a biological effect on an oncogene addicted cells or suspected of having a biological effect on cells. Biological effects may be any known to those skilled in the cellular, biological or chemical arts. Biological effects include activation or inactivation of a cellular pathway. Non-limiting examples of the implication of modulating oncogene addicted cell pathways result in differences of cell viability, cell adhesion, apoptosis, cell differentiation, cell proliferation, cell morphology, cell cycle, and cell spreading. Thus biological effect may result in a change in cell size, shape, granularity, morphology and the like.

A biologically active agent may be a compound, a peptide, a protein, an antibody or antibody fragment, an apatmer, a ribozyme, a siRNA, a miRNA, a nucleotide, an anti-sense oligo, a virus, and a combination thereof. A biologically active agent may be a compound such as a protein tyrosine kinase inhibitor, a protein synthesis inhibitor, a nuclear receptor agonist and/or antagonist, or the like. Biologically active agents may be added at a single concentration, at multiple concentrations, at serial dilutions and the like. In one example, multiple biologically active agents having the same or similar mechanism may be added to an E-Plate. In another example, multiple biologically active agents having different mechanisms may be added to an E-Plate at the same or different times. In yet another example, multiple known biologically active agents having known mechanisms may be added to an E-Plate at the same or different times. In yet another example, multiple unknown biologically active compounds having unknown mechanisms may be added to an E-Plate at the same or different times. In yet another example, multiple unknown biologically active agents with some having known mechanisms and some others having unknown mechanisms may be added to an E-Plate at the same or different times.

While the biologically active agent is introduced into the well, the cells are continuously monitored for changes in impedance or Cell Index and compared to untreated or control treated wells. The continuous monitoring of Cell Index changes over time in response to biologically active agents results in very specific cell response profiles, which is a manifestation of the mechanism of action of the biologically active agents within the cell.

Due to the kinetic nature of the profiling approach both short term and long term biologically active agent activity can be monitored, allowing for detection of temporally isolated but distinct activities of small molecules and potentially off-target effects. These findings indicate that using impedance-based monitoring and profiling of cellular response upon exposure to biologically active compounds can provide incisive and quantitative information and novel mechanisms for existing drugs as well as experimental biological compounds. Short term refers to any short time period after introduction of biologically active agents to cells. Non-limiting examples of short term includes a time period of 3 hrs, 2 hrs, 1 hr, 30 minutes, 15 minutes, 10 minutes, 5 minutes after introduction of biologically active agents to cells. Short term period here would start at the moment of introduction of biologically active agents to cells and end within a short time range after that. Long term typically refers to a time period that is many hours after introduction of biologically active agents to cells. Long term period would start from several hours after and ends at many hours after introduction of biologically active agents to cells. Non-limiting long term period would start at 1 hr, 1.3 hr, 2 hr, 3 hr, 5 hr, 7 hr and end at 24 hr, 36 hr, 40 hr, 48 hr, 72 hr, or even longer after introduction of biologically active agents to cells. Here, both short term and long term are relative terms, and depending on different activities of biologically active agents, a short term in one experiment for one biologically active agent may be a long term in another experiment for another biologically active agent.

From the impedance measurements, an impedance-based curve may be generated or in the alternative a curve corresponding to cell index may be generated. Cell Index, being reflective of cell-electrode impedance is primarily dependent on three main factors; number of cells cultivated inside the wells, the inherent morphology of the cells and the adhesive interaction of the cells with the electrode array.

In the preferred embodiments, curves generated from wells treated with one or more biologically active agents are compared to curves generated from control wells, having no biologically active agent, but having media or a control vehicle or the like. Comparisons are preferably performed by analyzing impedance based curves that correspond to the impedance measurements or Cell Index, which is derived from impedance measurements or impedance-based curves and the difference is calculated, such as by algorithm. Furthermore, normalized cell index curves may be generated, which correspond to cell index curves normalized to the last time point of impedance measurement prior to adding a biologically active agent.

Impedance-based curves or Cell Index curves generated from wells having cells treated with a biologically active agent may initially be compared to those generated from control. If the difference between a curve generated from a treated and control well is insignificant, then the no modulation of the oncogene addicted cell. That is, if curves generated from wells treated with biologically active agents and control wells are sufficiently similar or have a sufficient degree of similarity, no modulation of an oncogene addicted pathway is deemed to have occurred. However, if the difference between curves generated from treated and control wells is significant over a short term or long term, modulation of the oncogene addicted pathway is deemed to have occurred, the time dependent response profile including cell and response and biologically active agent is categorized accordingly. That is if the impedance-based curves from impedance values or cell indicies generated from treated and control wells are significantly different, a modulation of the oncgne addicted cell is deemed to have occurred and the response may be categorized.

Cell responses to biologically active agents are compared and categorized into cell response profiles by generating cell impedance curves or cell-index curves for cells treated with the unknown biologically active agents, and comparing the impedance-based curve or optionally cell-index curve to a cellular response profile of a known or predetermined agent.

In the assays of the present invention is preferable to perform replicate test agent assays in which more than one fluid container of cells of the same type receives the same agent at the same concentration. In this case, impedance measurements or values can optionally be averaged for the assayed time points for replicate wells. Preferably, a standard deviation for the averaged values is also calculated.

Preferably, time-dependent responses of the first and second types of cells are compared to see how similar or different the responses from the two types of cells are. In one method of the present invention, impedance from a first cell type well is plotted versus time to give a first cell type impedance curve and impedance from a second cell type well is plotted versus time to give a second cell type impedance curve. Cell index (including normalized cell index or delta cell index) from wells comprising cells of different types can also be calculated from impedance data and plotted versus time to give cell index curves.

The impedance curves or cell index curves from the different cell types can be compared to determine whether the time frame, magnitude, and duration of a cells response to a compound are similar or different. Preferably, impedance curves or cell index curves generated from control wells comprising each cell type in the absence of compound are compared with the test agent curves to assess the compound-specific effects on each cell type. The effects of the agent on one or more of the two or more cell types can be effects on cell attachment or adhesion, cell growth or proliferation; the number of viable cells or dead cells; cytoskeleton organization or function; or the number of cells going through apoptosis or necrosis in response to a test compound. Assays can be designed to investigate the compound's effects on particular cellular processes or activities.

The effect of an agent on at least one of the cell types used in the assay may be known. The mechanism of action of a agent on at least one of the cell types used in the assay may be known. In such cases, comparison of the compound response of one or more different cell types with the compound response of a cell type whose response to the compound is characterized can give information as to the similarity or difference in response of a different cell type to the compound.

D. Methods for Comparing Curves

A variety of nonlimiting approaches may be used to identify similarities between curves and thus correlate biologically active agents to specific mechanisms of modulating oncogene addicted cells. In one approach, the correlation coefficient between the two curves is used to define the similarity degree between the two curves. For example, give a curve one being $C_1(t_i)$; $\{i=1, 2, 3, \ldots N\}$, and another curve being $C_2(t_i)$; $\{i=1, 2, 3, \ldots N\}$, where curve one attains a value $C_1(t_i)$ at a time point $t_i$ and curve two has a value of $C_1(t_i)$ at the time point $t_i$.

The correlation coefficient between these two curves is calculated using this approach, $$CC(1,2) = \frac{N\sum_i [C_1(t_i)C_2(t_i)] - \sum_i C_1(t_i) \cdot \sum_i C_2(t_i)}{\sqrt{\left[N\sum_i [C_1(t_i)]^2 - \left(\sum_i C_1(t_i)\right)^2\right]}\sqrt{\left[N\sum_i [C_2(t_i)]^2 - \left(\sum_i C_2(t_i)\right)^2\right]}}.$$

The larger the correlation coefficient, the more similar the two curves are. Since calculation of correlation coefficients is for comparing and categorizing cell responses to biologically active agents, thus, the time points used for calculation of correlation coefficients between curves are generally time points in a time period after cells being treated with biologically active agents or the control.

In another approach, a single characteristic parameter describing a cell response curve is determined and the difference between two such parameters is used to define the degree of similarity between the two curves. In this approach, a single parameter having a positive value is derived for each curve by appropriate calculation formulas with the value for control curves being set to 1. Then, for two given curves, the difference between parameters can be calculated. The smaller the absolute value of such difference, the more similar the two curves are.

One could define a threshold for such "similarity" if desired. Therefore similarity may vary depending on the user's needs or desires. For example, a threshold value could be 0.1, meaning that if two curves having a difference being less than 0.1, then these two curves are termed "similar".

As an example, the parameter is defined as the total area under the cell response curve for the monitored time period. Mathematically, for a given curve treated with a biologically-active agents and no-compound control curve, $C(t_i)$, $\{i=1, 2, 3, \ldots N\}$ and $C_{control}(t_i)$, $\{i=1, 2, 3, \ldots N\}$ the single parameter for the response curves to the biologically-active agents is defined as $$P = \frac{\sum_i [C(t_i) \cdot (t_i - t_{i-1})]}{\sum_i [C_{control}(t_i) \cdot (t_i - t_{i-1})]}.$$

In another embodiment, the distance between two curves is determined to define the degree of similarity between two curves. There are various ways to define the distance between two curves, each of which may be used by the present invention and incorporated herein in their entirety. In one example, the distance is the sum of square of the difference of the two curves (dY) at a set of given time points.

Assuming a and b are two single curves, define the distance between curve a and curve b ($d_{a\,b}$) as:

$$d_{ab} = \sum_{i=0}^{n} (Y_{ai} - Y_{bi})^2$$

Here, $Y_{ai}$ Y is the y value of curve a at ith-time point i, $Y_{bi}$ is the y value of curve b at ith time point.

E. Real-Time Cell Based Assays to Identify Compounds Capable of Inhibiting Oncogenes and their Signal Pathways The present invention provides methods to screen and identify putative inhibitors for oncogenes and their signal pathways using impedance-based devices. The oncogenes include but not limited to transcription factor (MYC), GTPase (RAS), receptor tyrosine kinases (e.g., EGFR, HER2, MET, PDGFR, KIT, FGFR3, ALK, VEGFR and RET), serine/therinine kinase (bRAF and AURORA Kinase), tyrosine kinase (ABL), and lipid kinase (PI3K).

Oncogene addiction refers to the acquired dependency of cancer cells on a single cellular pathway for survival or sustained proliferation, despite the fact that such cells have accumulated numerous genetic alterations. We have discovered that various oncogene addicted cell lines could produce a characteristic impedance-based TCRP (time-dependent cell response profiling), when treated with corresponding inhibitors. Thus the present invention provides methods to screen and identify compound capable of inhibiting these oncogenes as well as to predict the mechanism of actions of unknown compounds.

As an exemplary embodiment a method of generating a TCRP for the modulation of oncogene addicted cells using a known biologically active agent, which targets the oncogene has been achieved. The method includes: providing a system for monitoring cell-substrate impedance comprising a plurality of impedance monitoring wells; adding oncogene addicted cells comprising an active oncogene addicted pathway to at least two wells and adding non-oncogene addicted cells that lack the active oncogene addicted pathway to at least two other wells; monitoring impedance of the at least four wells over a period of time to obtain impedance values and optionally determining cell indices from the impedance values; introducing at least one known biologically active agent known to affect the oncogene addicted pathway to at least one well having the oncogene addicted cells and to at least one well having the non-oncogene addicted cells, and introducing a vehicle control to another well having the oncogene addicted cells and to another well having the non-oncogene addicted cells, wherein the introductions occur after at least one impedance value for the corresponding well is obtained; generating an impedance-based curve from the impedance values or from the cell indices for each of the at least four wells; comparing the impedance-based curves between wells having the oncogene addicted cells to determine a time dependent cellular response profile (TCRP) in oncogene addicted cells, and comparing the impedance based curves between the non-oncogene-addicted cells to determine a time dependent cellular response profile (TCRP) in non-oncogene addicted cells; and comparing the time dependent cellular response profiles (TCRPs) between oncogene addicted cells and non-oncogene addicted cells; and if significantly different, categorizing the time dependent cellular response profile (TCRP) in oncogene addicted cells as a signature time dependent cellular profile (TCRP) characterized as modulating an oncogene addicted pathway.

A variety of oncogene addicted cells may be used with the methods, including those selected from the group consisting of a cancer cell, optionally a lung cancer cell, a gastric cancer cell, a melanoma cell, an epidermoid cell, a colon cancer cell, a neuroblastoma cell, and a virus infected cell. Oncogene addicted cells can be those that overexpress an oncogene in an oncogene addicted pathway or can be isogenic cells that express an oncogene at a level similar to that of a natural cancer cell.

While the modulation of a variety of oncogene addicted pathways can be monitored, and distinguished from one another among these include a cMET pathway, an EGFR pathway, a PDGFR pathway, an ALK pathway, a P13K pathway, a serine/threonine kinase pathway, and a b-Raf pathway. As such, the methods are particularly useful when the at least one known biologically active agent is an inhibitor of a kinase selected from the group consisting of cMET, EGFR, PDGFR, ALK, P13K, a serine/threonine kinase, and b-Raf. Further analysis of the oncogene addicted pathway can be achieved when the at least one known biologically active agent is provided in different concentrations to a same cell type in different wells to generate a dose response curve, to determine an EC50, or determine an IC50.

While the method can obtain a plurality of single TCRPs, when the at least one biologically agent includes a multitude of biologically active agents a library of signature time dependent response profiles (TCRPs) can be produced, which may be used for subsequent screening of an unknown agent or pathway. To this end the method can further include comparing the signature TCRPs between the multitude of biologically active agents to identify a library of unique signature TCRPs.

Methods of Identifying Compounds Capable of Affecting the Activity of an Oncogene While the general consensus in the field of cancer research has been that cancer is typically the result of multiple lesions that act in concert to maintain and support cancerous growth and metastasis, work over the last decade is providing evidence that at least certain kinds of cancers may depend on only a single oncogene or oncogenic pathway for growth, proliferation and survival. This hypothesis is referred to as oncogene addiction and as a corollary to this hypothesis it can be postulated targeting these key oncogenes for drug development may provide a window of opportunity for cancer treatment. Thus oncgne addiction may present the "Achilles' heel" of cancer which may be exploited therapeutically. A profound implication of this hypothesis is that switching off this crucial pathway upon which cancer cells have become dependent should have devastating effects on the cancer cell while sparing normal cells that are not similarly addicted.

The end result of inhibiting the oncogene that the cancer cells are addicted to is cell death. While an array of compounds can lead to cell death, understanding the cell response during the time course of the compound treatment prior to cell death is critical in discovering the compounds, which specifically inhibiting the oncogenes and their signal pathways. Impedance-based TCRP (time-dependent cell response profiling) can empower us in obtaining the vital information.

Roche and ACEA Bio have developed a cell sensor array electrodes integrated on the bottom of the wells of microtiter plate (E-Plate™). The sensors are arrayed in a novel design that covers approximately 80% of the wells surface area, allowing for sensitive and quantitative detection of cellular changes. Signals from these sensors are relayed to a real time cell electronic sensing (RT-CES) system that allows for monitoring and analysis of the kinetic aspects of cellular behavior. The signals relayed are impedance changes in the ionic environment created by the application of an electric field. Disruption of this ionic environment on the sensor surface due to the presence of cells or changes in the cells morphology can lead to changes in measured impedance, which is then converted to a cell index value. The extent of the cell-electrode impedance response is dependent on the attachment quality and the sensor area covered by the cell. An increase in measured impedance value due to an increase in cell number or degree of attachment results in an increase in observed cell index. This system has been successfully used in monitoring cell proliferation and cytotoxicity, cell adhesion, and G-protein coupled receptor function. Here we describe the method to screen and identify putative inhibitors for oncogenes and their signal pathways using this system.

In one approach, a method of identifying whether a biological agent affects an oncogene addicted pathway is provided, which includes providing a system for monitoring cell-substrate impedance comprising a plurality of impedance monitoring wells; adding oncogene addicted cells comprising an active oncogene addicted pathway to at least two wells; monitoring impedance of the at least two wells over a time period to obtain impedance values and optionally determining cell indices from the impedance values; introducing an unknown biologically active agent which is suspected of affecting the oncogene addicted pathway to one well and introducing a vehicle control to another well, wherein the introductions occur after at least one impedance value for the corresponding well is obtained; generating impedance-based curves from the impedance values or cell indicies from each well; comparing the impedance-based curves between the unknown biologically active agent and vehicle control, and if sufficiently similar, comparing the impedance base curve of the unknown biologically active agent to a library of signature time dependent response profiles (TCRPs) obtained from a multitude of known biologically active agents optionally obtained by the method as set forth above; and if sufficiently similar, identifying the unknown biologically active agent as affecting a same oncogene addicted pathway similarly as the corresponding known biologically active agent; or if not sufficiently similar, catagorzing the unknown biologically active agent as a new signature time dependent response profile (TCRP) in the library.

In a related approach a method of identifying whether a biological agent affects an oncogene addicted pathway is provided, which includes: providing a system for monitoring cell-substrate impedance comprising a plurality of impedance monitoring wells; adding oncogene addicted cells comprising an active oncogene addicted pathway to at least two wells; monitoring impedance of the at least two wells over a time period to obtain impedance values and optionally determining cell indices from the impedance values; introducing at least one known biologically active agent known to affect the oncogene addicted pathway to one well and introducing an unknown biologically active agent suspected of affecting the oncogene affected pathway to another well, wherein the introductions occur after at least one impedance value for the corresponding well is obtained; generating impedance-based curves from the impedance values or cell indicies from each well; comparing the impedance-based curves between the at least one known biologically active agent and the unknown biologically active agent, and if sufficiently similar, concluding the unknown biologically active agent affects a same oncogene addicted pathway similarly as the at least one known biologically active agent.

A variety of oncogene addicted cells may be used with the methods, including those selected from the group consisting of a cancer cell, optionally a lung cancer cell, a gastric cancer cell, a melanoma cell, an epidermoid cell, a colon cancer cell, a neuroblastoma cell, and a virus infected cell. Oncogene addicted cells can be those that overexpress an oncogene in an oncogene addicted pathway or can be isogenic cells that express an oncogene at a level similar to that of a natural cancer cell.

While the modulation of a variety of oncogene addicted pathways can be monitored, and distinguished from one another among these include a cMET pathway, an EGFR pathway, a PDGFR pathway, an ALK pathway, a P13K pathway, a serine/threonine kinase pathway, and a b-Raf pathway. As such, the methods are particularly useful when the at least one known biologically active agent is an inhibitor of a kinase selected from the group consisting of cMET, EGFR, PDGFR, ALK, P13K, a serine/threonine kinase, and b-Raf. Further analysis of the oncogene addicted pathway can be achieved when the at least one known biologically active agent and/or the unknown biologically active agent are provided in different concentrations to a same cell type in different wells to generate a dose response curve, to determine an EC50, or determine an IC50. In another related approach a method of generating a time dependent cellular response profile (TCRP) for the modulation of an oncogene addicted pathway through the use of a cell population overexpressing an oncogene and a known biologically active agent is provided. The method includes: providing a system for monitoring cell-substrate impedance comprising a plurality of impedance monitoring wells; adding a population of cells overexpressing an oncogene forming part of an oncogene addicted pathway to at least two wells and adding parental cells to at least two other wells; monitoring impedance of the at least four wells over a period of time to obtain impedance values and optionally determining cell indices from the impedance values; introducing at least one known biologically active agent which affects the expression of the oncogene to at least one well of cells overexpressing the oncogene and to at least one well of parental cells, and introducing a vehicle control to another well of cells overexpressing the oncogene and to another well of parental cells, wherein the introductions occur after at least one impedance value for the corresponding well is obtained; generating an impedance-based curve from the impedance values or cell indicies for each of the wells; comparing the impedance-based curves between wells having the cells overexpressing the oncogene to determine a time dependent response profile for cells overexpressing the oncogene and comparing the impedance-based curves between the wells having parental cells to determine a time dependent response profile for parental cells; comparing the time dependent cellular response profiles between cells overexpressing the oncogene and parental cells; and if significantly different, categorizing the cellular response profile in overexpressing cells as a signature profile for modulation of an oncogene or oncogene addicted pathway.

In still another related approach, a method of identifying unknown biologically active agents which target specific oncogene or oncogene addicted pathways is provided. The method includes: providing a system for monitoring cell-substrate impedance having a plurality of impedance monitoring wells; adding oncogene addicted cells (or cells overexpressing oncogenes or cells isogenically expressing oncogenes) to at least two wells; monitoring impedance of the at least two wells over a time period and optionally determining cell indices from impedance values; introducing at least one known biologically active agent which targets the oncogene to one well and at least one unknown biologically active agent to another well, wherein the introductions occur after at least one impedance value for the corresponding well is obtained; generating impedance-based curves from the impedance values from each well to obtain a TCRP for both the known and unknown biologically active agents; comparing the impedance-based TCRPs between the known biologically active agent and unknown biologically active agent and if similar the compound is considered a hit which may also target the oncogene or oncogene addicted pathway.

In still another approach, a method of identifying whether a biological agent affects an oncogene addicted pathway is provided, which includes: providing a system for monitoring cell-substrate impedance comprising a plurality of impedance monitoring wells; adding a population of cells overexpressing an oncogene forming part of an oncogene addicted pathway to at least two wells; monitoring impedance of the at least two wells over a time period to obtain impedance values and optionally determining cell indices from the impedance values; introducing a known biologically active agent known to affect the oncogene addicted pathway to one well and introducing an unknown biologically active agent suspected of affecting the oncogene addicted pathway to another well, wherein the introductions occur after at least one impedance value for the corresponding well is obtained; generating impedance-based curves from the impedance values or cell index curves from each well; comparing the impedance-based curves between the known biologically active agent and the unknown biologically active agent, and if sufficiently similar, concluding the unknown biologically active agent affects a same oncogene addicted pathway similarly to the known biologically active agent.

In view of the above, the oncogene addicted cell lines (or oncogene overexpressing cell lines or isogenic cell lines expressing oncogenes at level similar to those in natural cancer cells) express constitutively active oncogenes. In these cells, the oncogenes and their signal pathways are up-regulated in the absence of up-stream signals (e.g. its cognate ligands, activation by its regulatory partner). Inhibition of the oncogenes and their signal pathways will have both short-term and long-term effects on these cells. If the activity of an oncogene and its related signal pathways are linked to modulating cell adhesion, cytoskeleton, cell structure (including but not limited to cell membrane size, morphology or composition), cell-cell interactions, etc, the impedance-based TCRP are hypothesized to show a short-term difference between the oncogene addicted cells and non-oncogene addicted cells. Specifically, as shown in EXAMPLE 1, MET addicted cell lines responded to MET inhibition with a short-term increase in and a long-term decrease in Cell Index (CI). The short-term increase can be explained by the fact that inhibition of MET results in immediate morphological change, as exemplified by increased cell-cell contact (Christensen, et al Cancer Res 2003; 63:7345). Characterization of these measured short-term cell response on the RT-CES system show that the response is specific, robust, reproducible and comparable to other RTK cell-based assays, such as Western blotting and ELISA. The long-term decease in CI indicates the cytotoxic effect of MET inhibitors. This observation is in accordance with the cell viability assay, such as WST assay. The superiority of using RT-CES system is that automatic recording of a single well in 96-well plate can generate a wealth of knowledge that can only be obtained from many cell based assays that are time-consuming, labor intensity and expensive.

Therefore, the RT-CES system was used to screen a small diverse library of inhibitors and a collection of kinase inhibitors, enabling the identification of a specific and potent kinase inhibitor. This assay was also used to further characterize the hit by generating dose response curves. Compared to existing kinase assays, this assay does not suffer from interference from assay components, nor require expensive reagents, such as purified antibody or peptides. Furthermore, this assay platform provides high content information regarding the signaling pathways being activated. Since the readout is non-invasive and carried out on live cells, multiple treatments can be carried out in the same well with the same cells and can also be used in conjunction with existing endpoint assays such as ELISA. The ACEA RT-CES system therefore offers an alternative to or complements existing kinase assays, and can be used for both primary and secondary screens.

Stimulation of receptor tyrosine kinases such as EGF receptor, PDGF receptor, fibroblast growth factor (FGF) receptor, vascular endothelial growth factor (VEGF) receptor and c-Met receptor for hepatocyte growth factor with their cognate ligand leads to dramatic remodeling of the actin cytoskeleton. These receptor tyrosine kinases have also been linked to the progression of different kinds of cancers. Because the RT-CES system can detect transient changes in morphology and adhesive capacity of the cells, it can be used to monitor growth factor-induced remodeling of actin cytoskeleton in adherent mammalian cells through their associated receptor tyrosine kinase. The RT-CES assay provides a convenient label-free, real-time and quantitative method for functional activation of the receptor tyrosine kinases. However, this stimulation of RTK method requires medium exchange (from normal growth medium to serum free medium) and ligand stimulation. For mutant RTK, this method generated unreliable IC50 of control inhibitors (see discussion in EXAMPLE 4 and summary of the IC50 in Table 2)

As for the oncogene addicted cell line (or oncogene overexpressing cells or isogenic cell lines expressing oncogenes), a particular protein (oncogene) is usually up-regulated even in the absence of up-stream signals (e.g. its cognate ligands, activation by its regulatory partner), therefore upon inhibition of this oncogene, cells normally undergo some morphological changes then subsequent cell death, both of which can be detected by RT-CES system.

The steps involved in using the RT-CES system for measurement of changes in cell adhesion, cytoskeleton, cell structure (including but not limited to cell membrane size, morphology or composition), cell-cell interactions, etc, associated with oncogene inhibition may include: seeding adherent mammalian cells which are endogenously expressing the appropriate oncogene in the wells of E-plate, alternatively, the oncogene of interest can be transiently or stably expressed in an appropriate cell line and then seeded in E-plate, monitor the growth and proliferation of the cells using the RT-CES system for a period of time, adding known or unknown compounds to the cells, monitoring the changes in Cell Index (CI) using RT-CES system. Depending on the oncogenes and cell lines used, a medium exchange step may or may not needed prior to compound addition.

Accordingly, the method of the present invention is to devise a cell-based assay method for assaying oncogene activity and also for screening for inhibitors of the oncogene of interest. The method is based on quantification in real time of cytoskeletal changes and/or morphological change and/or cell adhesion change that arise as inhibition of the constitutively active oncogenes of cells growing in the E-Plates. Because the electronic assay readout relies on cytoskeletal dynamics and/or cell morphology and/or cell adhesion property which are intrinsic cell responses to inhibition of the constitutively active oncogenes in short term, and because the electronic assay readout also relies on viable cell numbers which are intrinsic cell responses to inhibition of the its driven oncogenes in long term, it is more advantageous compared to using typical endpoint assays to screen for inhibitors using oncogene addicted cell lines.

In one example of the above method, a compound may be identified as a factor capable of interacting with oncogene if a significant change is observed between the change in impedance or cell index of a compound well in comparison to the change in impedance or cell index of a control well. Here both compound well and control well have the same test cells expressing an oncogene. The compound is added to the compound well, a known compound is added to positive control well, whilst a vehicle control is added to the negative control well. For the compound well, the change in impedance or cell index refer to the change occurred after adding the compound. For the control wells, the change in impedance or cell index refer to the change occurred after adding the vehicle control. As a nonlimiting example, a compound may be identified as a factor capable of interacting with this concogene if the comparison indicates a significant change including an increase or a decrease in impedance or cell index of the compound well after the compound addition to the test cells expressing the oncogene relative to the negative control well and if the comparison indicates a similar kinetic profile including an increase and decease in impedance or cell index of the compound well after the compound addition to the test cells expressing the oncogene relative to the positive control well.

Method of Validating a Molecular Target Involved in the Kinase Signaling Pathway The intracellular signaling pathway that is stimulated by engagement of the kinases by their cognate ligand or led by constitutively activation of the oncogenic kinase result not only the activation of the kinase but also activation of key downstream targets such as kinases, phosphatases and phospholipases amongst others which lend themselves as key potential targets for pharmaceutical drug discovery. However, prior to screening for potential inhibitors of these target proteins and enzymes, the target proteins and enzymes must be validated to ascertain that they can interfere with signaling pathways. This can be achieved either by introducing into cells by transfection, electroporation or viral infection the DNA encoding for the dominant negative versions of these proteins, genetic knockouts or siRNA that target and reduce the expression of these proteins. Also, specific chemical and protein inhibitors of the target proteins or enzymes may also be introduced to the cells to assess target validation. Once this has been achieved, then the cell-electrode impedance measurement method can be used to assess the effect of these key proteins on receptor-mediated signaling.

As an example (FIG. 32) an assay may be performed using the following procedure: introducing into cells either the DNA for the dominant negative version of the protein, a genetic knockout or siRNA targeting the protein of interest by various methods known to those skilled in the biological arts, transferring the cells to the wells of E-Plates, and assessing the effect of interfering agents in one or two ways. The cells were treated with inhibitor targeted the kinase of interest and the cellular response monitored by the RT-CES system. If the target protein participate in the signaling pathway resulting the cell morphology changes, then its abrogation by the methods described above is expected to either reduce or completely block inhibitor mediated cytoskeletal changes (and/or morphological changes), which can be measured and monitored by cell-electrode impedance sensing.

EXAMPLES

Example 1

Met Addictive Cell Lines Show Characteristic Impedance-based Time-dependent Cell Response Profiles (TCRP) to Met Inhibition

Cell lines. Human lung cancer cell line H1993 and human gastric cancer GTL-16 overexpress cMET and are Met addicted cell lines. human melanoma cell line SK-MEL-28, human colon cancer cell line colo205, rat glioma cell line C6 are not addicted to cMET. These cell lines were seeded into wells of 96 well E-Plate devices (Roche applied sciences) with an initial seeding density of 5000 cells per well and were pre-incubated in incubator under standard cell culture condition for about 24 hours. PF02341006 and ACEA348 (Met inhibitor) and other kinase inhibitors were added to the cells at different concentrations. The time-dependent cell response profiles (TCRP) were monitored prior to and after the compound addition using the xCelligence system (ACEA Biosciences/Roche applied sciences).

Figure 1:
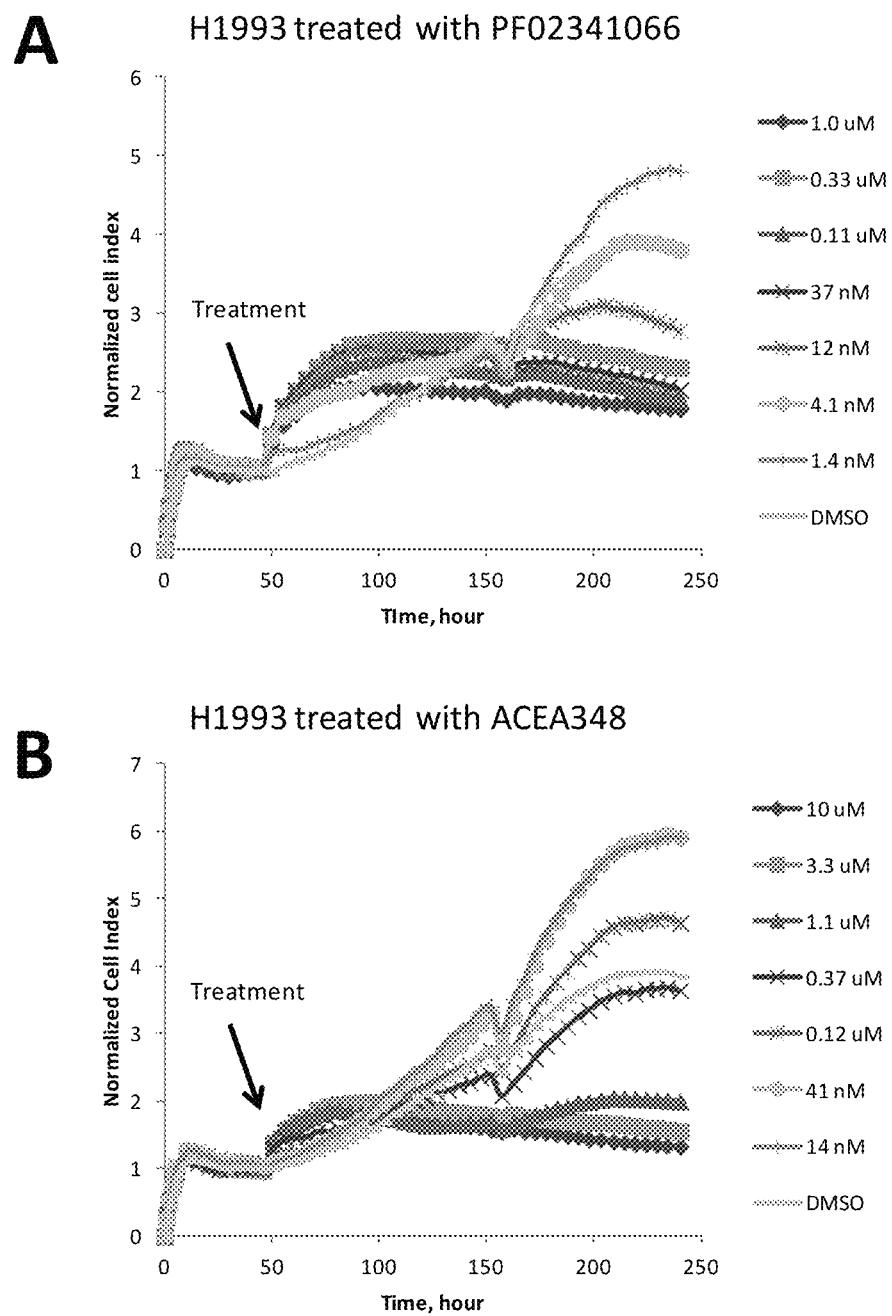
FIG. 1 shows impedance-based time-dependent cellular profiles (TCRPs) of H1993 in response to c-MET inhibitors on xCelligence system (Roche/ACEA). The TCRP was continuously recorded every 15 minutes for over 240 hours. The cell index was normalized at time of compound addition. (A) At the indicated time point of treatment, increasing concentrations of PF02341066 (from 0 to 1 uM) were added to the cells and the cell response was monitored. PF02341066 led to a dose-dependent short-term increase and long-term decrease in Cell Index (CI). (B) At the indicated time point of treatment (arrow), increasing concentrations of ACEA348 (from 0 to 10 uM) were added to the cells and the cell response was monitored. ACEA348 led to a dose-dependent short-term increase and long-term decrease in Cell Index (CI).
Figure 2:
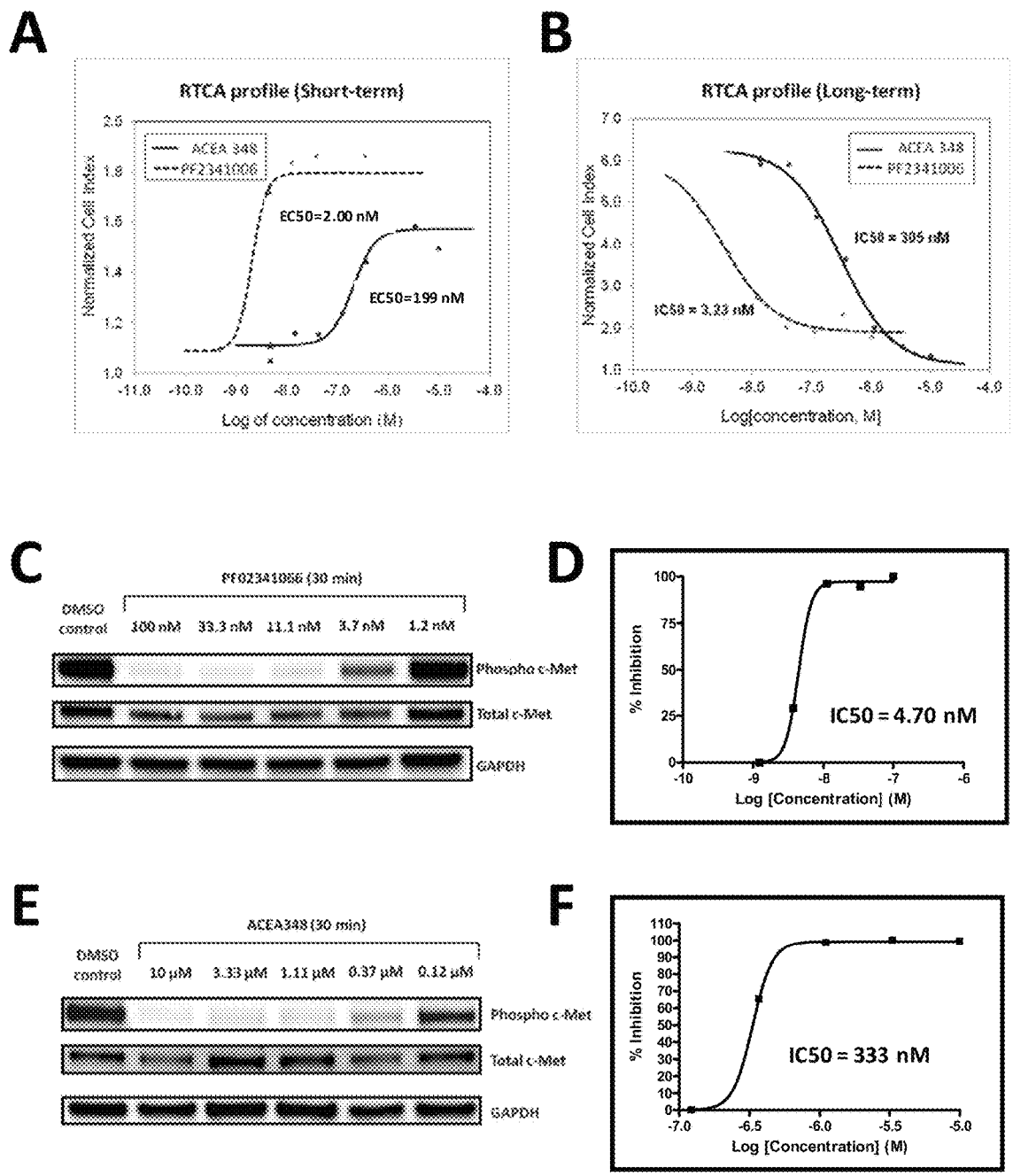
FIG. 2 compares the EC50/IC50 of PF02341066 and ACEA348 derived from impedance-based TCRP to those derived from Western analyses. (A) PF02341066 and ACEA348 led to a dose-dependent short-term increase in Cell Index (CI). Plotting the short-term (10 hours post compound treatment) CI versus the corresponding log concentration allows for calculation of the EC50 of PF02341066 and ACEA348 for c-MET. (B) PF02341066 and ACEA348 led to a dose-dependent long-term decrease in Cell Index (CI). Plotting the Long-term (200 hours post compound treatment) CI versus the corresponding log concentration allows for calculation of the IC50 of PF02341066 and ACEA348 for c-MET. (C) Effect of PF02341066 on c-MET phosphorylation in H1993 cells. Cells were treated with PF02341066 (0-100 nM) for 30 min. (D) The phospho-c-MET band for each PF02341066 treatment was quantified and its relative intensity (% inhibition) to that for DMSO control was plotted against the corresponding log concentration. IC50 was calculated based on curve fitting software (GraphPad Prism4). (E) Effect of ACEA348 on c-MET phosphorylation in H1993 cells. Cells were treated with ACEA348 (0-10 uM) for 30 min. (F) The phospho-c-MET band for each ACEA348 treatment was quantified and it relative intensity (% inhibition) to that for DMSO control was plotted against the corresponding log concentration. IC50 was calculated based on curve fitting software (GraphPad Prism4).
Figure 4:
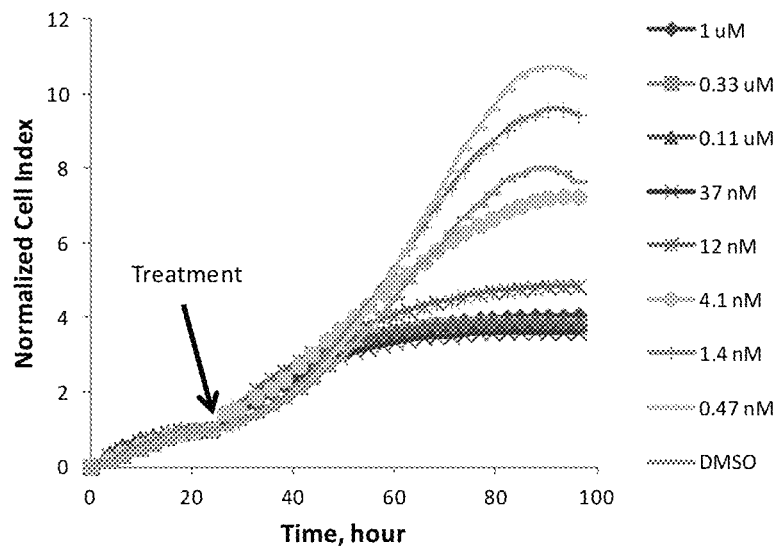
FIG. 4 shows impedance-based time-dependent cellular profiles (TCRPs) of GTL-16 in response to c-MET inhibitors on xCelligence system (Roche/ACEA). The TCRP was continuously recorded every 15 minutes for over 96 hours. The cell index was normalized at time of compound addition. (A) At the indicated time point of treatment, increasing concentrations of PF02341066 (from 0 to 1 uM) were added to the cells and the cell response was monitored. PF02341066 led to a dose-dependent short-term increase long-term decrease in Cell Index (CI). (B) At the indicated time point of treatment, increasing concentrations of ACEA348 (from 0 to 10 uM) were added to the cells and the cell response was monitored. ACEA348 led to a dose-dependent short-term increase and long-term decrease in Cell Index (CI).
Figure 4:
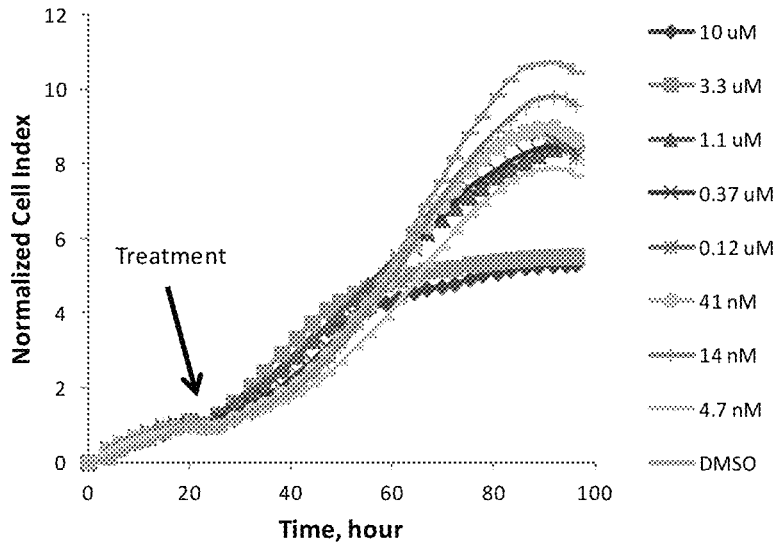
Figure 5:
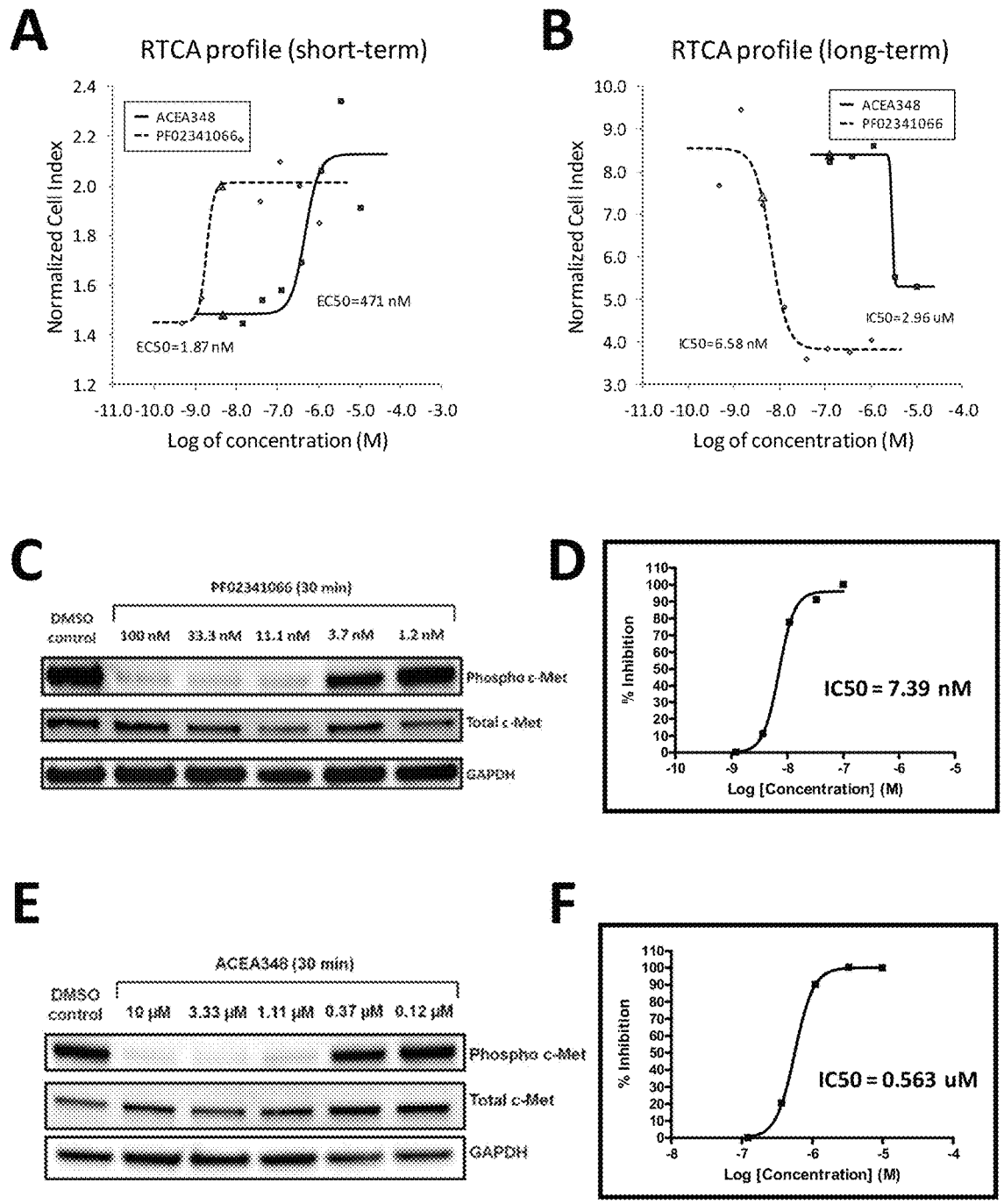
FIG. 5 compares the EC50/IC50 of PF02341066 and ACEA348 derived from impedance-based TCRP to those derived from Western analyses. (A) PF02341066 and ACEA348 led to a dose-dependent and short-term increase in Cell Index (CI). Plotting the short-term (10 hours post compound treatment) CI versus the corresponding log concentration allows for calculation of the EC50 of PF02341066 and ACEA348 for c-MET. (B) PF02341066 and ACEA348 led to a dose-dependent and long-term decrease in Cell Index (CI). Plotting the Long-term (72 hours post compound treatment) CI versus the corresponding log concentration allows for calculation of the IC50 of PF02341066 and ACEA348 for c-MET. (C) Effect of PF02341066 on c-MET phosphorylation in GTL-16 cells. Cells were treated with PF02341066 (0-100 nM) for 30 min. (D) The phospho-c-MET band for each PF02341066 treatment was quantified and its relative intensity (% inhibition) to that for DMSO control was plotted against the corresponding log concentration. IC50 was calculated based on curve fitting software (GraphPad Prism4). (E) Effect of ACEA348 on c-MET phosphorylation in GTL-16 cells. Cells were treated with ACEA348 (0-10 uM) for 30 min. (F) The phospho-c-MET band for each ACEA348 treatment was quantified and its relative intensity (% inhibition) to that for DMSO control was plotted against the corresponding log concentration. IC50 was calculated based on curve fitting software (GraphPad Prism4).
Figure 6:
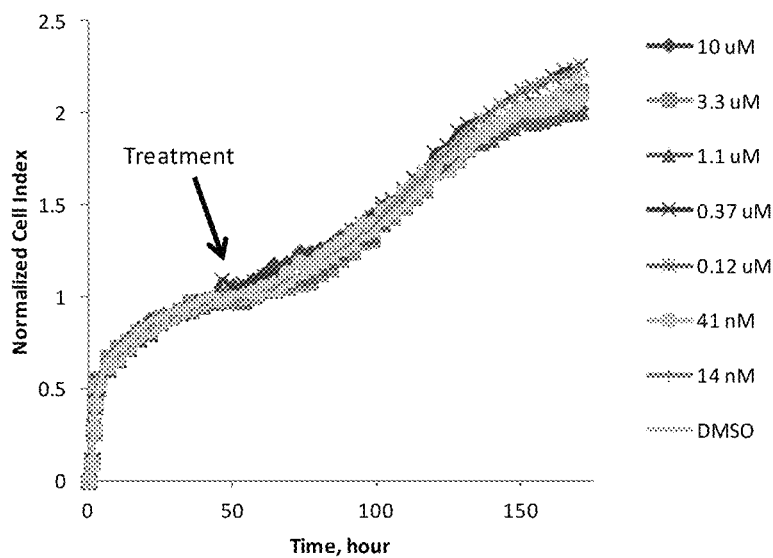
FIG. 6 shows impedance-based time-dependent cellular profiles (TCRPs) of SKMEL28 in response to c-MET inhibitors on xCelligence system (Roche/ACEA). The TCRP was continuously recorded every 15 minutes for over 170 hours. The cell index was normalized at time of compound addition. At the indicated time point of treatment (arrow), increasing concentrations of (A) ACEA348 (from 0 to 10 uM) and (B) PF02341066 (from 0 to 1 uM) were added to the cells and the cell response was monitored.
Figure 6:
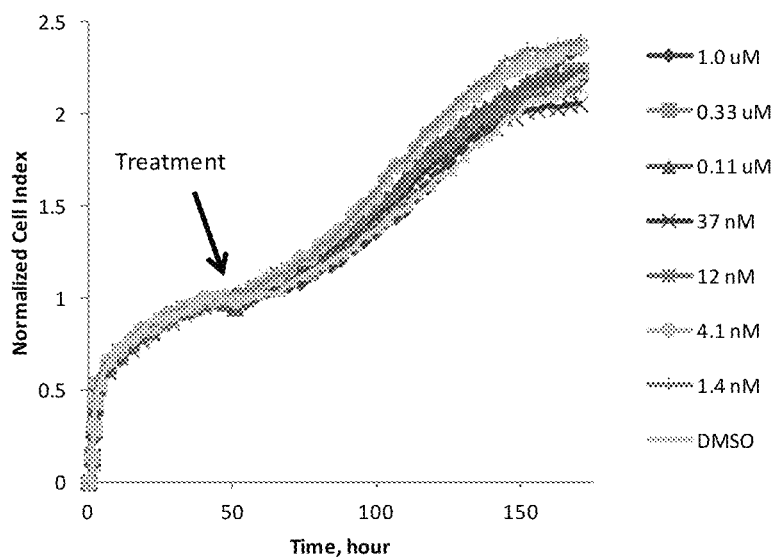
Figure 7:
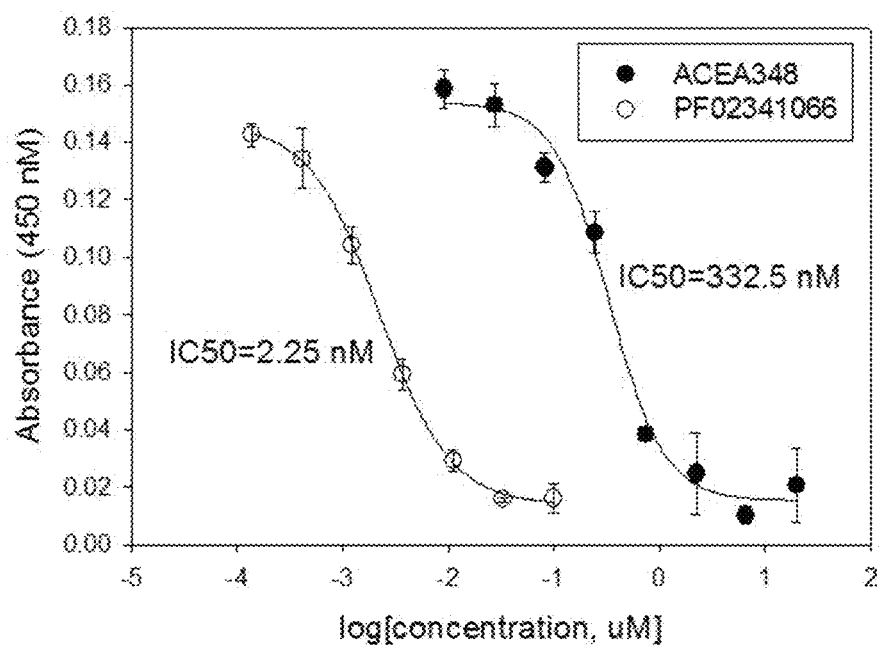
FIG. 7 shows the effect of PF02341066 and ACEA348 on the total phospho-c-MET (upon HGF stimulation) in A549 cells. The compounds were incubated with the cells (25,000 cells/well in 96-well plate) in serum-free medium for 2 hours, and then stimulated with 100 ng/mL HGF for 30 minutes. The cell lysates were used in the ELISA assay by following manufacture recommended protocol (R&D system). Plotting the total phospho-c-MET (30 minutes post compound treatment) versus the corresponding log concentration allows for calculation of the IC50 of PF02341066 and ACEA348 for c-MET.
Figure 10:
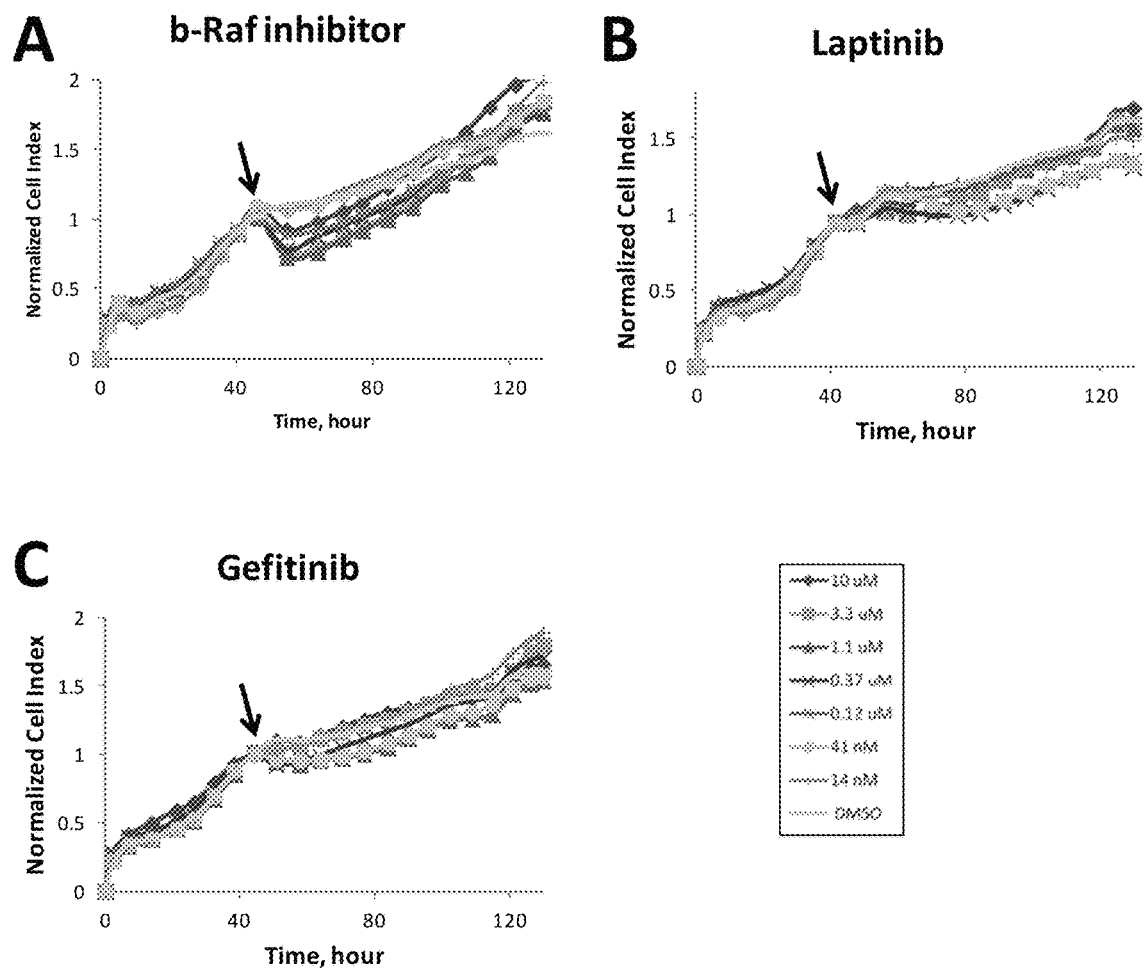
FIG. 10 shows impedance-based time-dependent cellular profiles (TCRPs) of C6 in response to a panel of protein kinase inhibitors on xCelligence system (Roche/ACEA). The TCRP was continuously recorded every 15 minutes for over 130 hours. The cell index (CI) was normalized at time of compound addition. At the indicated time point of treatment (arrow), increasing concentrations of (A) b-Raf inhibitor, EGFR inhibitor (B) Laptinib and (C) Gefitinib (from 0 to 10 uM) and (D) c-MET inhibitor (PF02341066) (from 0 to 1 uM) were added to the cells and the cell response was monitored. These kinase inhibitors didn't show any short-term or long-term effect on the Cell Index (CI).
Figure 10:
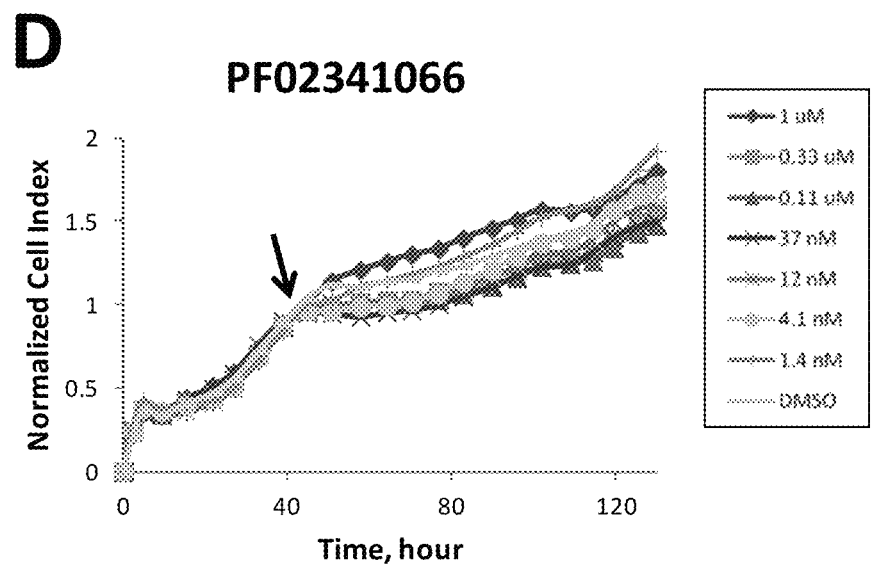

FIG. 1 and FIG. 4 show the TCRPs which are a representation of the normalized cell index as a function of time prior to and after compound addition. The Cell index was normalized against the cell index values at a time point just before compound addition. Upon Met inhibitor treatment, H1993, showed an initial increase (within 24 hr, short-term response) in the cell index followed by a steady decrease (72-120 hr, long-term response) in the cell index. As negative controls, non-Met addicted SK-MEL-28 (FIG. 6), C6 (FIG. 10D) and colo205 (FIG. 19E) did not respond to Met inhibition. Clearly, upon the treatment of Met inhibitor, Met addicted cells H1993 and GTL-16 displayed unique TCRP (initial increase in cell index within 24 hrs and followed by a steady decrease in longer term of 72-120 hrs) with relative to vehicle control (i.e. steady increase in cell index until plateau). EC50 and IC50 of the Met inhibitor can be derived from the CI versus the corresponding log concentration of the inhibitor. Plotting the short-term (10 hours post compound treatment) CI versus the corresponding log concentration allows for calculation of the EC50 of PF02341066 and ACEA348 for c-MET (FIG. 2A and FIG. 5A). The EC50 is 2.00 nM and 199 nM for PF2341066 and ACEA348, respectively in H1993. The EC50 is 1.87 nM and 471 nM for PF2341066 and ACEA348, respectively in GTL-16. Plotting the Long-term (200 hours post compound treatment) CI versus the corresponding log concentration allows for calculation of the IC50 of PF02341066 and ACEA348 for c-MET (FIG. 2B and FIG. 5B). The IC50 is 3.23 nM and 305 nM for PF2341066 and ACEA348, respectively in H1993. The IC50 is 6.58 nM and 2.96 uM for PF2341066 and ACEA348, respectively in GTL-16. The IC50s can also be derived from the effect of these inhibitors on Met phosphorylation in the corresponding cell lines (FIGS. 2C-F and FIGS. 5C-F). In H1993, the calculated IC50 is 4.70 nM and 333 nM for PF2341066 and ACEA348, respectively. In GTL-16, the calculated IC50 is 7.39 nM and 563 nM for PF2341066 and ACEA348, respectively. In addition, we also evaluated the efficacy of these two Met inhibitors on phospho-Met inhibition in A549 stimulated with HGF. Plotting the total phospho-c-MET (30 minutes post compound treatment) versus the corresponding log concentration allows for calculation of the IC50 of PF02341066 and ACEA348 for c-MET (FIG. 7). The IC50 derived from this ELISA assay is 2.25 nM and 333 nM for PF2341066 and ACEA348, respectively. Overall, the EC50/IC50 derived from TCRP and the IC50 derived from Western/ELISA correlated very well (See Table 1). This is indicative that the TCRP upon Met inhibitory addition is a function of phospho-Met inhibition, and that this specific TCRP pattern can be used to identify unknown cMet inhibitor in a screen setting or to elucidate mechanism of action of an known/unknown compound.

TABLE 1

|  | H1993 | | | GTL-16 | | | A549 |
|---|---|---|---|---|---|---|---|
|  | TCRP | | Western | TCRP | | Western | ELISA |
|  | EC50 | IC50 | IC50 | EC50 | IC50 | IC50 | IC50 |
| PF02341066 | 2.00 nM | 1.87 nM | 4.70 nM | 199 nM | 471 nM | 7.39 nM | 2.25 nM |
| ACEA348 | 3.23 nM | 305 nM | 333 nM | 6.58 nM | 2.96 uM | 563 nM | 333 nM |

Figure 3:
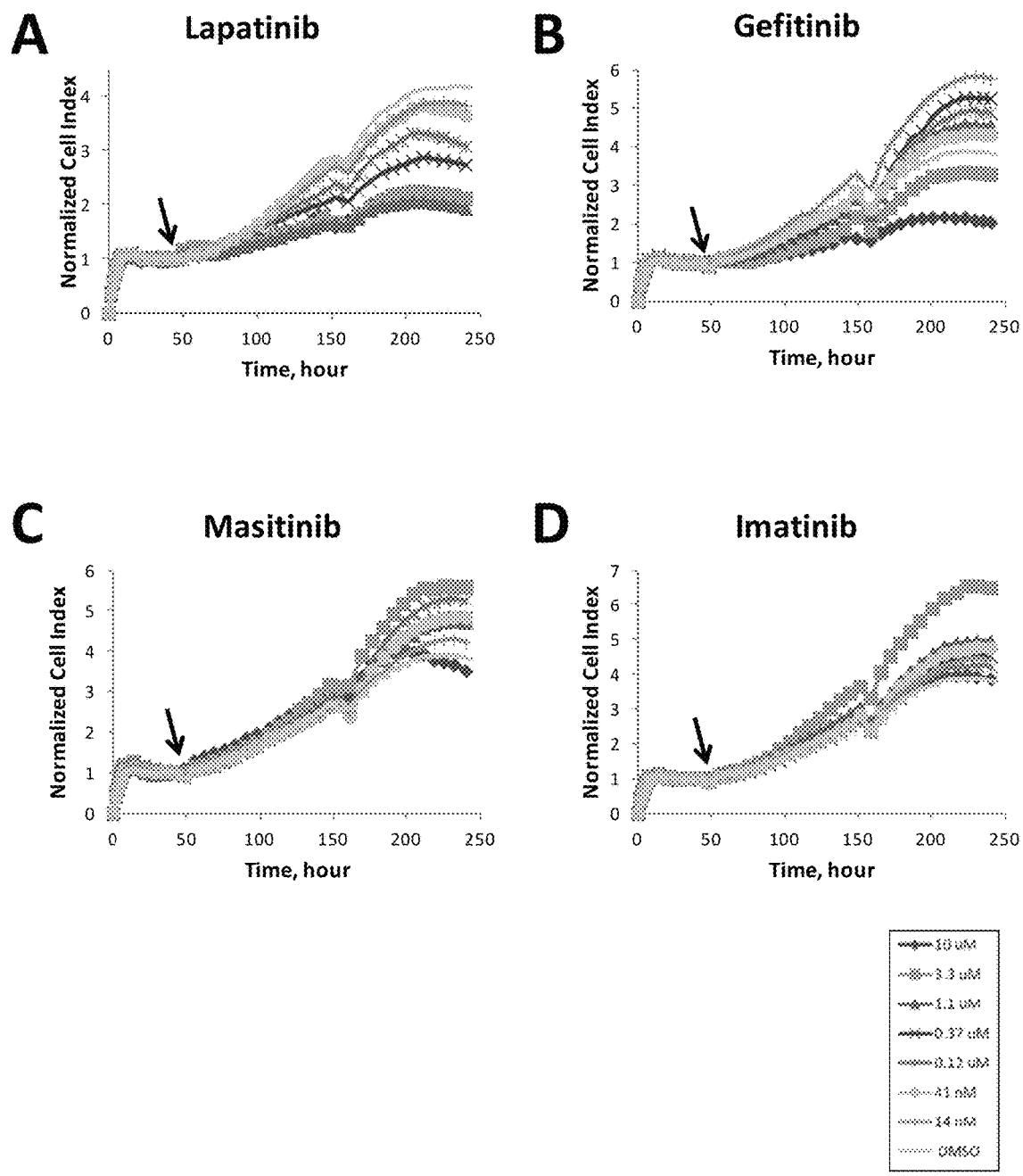
FIG. 3 shows impedance-based time-dependent cellular profiles (TCRPs) of H1993 in response to a panel of protein kinase inhibitors on xCelligence system (Roche/ACEA). The TCRP was continuously recorded every 15 minutes for over 240 hours. The cell index (CI) was normalized at time of compound addition. At the indicated time point of treatment (arrow), increasing concentrations of EGFR inhibitor (A) Lapatinib and (B) Gefitinib, PDGFR inhibitor (C) Masitinib and (D) Imatinib, (E) mTOR inhibitor (KU0063794), (F) PI3K-mTOR due kinase inhibitor (BEZ235), (G) inhibitor of upstream pathway of AKT (AKT inhibitor IV), (H) AKT1/2/3 inhibitor (AKT inhibitor VIII), (I) Rock inhibitor (GSK429286), (J) Rac family GTPase inhibitor (EHT1864), (K) MAPK/MEK inhibitor (PD98059), p38 MAPK inhibitor (L) SB203580 and (M) SB202190, (N) JNK inhibitor (SP600125), (O) MEK1/2 inhibitor (U0126) and (P) c-Raf1 inhibitor (GW5074) (from 0 to 10 uM) were added to the cells and the cell response was monitored.
Figure 3:
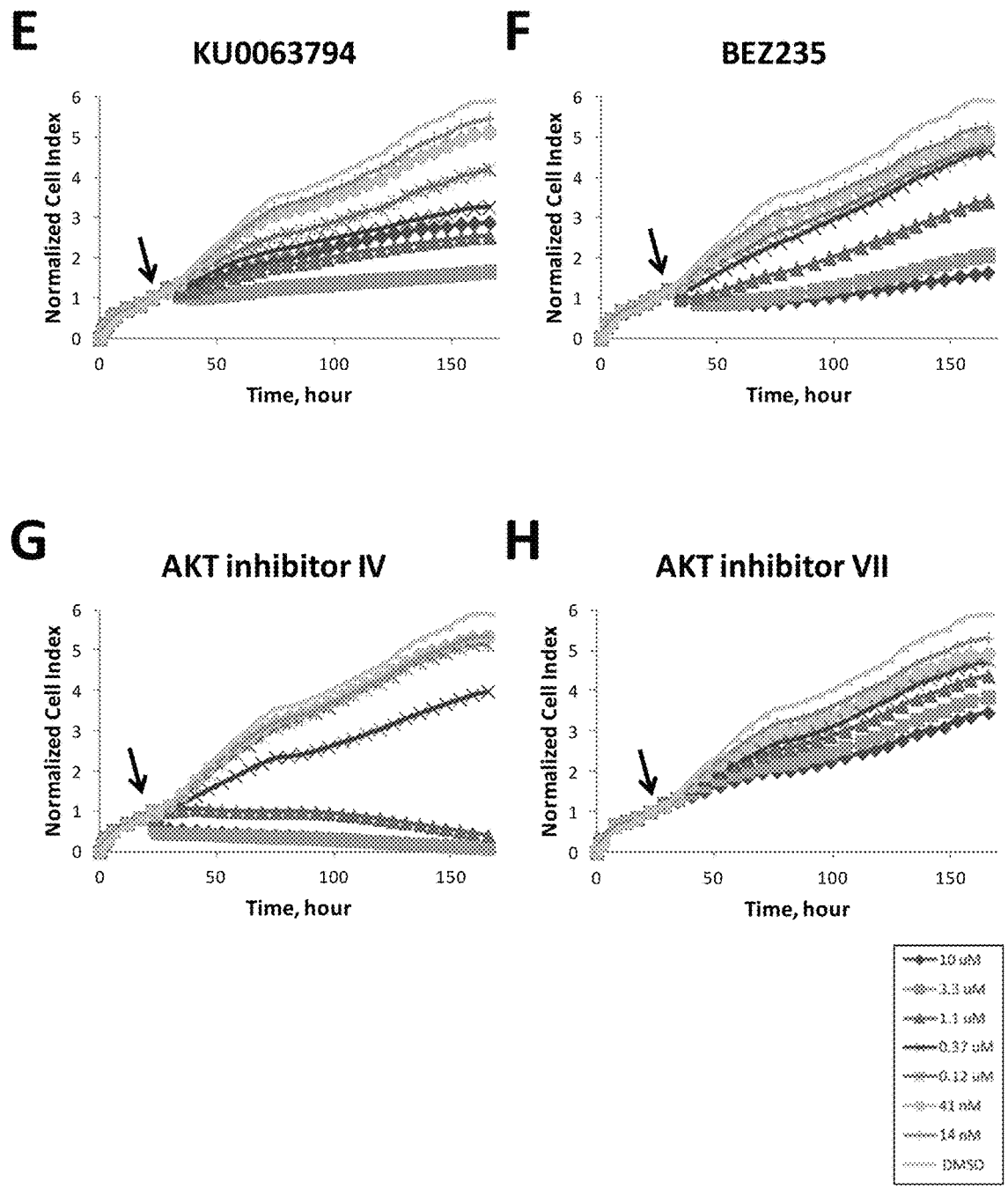
Figure 3:
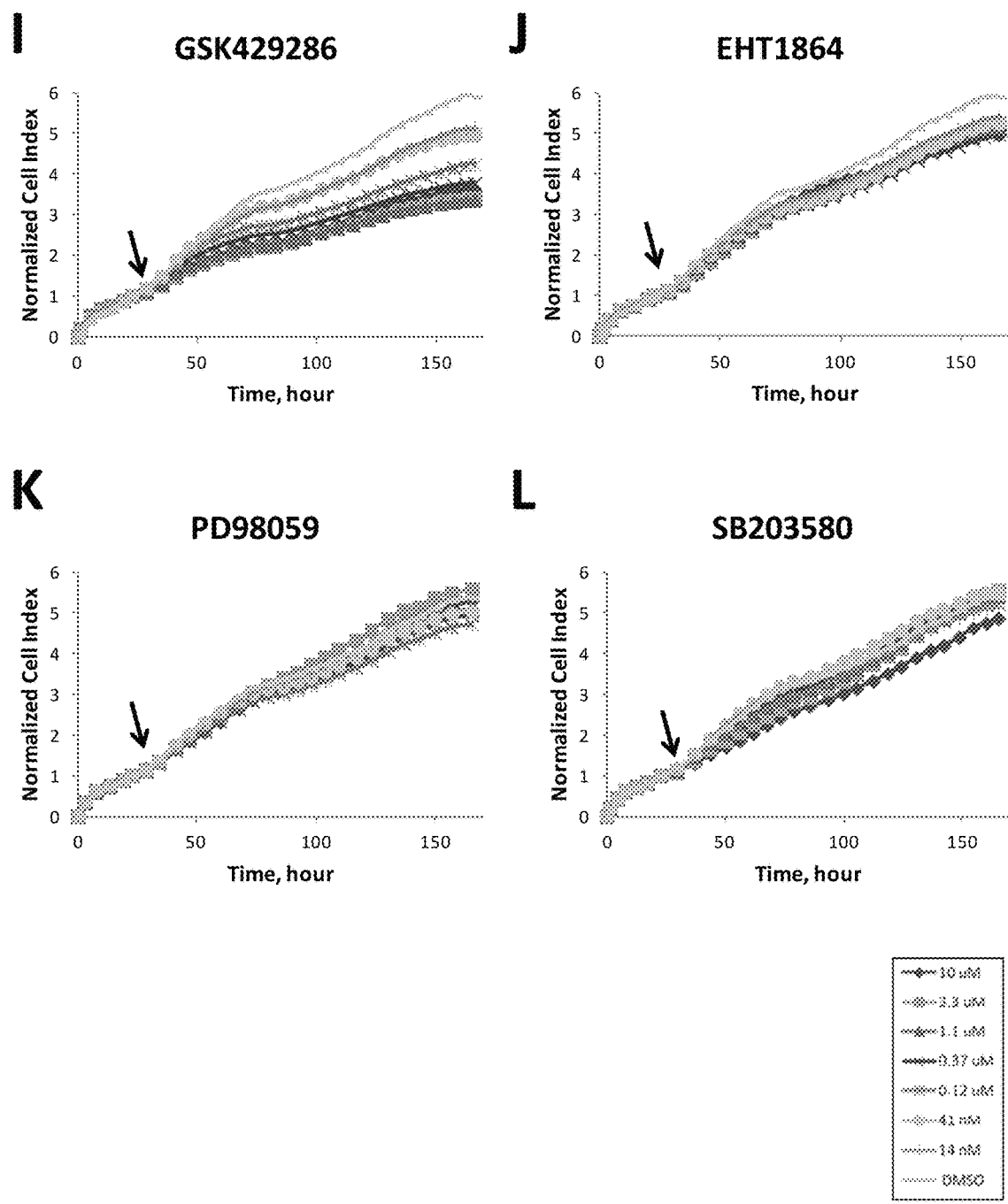
Figure 3:
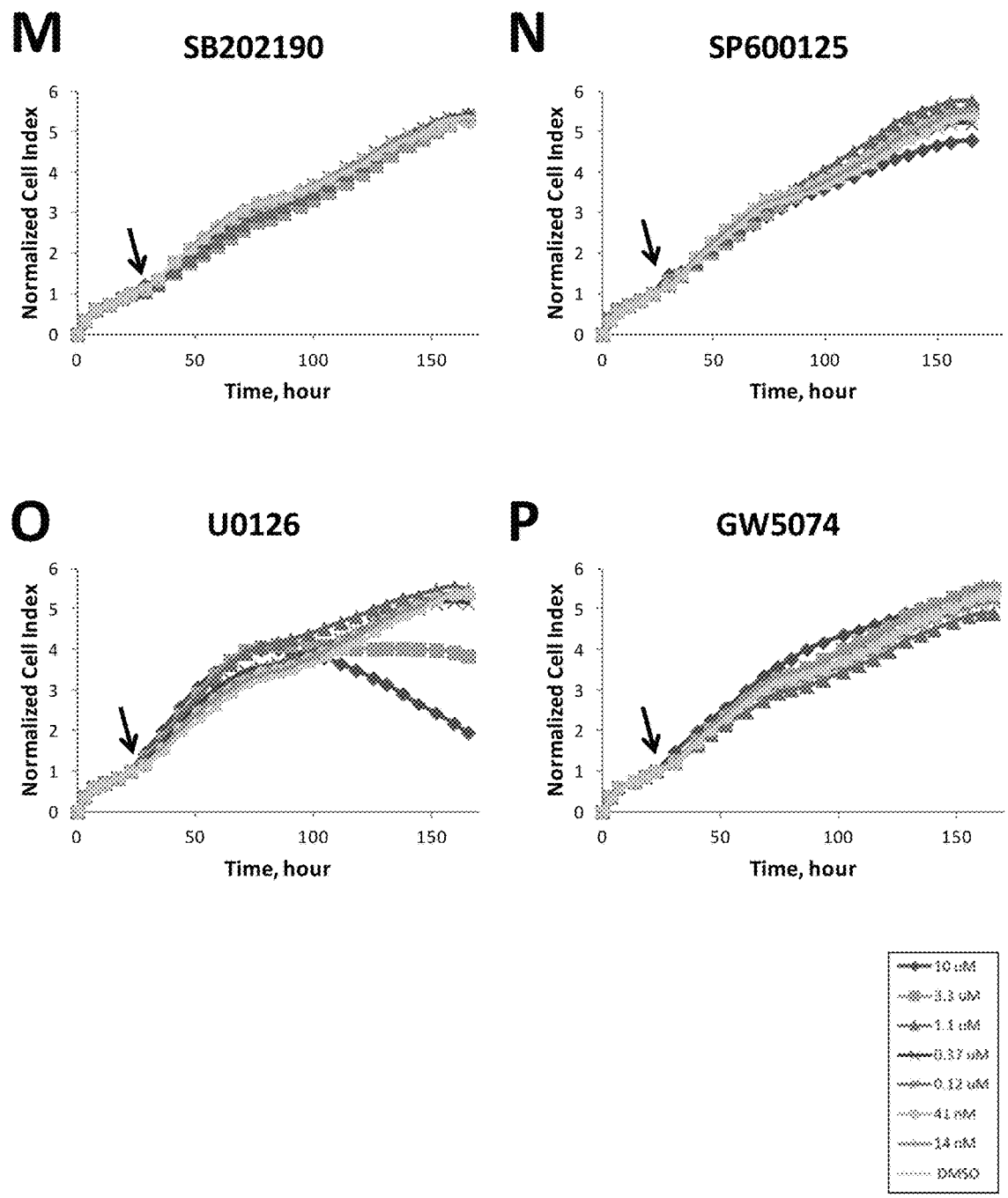

To confirm the specificity of the TCRP to Met inhibitor, we also tested the cell response to other control compounds in H1993 cell line (FIG. 3). Inhibitors used include EGFR inhibitor (lapatinib, gefitinib), PDGFR inhibitor (masitinib, imatinib), mTOR inhibitor (KU0063794), PI3K-mTOR due kinase inhibitor (BEZ235), inhibitor of upstream pathway of AKT (AKT inhibitor IV), AKT1/2/3 inhibitor (AKT inhibitor VIII), Rock inhibitor (GSK429286), Rac family GTPase inhibitor (EHT1864), MAPK/MEK inhibitor (PD98059), p38 MAPK inhibitor (SB203580, SB202190), JNK inhibitor (SP600125), MEK1/2 inhibitor (U0126) and c-Raf1 inhibitor (GW5074). None of these inhibitors induced a TCRP similar to PF2341006 (Met inhibitor). In a screen setting, a cluster analysis of the TCPR can easily separate these compounds from those inhibit cMet, resulting an easy identification of cMet (or cMet pathway) inhibitors. These results suggest that the observed TCRP induced by PF2341006 is specific to Met inhibition. Similarly, we have observed this specificity in GTL-16 (data not shown).

Example 2

PDGFR Addicted Cell Lines Show Characteristic Impedance-based Time-dependent Cell Response Profiles (TCRP) to PDGFR Inhibitors

Cell lines. Rat C6 glioma cell line is PDGFR addicted cell line.

Figure 8:
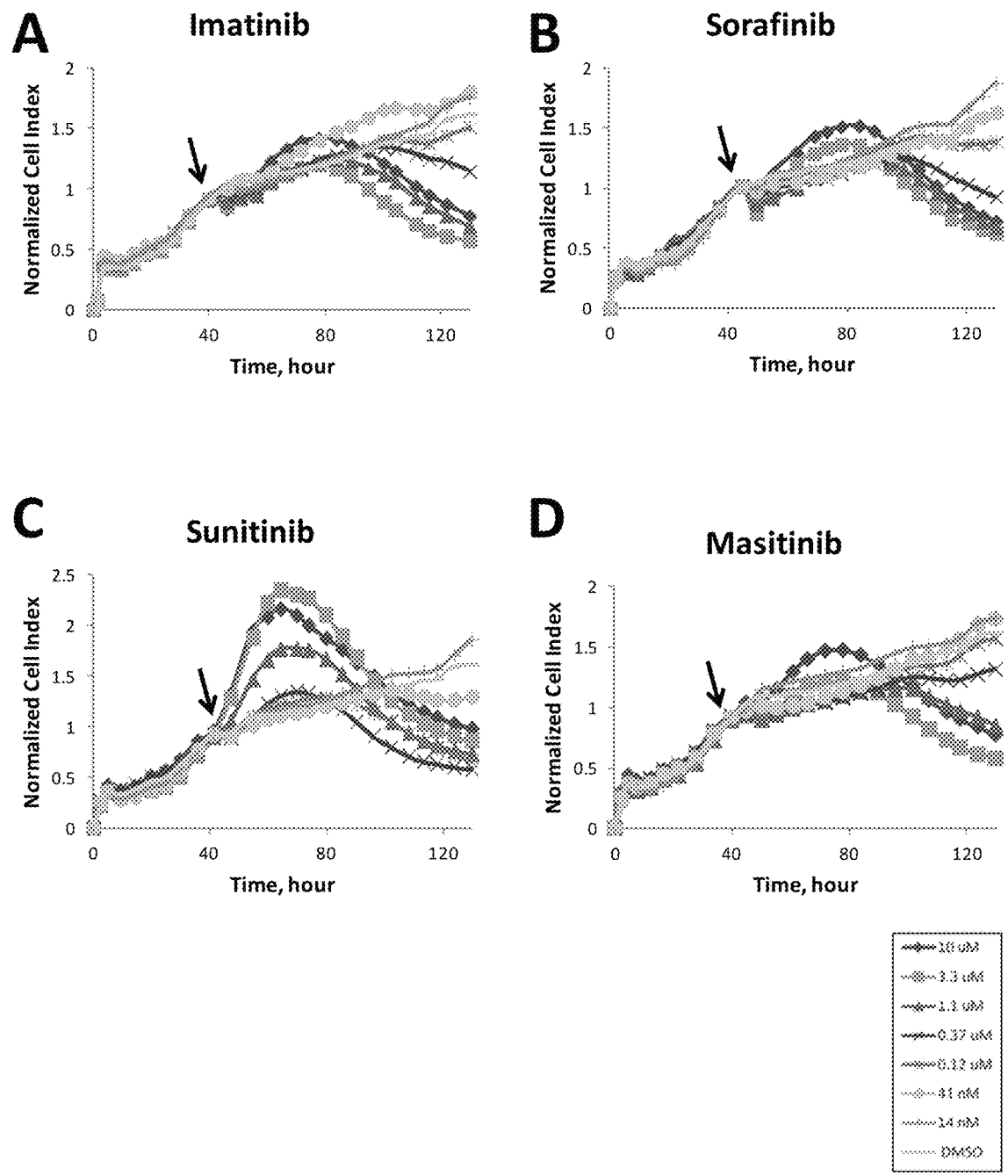
FIG. 8 shows impedance-based time-dependent cellular profiles (TCRPs) of C6 in response to PDGFR inhibitors on xCelligence system (Roche/ACEA). The TCRP was continuously recorded every 15 minutes for over 130 hours. The cell index (CI) was normalized at time of compound addition. At the indicated time point of treatment (arrow), increasing concentrations of PDGFR inhibitor (A) Imatinib, (B) Sorafinib, (C) Sunitinib and (D) Masitinib (from 0 to 10 uM) were added to the cells and the cell response was monitored. These PDGFR inhibitors led to a dose-dependent short-term increase (to a various degree) and long-term decrease in Cell Index (CI).
Figure 9:
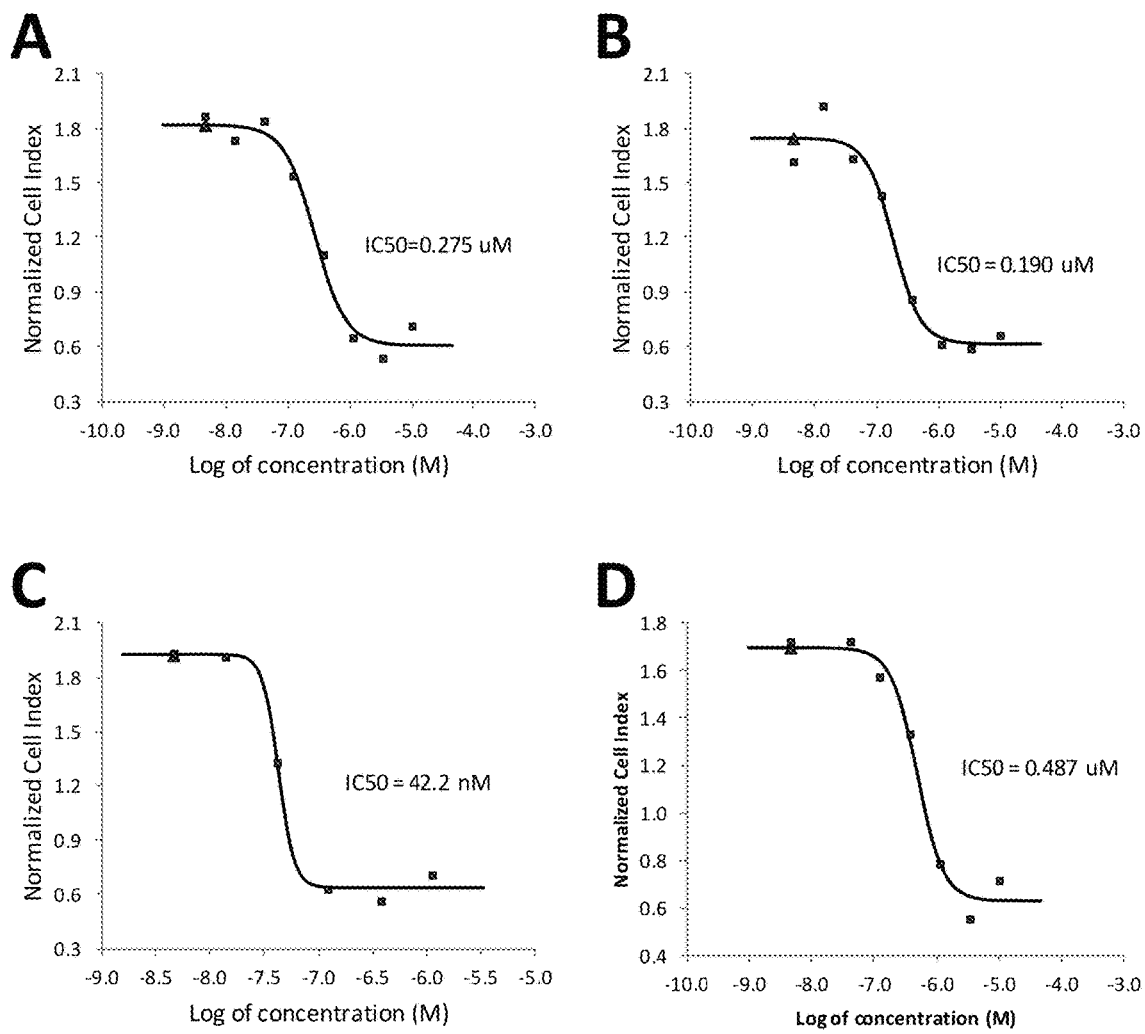
FIG. 9 IC50 of PDGFR derived from impedance-based TCRP. (A) Imatinib, (B) Sorafinib, (C) Sunitinib and (D) Masitinib leads to a dose-dependent long-term decrease in Cell Index (CI). Plotting the Long-term (96 hours post compound treatment) CI versus the corresponding log concentration allows for calculation of the IC50 of these compounds for PDGFR. IC50 was calculated based on curve fitting software (RTCA software).

C6 cells were seeded into wells of 96 well E-plate devices (ACEA Biosciences/Roche applied sciences) with an initial seeding density of 5000 cells per well and were pre-incubated in incubator under standard cell culture condition for about 24 hours. Kinase inhibitors including PDGFR inhibitors at different concentrations in DMSO were added into wells following the incubation period. The cell status was monitored prior to and after the compound addition using xCelligence system (Roche applied sciences). FIG. 8 shows the normalized cell index as a function of time prior to and after compound addition. The Cell index was normalized against the cell index values at a time point just before compound addition.

Upon PDGFR inhibitor treatment, C6 showed an initial increase (within 24 hr, short-term response) in the cell index followed by a steady decrease (72-120 hr, long-term response) in the cell index (FIG. 8A-D). PDGFR inhibitors tested include imatinib, sorafenib, sunitinib and mastitinib. IC50 of the PDGFR inhibitor can be derived from the CI versus the corresponding log concentration of the inhibitor. Plotting the Long-term (96 hours post compound treatment) CI versus the corresponding log concentration allows for calculation of the IC50 of imatinib, sorafenib, sunitinib and mastitinib (FIG. 9A-D). The IC50 is 0.275 uM, 0.190 uM, 42.2 nM and 0.487 uM for imatinib, sorafenib, sunitinib and mastitinib., respectively.

Figure 11:
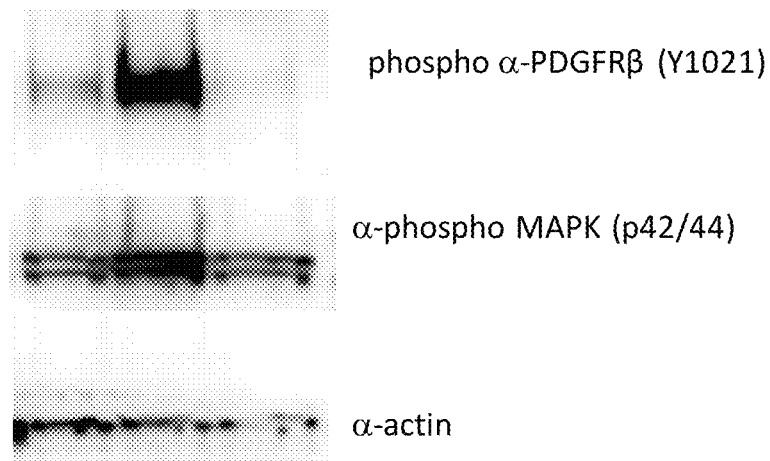
FIG. 11 shows the effect of imatinib on the signaling pathway of PDGFR. The level of phospho-PDGFRβ (Y1021) and phospho-MAPK in C6 treated with and without imatinib in the presence and absence of PDGF stimulation were shown. α-Actin was served as internal loading control.

To confirm the specificity of the time-dependent cell response profiles (TCRP) to PDGFR inhibitors, we also tested the TCRP in response to B-raf inhibitor (FIG. 10A) and two EGFR inhibitors (lapatinib and gefitinib) (FIGS. B-C) and Met inhibitor (PF02341066) (FIG. 10D) in C6 cell line. These inhibitors did not affect CI changes that are significantly different from the negative control (DMSO treated cells). These results indicate that the signature impedance-based TCRP observed for PDGFR inhibitors is specific and that this TCPR can be used for identifying PDGFR inhibitor or illustrating the mechanism of action (MOA) for an unknown compound. To confirm PDGFR inhibitor imatinib inhibits PDGFR signaling in C6 cells, both autophosphorylation of PDGFR and phosphorylation status of its downstream target MAPK were examined. The Western results show that Imatinib is effectively inhibited PDGFRβ autophosphorylation and down-regulated phospho-MAPK (FIG. 11).

Example 3

Monitoring Dose-dependent Functional Activation of PDGFRβ in Rat Basophilic (RBL2H3) Cells and Pharmacological Characterization by a Selective PDGFR Inhibitor Cell lines. RBL2H3-PDGFR is engineered rat basophilic cell line that expresses exogenous PDGFRβ. RBL2H3 is the parental cell line.

RBL2H3-PDGFR overexpressing PDGFRβ was constructed by Lenti viral transduction of RBL2H3. Both RBL2H3-PDGFR and RBL2H3 cells were seeded at 20,000 cells per well of 96-well E-plate (Roche/ACEA). The cells were continuously monitored using the xCelligence system (Roche/ACEA).

Figure 12:
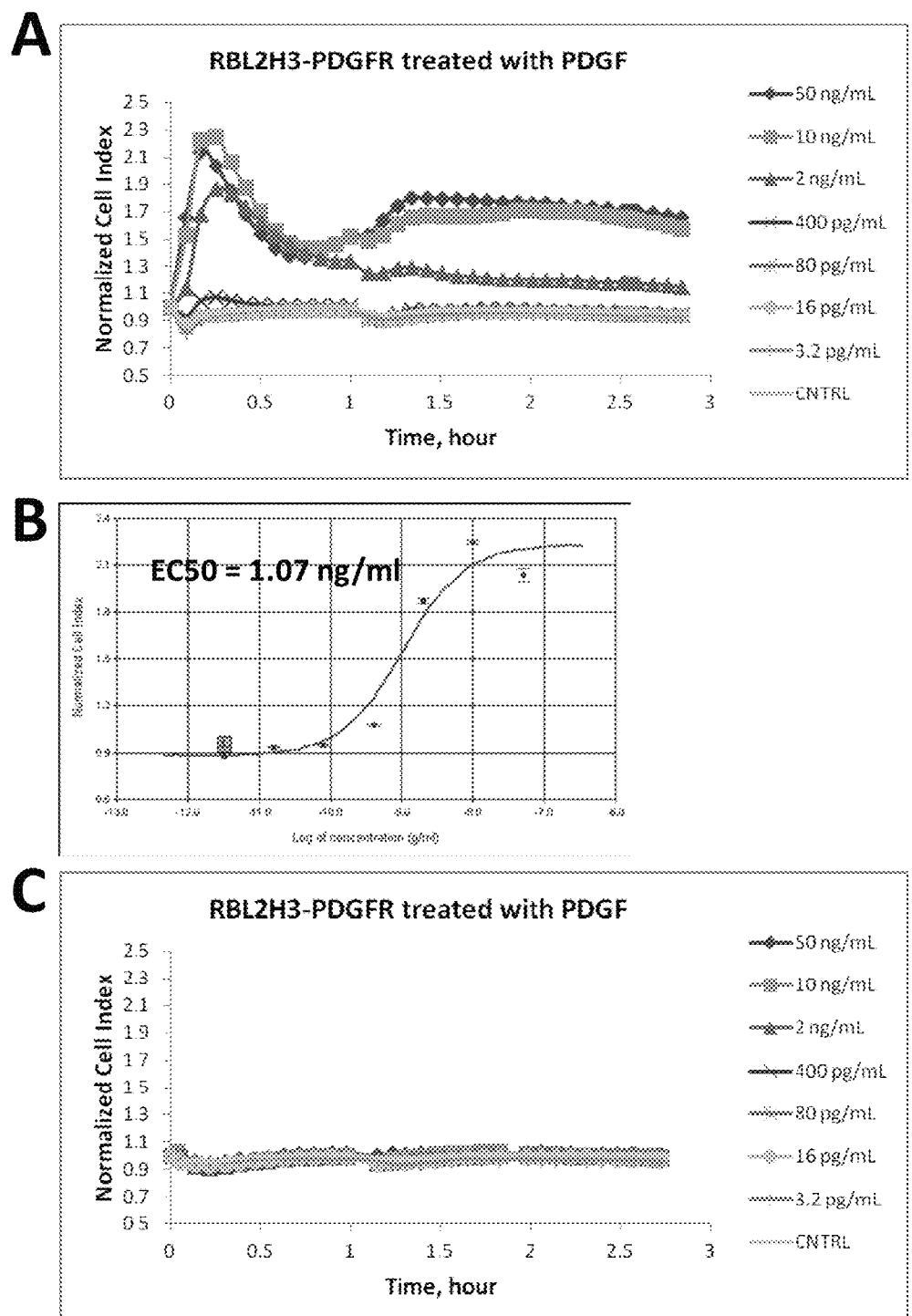
FIG. 12 shows the response of an engineered cell line, RBL-2H3 expressing PDGFRβ, to PDGF stimulation. RBL-2H3 PDGFRβ cells were seeded at 20,000 cells per well of 96-well E-plate (Roche/ACEA). The cells were continuously monitored using the xCelligence system (Roche/ACEA). Cells were serum starved for 2 hour, then stimulated by addition of PDGF BB (0-50 ng/ml) (A) RBL-2H3 PDGFRβ showed an impedance-based TCRP to PDGF stimulation. The cell index (CI) was normalized at time of compound addition. Time zero depicts the time point of treatment. (B) Plotting the peak normalized CI response versus the corresponding log concentration allows for calculation of the EC50 of PDGF acting on PDGFR in the engineered cell line. (C) The parental cell line, RBL-2H3, did not show any response to PDGF stimulation. The cell index (CI) was normalized at time of compound addition. Time zero depicts the time point of treatment.

FIG. 12 shows the response of an engineered cell line, RBL-2H3 expressing PDGFRβ, to PDGF stimulation. Cells were serum starved for 2 hour, then stimulated by addition of PDGF BB (0-50 ng/ml). RBL-2H3 PDGFR showed an impedance-based TCRP to PDGF stimulation. Plotting the peak normalized CI response versus the corresponding log concentration allows for calculation of the EC50 (1.07 ng.mL) of PDGF acting on PDGFR in the engineered cell line. This dose-dependent increase in the CI is specific to PDGFR activation, since the parental cell line, RBL-2H3, did not show any response to PDGF stimulation. These results indicate that the engineered RBL2H3-PDGFR cell line successfully expressed functional active PDGFRβ.

Figure 13:
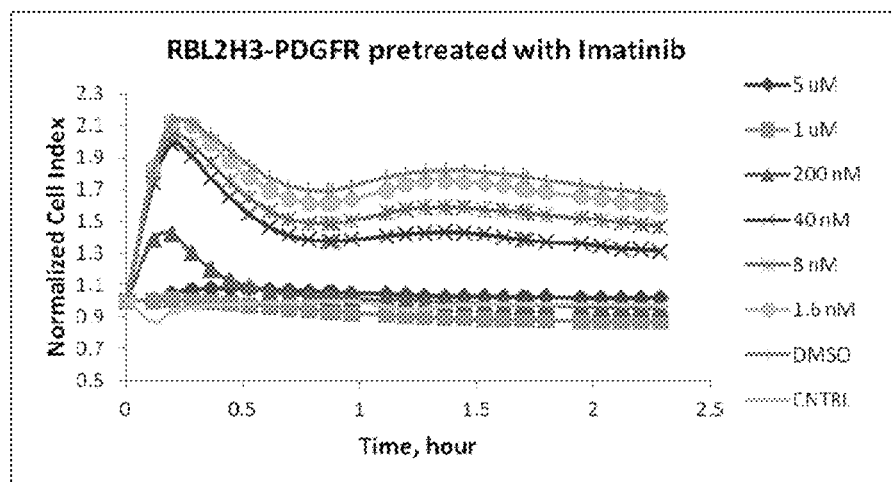
FIG. 13 depicts the pharmacological characterization of PDGF-stimulated CI increase in RBL-2H3 PDGFRβ, which is inhibited by the PDGFR inhibitor Imatinib. RBL-2H3 PDGFRβ cells were seeded at 20,000 cells per well of 96-well E-plate (Roche/ACEA). The cells were continuously monitored using the xCelligence system (Roche/ACEA). Cells were serum starved for 2 hour, Imatinib (0-5 uM) treated for 1 hour, then PDGF BB (10 ng/ml) stimulated. (A) RBL-2H3 PDGFRβ showed an impedance-based TCRP to PDGF inhibition. The cell index (CI) was normalized at time of compound addition. Time zero depicts the time point of treatment. (B) Plotting the peak normalized CI responses versus the corresponding log concentration allows for calculation of the IC50 of Imatinib acting on PDGFR in the engineered cell line. (C) The parental cell line, RBL-2H3, did not show any response to PDGF stimulation. The cell index (CI) was normalized at time of compound addition. Time zero depicts the time point of treatment.
Figure 13:
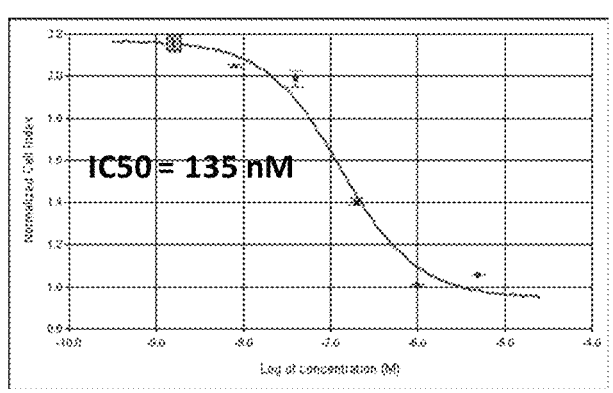
Figure 13:
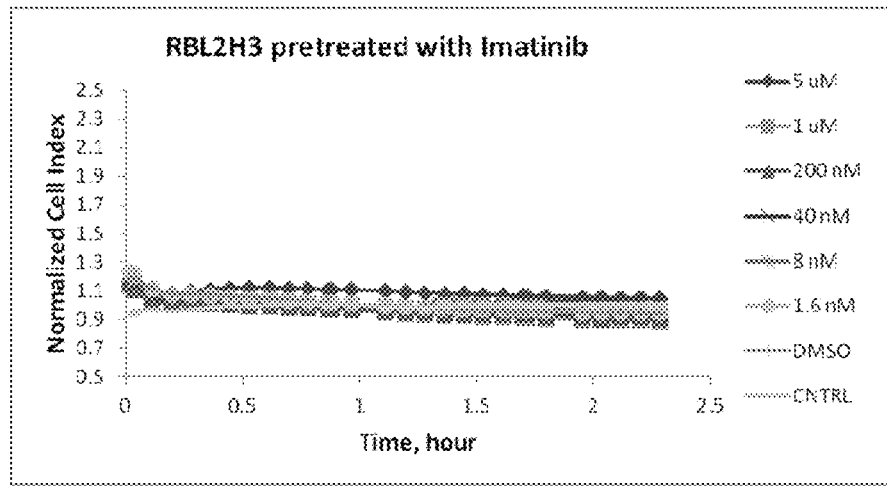

FIG. 13 depicts the pharmacological characterization of PDGF-stimulated CI increase in RBL-2H3 PDGFRβ, which is inhibited by the PDGFR inhibitor Imatinib. Cells were serum starved for 2 hour, Imatinib (0-5 uM) treated for 1 hour, then PDGF BB (10 ng/ml) stimulated. RBL-2H3 PDGFR showed an impedance-based TCRP to PDGF inhibition. Plotting the peak normalized CI responses versus the corresponding log concentration allows for calculation of the IC50 (135 nM) of Imatinib acting on PDGFR in the engineered cell line. This dose-dependent decease in the CI is specific to PDGFR inhibition. The parental cell line, RBL-2H3, did not show any response to either PDGF stimulation or PDGFR inhibition. These results indicate that the engineered RBL2H3-PDGFR cell line can give a robust, sensitive assay for PDGF inhibition using impedance-based technology. The IC50 (Imatinib) derived from this assay (135 nM) is comparable to that (275 nM) derived from using the PDGFR addicted C6 cell line (Example 2)

Example 4

EGFR Addicted Cell Lines Show Characteristic Impedance-based Time-dependent Cell Response Profiles (TORP) to EGFR Inhibitors Cell lines. Epidermoid carcinoma cell line A431 (overexpression of wild-type EFGR), lung cancer cell line H1975 (expressing mutant L858R/T790M EGFR) and lung cancer cell line HCC827 (expressing deletion mutant DelE746_A750 EGFR) are EGFR addictive cell line.

Figure 14:
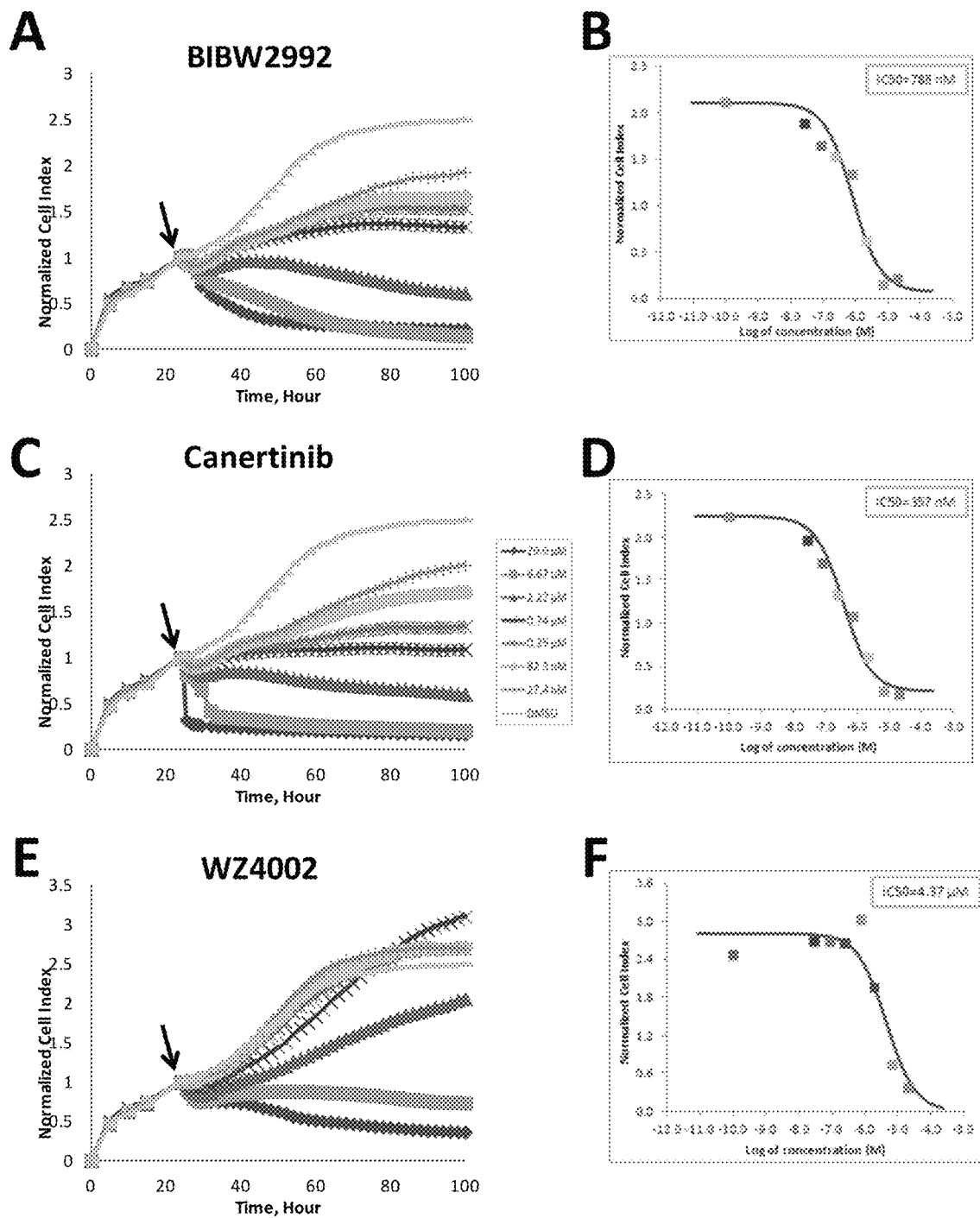
FIG. 14 shows impedance-based time-dependent cellular profiles (TCRPs) of A431 in response to EGFR inhibitors on xCelligence system (Roche/ACEA). The TCRP was continuously recorded every 15 minutes for over 100 hours. The cell index (CI) was normalized at time of compound addition. At the indicated time point of treatment (arrow), increasing concentrations of EGFR inhibitor (A) BIBW2992, (C) Canertinib and (E) WZ4002 (from 0 to 20 uM) were added to the cells and the cell response was monitored. These EGFR inhibitors led to a dose-dependent short-term and long-term decrease in Cell Index (CI). Plotting the Long-term (72 hours post compound treatment) CI versus the corresponding log concentration allows for calculation of the IC50 of these (B) BIBW2992, (D) Canertinib and (F) WZ4002 for wild-type EGFR.

A431 cells were seeded into wells of 96 well E-plate devices (Roche applied sciences) with an initial seeding density of 20,000 cells per well and were pre-incubated in incubator with DMEM medium plus 2% FBS over night. Then the known EGFR inhibitors including BIBW2992, Canertinib and WZ4002 in DMSO were added to cell at the desired concentration the cell response was monitored. DMSO at the same dose was served as solvent control. FIG. 14 shows impedance-based time-dependent cellular profiles (TCRPs) of A431 in response to EGFR inhibitors on xCelligence system (Roche/ACEA). These EGFR inhibitors led to a dose-dependent short-term and long-term decrease in Cell Index (CI). Plotting the Long-term (72 hours post compound treatment) CI versus the corresponding log concentration allows for calculation of the IC50 of BIBW2992, Canertinib and WZ4002 for wild-type EGFR. IC50 is 788 nM, 357 nM and 4.37 uM for BIBW2992, Canertinib and WZ4002 respectively. Overexpression of EGFR leads to receptor dimerization and consequent activation without ligand (EGF) stimulation. The IC50s derived from this experiment evaluate the inhibition of these inhibitors to this basal activation of EGFR (caused by dimerization without EGF stimulation)

Figure 15:
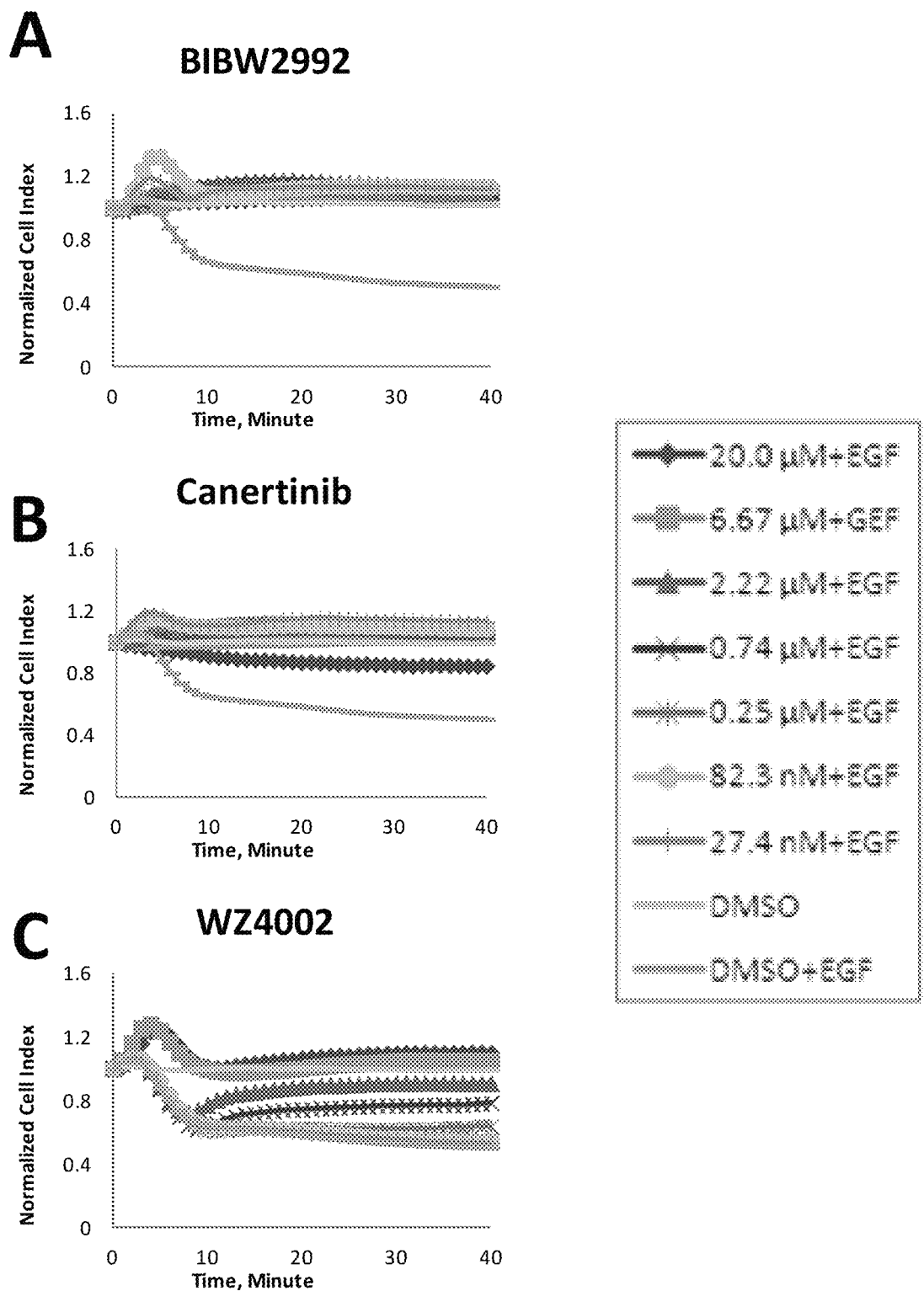
FIG. 15 depicts the pharmacological characterization of EGF-stimulated CI increase in A431: inhibited by EGFR inhibitors. A431 cells were seeded at 20,000 cells per well of 96-well E-plate (Roche/ACEA) with 2% fetal bovine serum. The cells were continuously monitored using xCelligence system (Roche/ACEA). The cells were treated with the EGFR inhibitor (A) BIBW2992, (B) Canertinib and (C) WZ4002 (from 0 to 20 uM) for 1 hour, then stimulated with EGF at 30 ng/ml. The cell index was normalized at time of EGF addition.

To further evaluate the efficacies of these EFGR inhibitors, we tested the inhibitory effect of these inhibitors on the EGF stimulated response using impedance-based technology (FIG. 15). In this experiment, A431 cells were seeded at 20,000 cells per well of 96-well E-plate (Roche/ACEA) with 2% fetal bovine serum. The cells were continuously monitored using xCelligence system (Roche/ACEA). The cells were treated with the EGFR inhibitor BIBW2992, Canertinib and WZ4002 (from 0 to 20 uM) for 1 hour, then stimulated with EGF at 30 ng/ml. The cell index was normalized at time of EGF addition. Normalized Cell Index at 30 minutes after EGF stimulation was used to generate IC50. Since the EGF stimulated responses is more sensitive to EGFR inhibitors, clear dose responses were not observed for BIBW2992 and Canertinib; a dose response was observed for a less potent inhibitor—WZ4002. The estimated IC50 is less than 27 nM for BIBW2992 and Canertinib, and 2 uM for WZ4002. The IC50s derived from this method (FIG. 15) differs significantly from those derived from inhibition of the constitutively activated EGFR (FIG. 14). This is not surprising, since this method evaluate the inhibition of the additional activation mode (caused by dimerization with EGF stimulation) instead of the basal activation mode (caused by dimerization without EGF stimulation).

Figure 16:
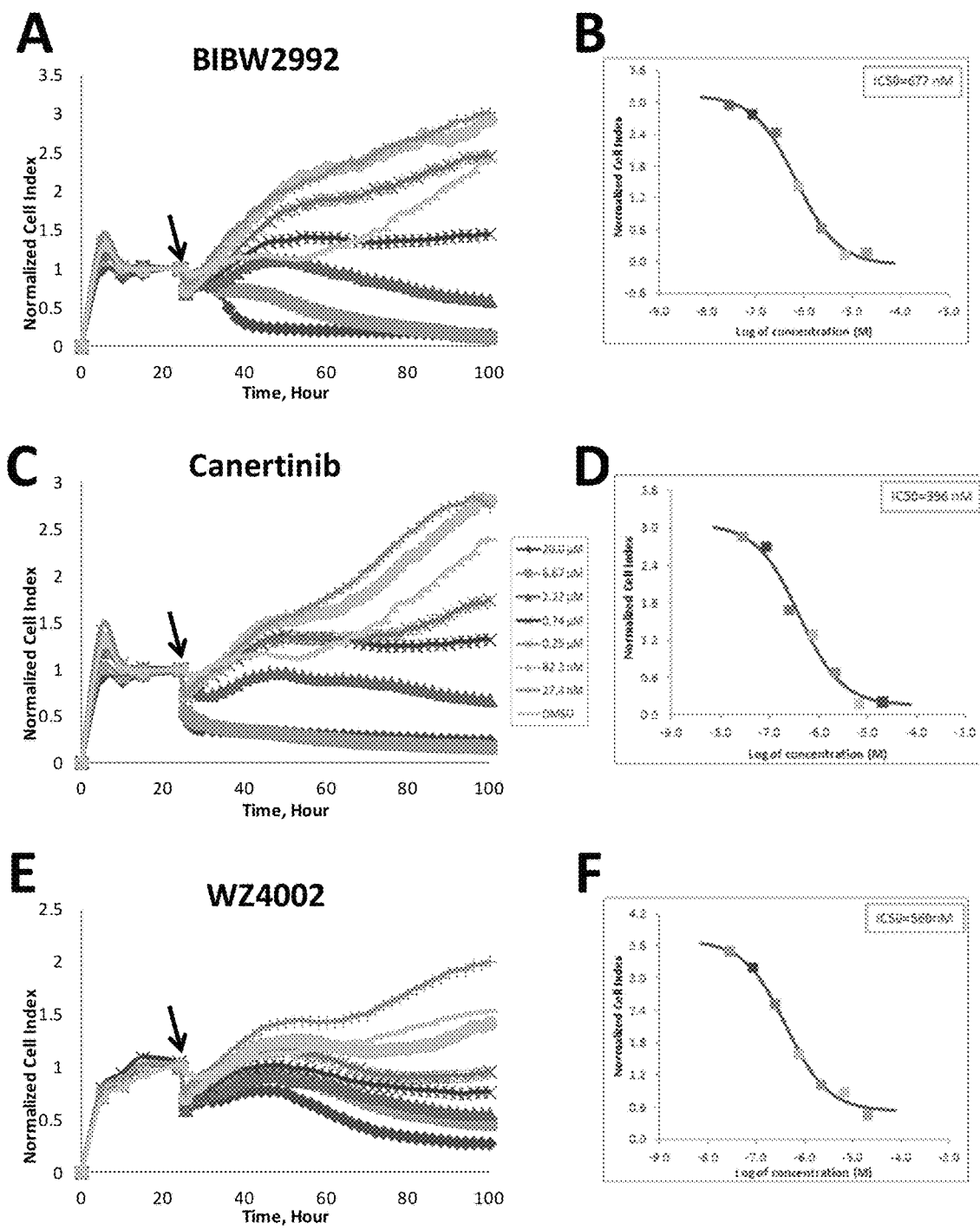
FIG. 16 shows impedance-based time-dependent cellular profiles (TCRPs) of H1975 in response to EGFR inhibitors on xCelligence system (Roche/ACEA). The TCRP was continuously recorded every 15 minutes for over 100 hours. The cell index (CI) was normalized at time of compound addition. At the indicated time point of treatment (arrow), increasing concentrations of EGFR inhibitor (A) BIBW2992, (C) Canertinib and (E) WZ4002 (from 0 to 20 uM) were added to the cells and the cell response was monitored. These EGFR inhibitors led to a dose-dependent short-term and long-term decrease in Cell Index (CI). Plotting the Long-term (72 hours post compound treatment) CI versus the corresponding log concentration allows for calculation of the IC50 of these (B) BIBW2992, (D) Canertinib and (F) WZ4002 for mutant EGFR (L858R/T790M).

FIG. 16 shows impedance-based time-dependent cellular profiles (TCRPs) of H1975 in response to EGFR inhibitors on xCelligence system (Roche/ACEA). H1975 cells were seeded at 3,000 cells per well of 96-well E-plate (Roche/ACEA) in RPMI1640 medium with 1% fetal bovine serum. The TCRP was continuously recorded every 15 minutes for over 100 hours. The cell index (CI) was normalized at time of compound addition. Increasing concentrations of EGFR inhibitor BIBW2992, Canertinib and WZ4002 (from 0 to 20 uM) were added to the cells and the cell response was monitored. These EGFR inhibitors led to a dose-dependent short-term and long-term decrease in Cell Index (CI). The IC50 (72 hours post compound treatment) for inhibiting mutant EGFR (L858R/T790M) is 677 nM, 396 nM and 560 uM for BIBW2992, Canertinib and WZ4002, respectively. The L858R mutation leads constitutive activation of EGFR without ligand (EGF) stimulation. The IC50s derived from this experiment evaluate the inhibition of these inhibitors to this constitutive active mutant of EGFR.

Figure 17:
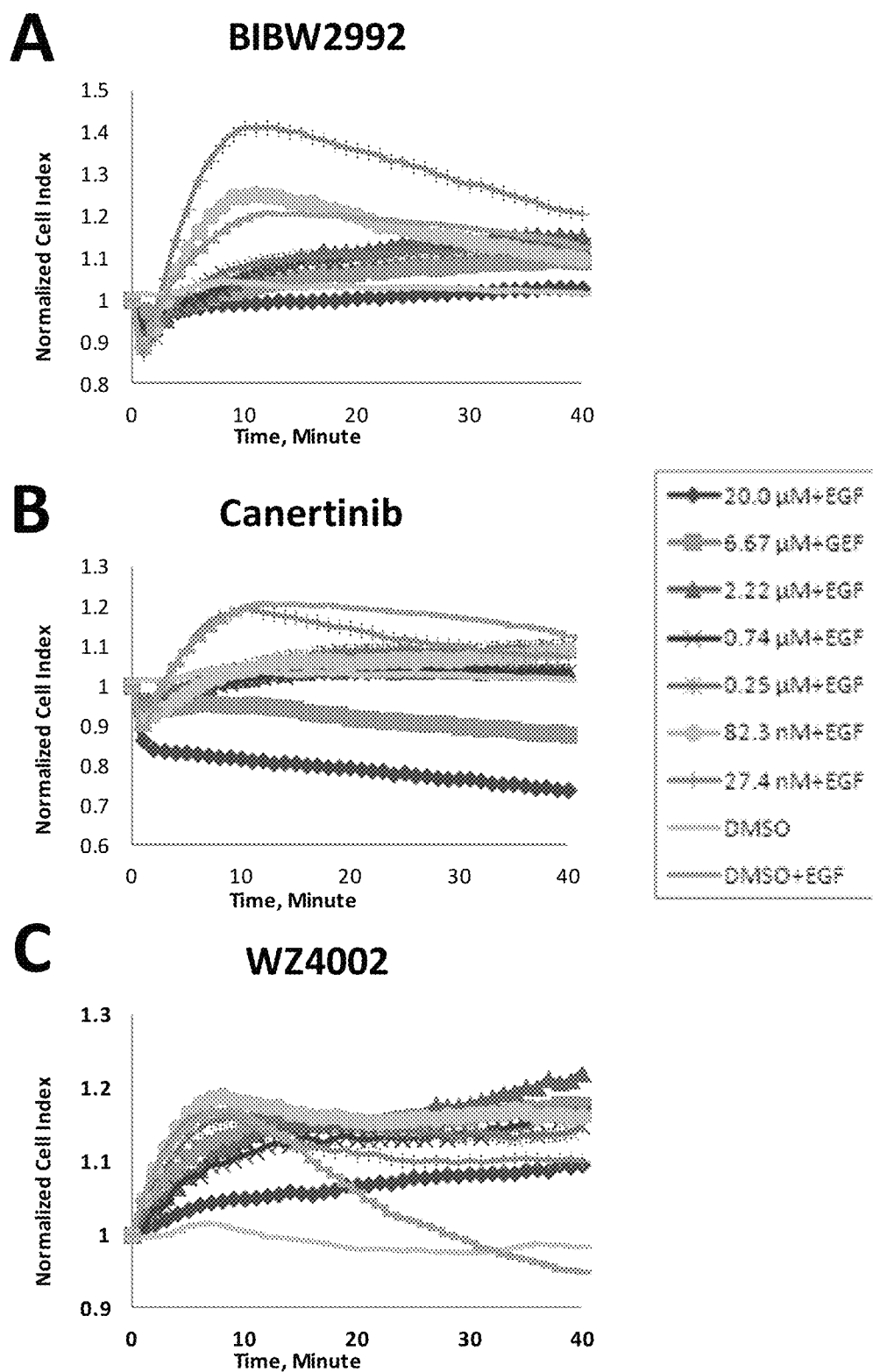
FIG. 17 depicts the pharmacological characterization of EGF-stimulated CI increase in H1975: inhibited by EGFR inhibitors. H1975 cells were seeded at 3,000 cells per well of 96-well E-plate (Roche/ACEA) with 1% fetal bovine serum. The cells were continuously monitored using xCelligence system (Roche/ACEA) for 40 hours. The cells were treated with the EGFR inhibitor (A) BIBW2992, (B) Canertinib and (C) WZ4002 (from 0 to 20 uM) for 1 hour, then stimulated with EFG at 30 ng/ml. The cell index was normalized at time of EGF addition.

To further evaluate the efficacies of these EFGR inhibitors, we tested the inhibitory effect of these inhibitors on the EGF stimulated response using impedance-based technology (FIG. 17). In this experiment, H1975 cells were seeded at 3,000 cells per well of 96-well E-plate (Roche/ACEA) in RPMI1640 medium with 1% fetal bovine serum. The cells were continuously monitored using xCelligence system (Roche/ACEA). The cells were treated with the EGFR inhibitor BIBW2992, Canertinib and WZ4002 (from 0 to 20 uM) for 1 hour, then stimulated with EGF at 30 ng/ml. The cell index was normalized at time of EGF addition. Normalized Cell Index at 30 minutes after EGF stimulation was used to generate IC50. The IC50s are estimated to be 200 nM, 150 nM and 1.25 uM for BIBW2992, Canertinib, and WZ4002, respectively. This this method evaluate the inhibition of the additional activation mode (caused by dimerization with EGF stimulation) instead of the basal activation mode (caused by activating L858R mutation). Although the IC50s derived from these two methods are accidentally similar, they are IC50 evaluating two different inhibition modes.

Figure 18:
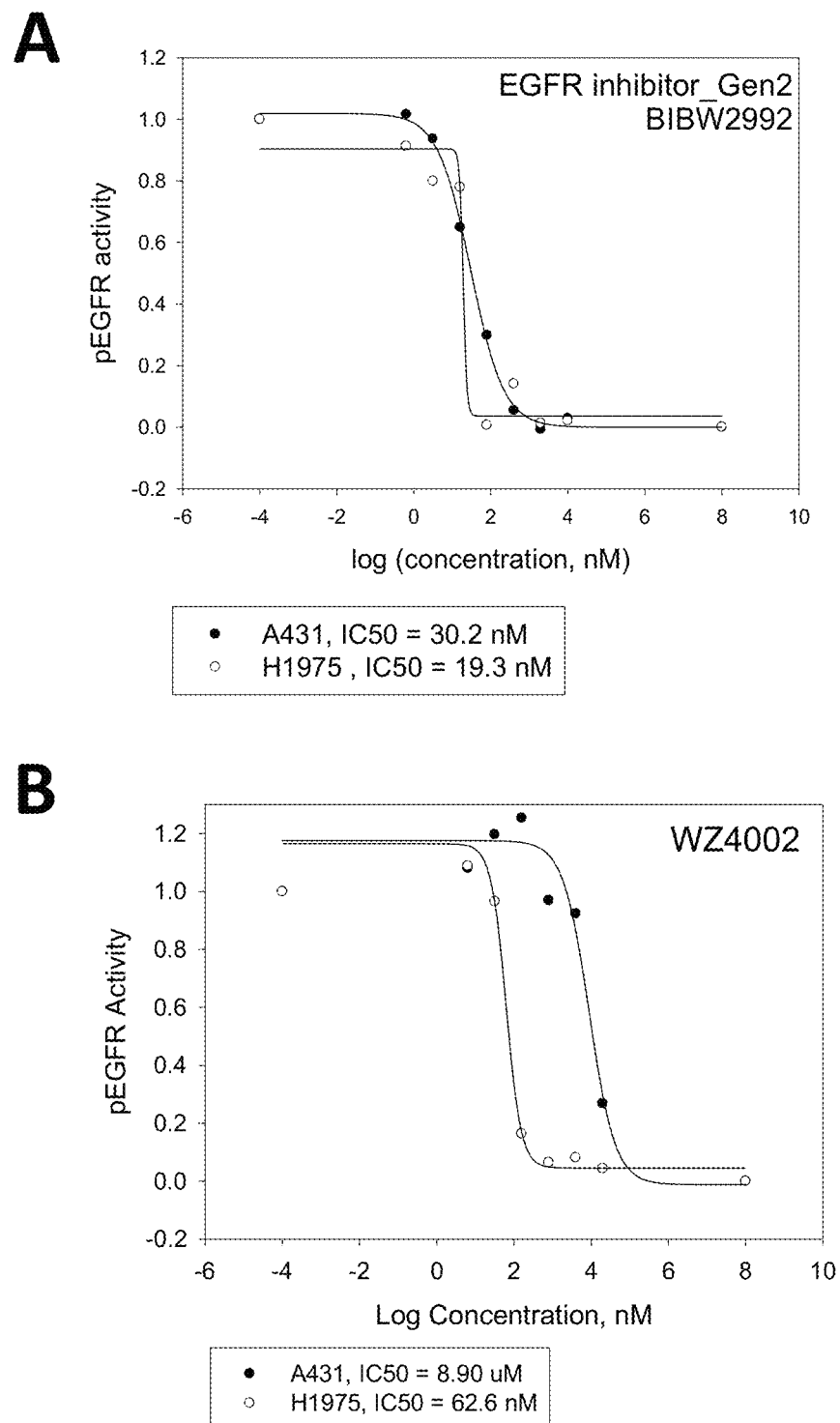
FIG. 18 shows the effect of three EGFR inhibitors (A) BIBW2992 and (B) WZ4002 on the constitutive activity of EGFR in A431 and H1975 cells. Plotting the phospho-EGFR (Y1068) (2 hours post compound treatment) versus the corresponding log concentration allows for calculation of the IC50 of the EGFR inhibitors for wild-type and mutant (L858R/T790M) EGFR. IC50 was calculated based on curve fitting software (Sigma Plot).

In addition, we also evaluated the efficacy of three EGFR inhibitors using an ELISA assay (FIG. 18). In this assay A431 cells were seeded to wells of 96-well plate with initial seeding density of 60,000 cells per well; H1975 were seeded to wells of 96-well plate with initial seeding density of 40,000 cells per well. Cells were pre-incubated in the incubator under standard cell culture condition overnight. Cells were serum starved for 1 hour, then incubated with increasing concentrations of EGFR inhibitors in serum free medium for additional 2 hours. Cells were lysed and cell lysates were used for ELISA assay (Cell Signaling) according to manufactory recommended procedures. Plotting the phospho-EGFR (Y1068) versus the corresponding log concentration allows for calculation of the IC50 of BIBW2992 and WZ4002 for both the wild-type and mutant EGFR. The IC50 toward wild-type EGGR is 30.2 nM and 8.90 uM for BIBW2992 and WZ4002, respectively. The IC50 toward mutant (L858R/T790M) EGGR is 19.3 nM and 62.6 nM for BIBW2992 and WZ4002, respectively. Overall, the IC50s derived from TCRP (inhibition of the basal activation modes or constitutive activation) and the IC50 derived from ELISA correlated very well (See Table 2). In general, the IC50 derived from ELISA (which evaluate the phosphorylation of EGFR is 10 fold lower than the IC50 derived from TCRP. This is not surprising, because cell growths cannot be inhibited until 99% of the driven oncogene is inhibited, which means 99% inhibition of the EGFR phosphorylation. In contrast, the IC50 does not correlate with the IC50 derived from EGF stimulation. The hypothesis has been stated above.

TABLE 2

| | A431 (wild-type EGFR) | | | H1975 (mutant L858R/T790M EGFR) | | |
|---|---|---|---|---|---|---|
| | Consitutive activation | | Ligand stimulated | Consitutive activation | | Ligand stimulated |
| | TCRP | ELISA | TCRP | TCRP | ELISA | TCRP |
| BIBW2992 | 788 nM | 30.2 nM | <27 nM | 677 nM | 19.3 nM | ~200 nM |
| WZ4002 | 4.37 uM | 8.90 uM | ~2 uM | 560 nM | 62.6 nM | ~1.25 uM |

This is indicative that the TCRP upon Met inhibitory addition is a function of phospho-Met inhibition, and that this specific TCRP pattern can be used to identify unknown cMet inhibitor in a screen setting or to elucidate mechanism of action of an known/unknown compound.

FIG. 18 shows the effect of three EGFR inhibitors (A) Lapatinib (B) BIBW2992 and (C) WZ4002 on the constitutive activity of EGFR in A431 and H1975 cells. Plotting the phospho-EGFR (Y1068) (2 hours post compound treatment) versus the corresponding log concentration allows for calculation of the IC50 of the EGFR inhibitors for wild-type and mutant (L858R/T790M) EGFR. IC50 was calculated based on curve fitting software (Sigma Plot).

Figure 19:
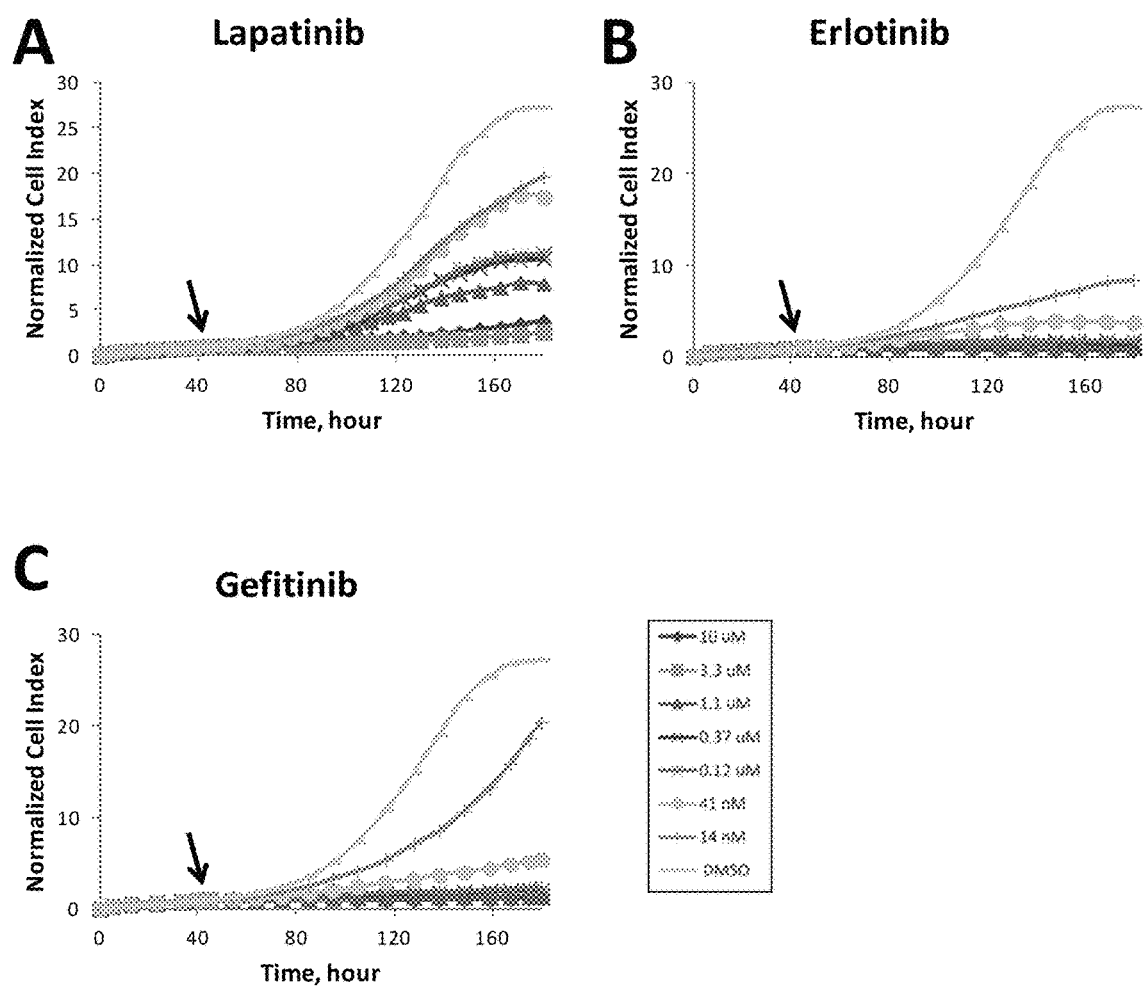
FIG. 19 shows impedance-based time-dependent cellular profiles (TCRPs) of HCC827 in response to EGFR inhibitors on xCelligence system (Roche/ACEA). The TCRP was continuously recorded every 15 minutes for over 190 hours. The cell index (CI) was normalized at time of compound addition. At the indicated time point of treatment (arrow), increasing concentrations of EGFR inhibitor (A) Lapatinib, (B) Erlotinib and (C) Gefitinib (from 0 to 10 uM) were added to the cells and the cell response was monitored. These EGFR inhibitors led to a dose-dependent short-term and long-term decrease in Cell Index (CI).
Figure 20:
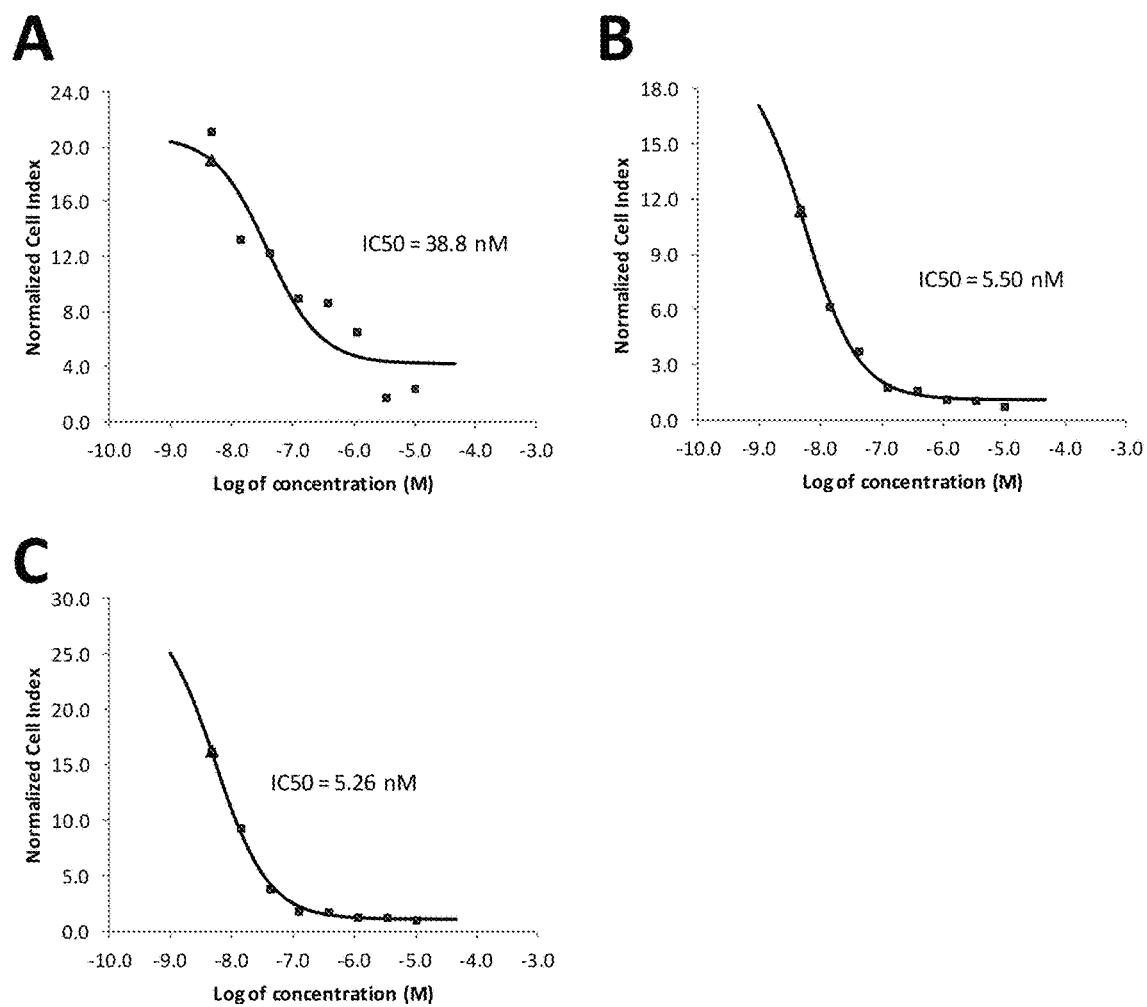
FIG. 20 IC50 of EGFR derived from impedance-based TCRP. (A) Lapatinib, (B) Erlotinib and (C) Gefitinib led to a dose-dependent long-term decrease in Cell Index (CI). Plotting the Long-term (96 hours post compound treatment) CI versus the corresponding log concentration allows for calculation of the IC50 of these compounds for the mutant EGFR (Del E746_A750) in HCC827.
Figure 21:
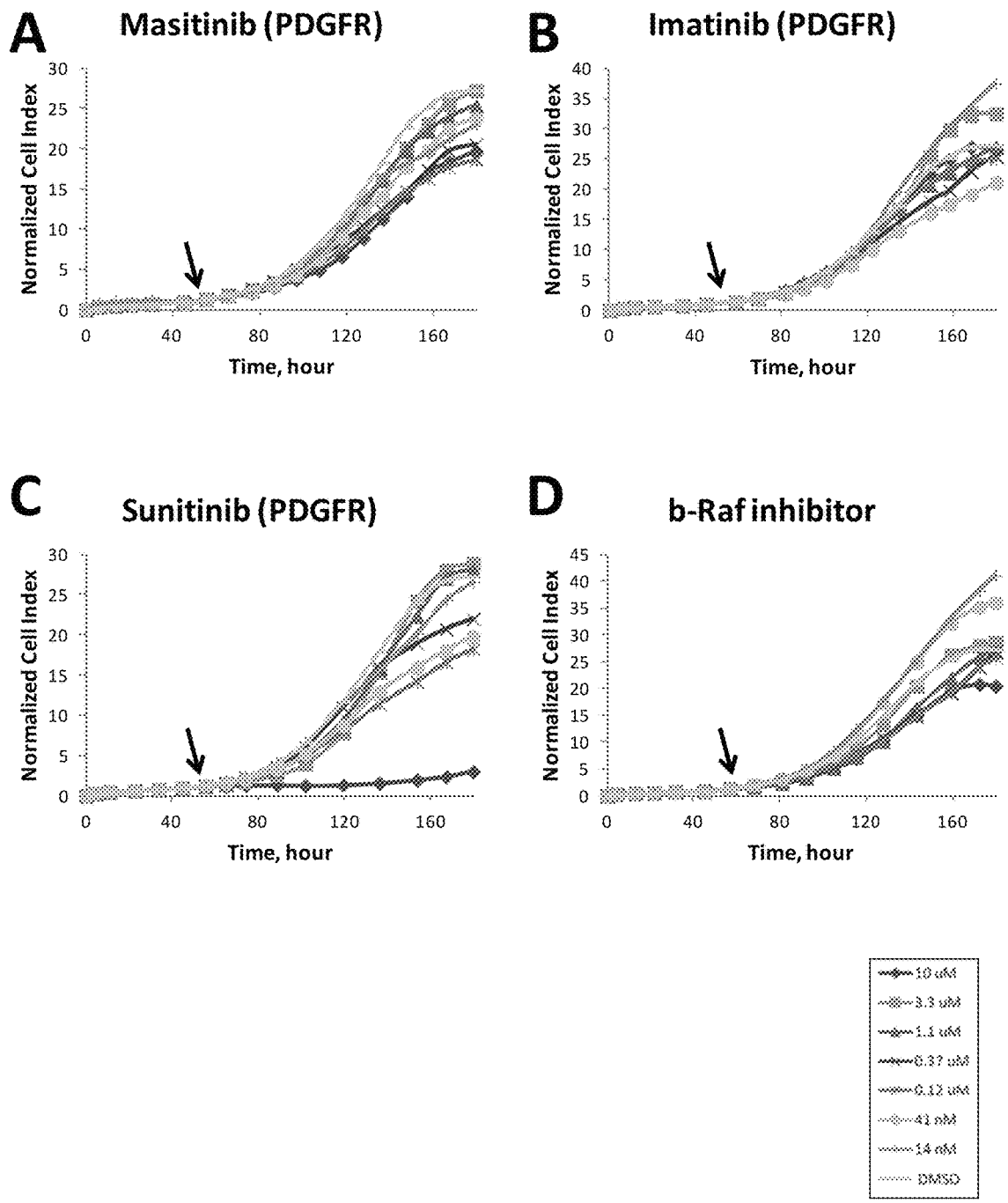
FIG. 21 shows impedance-based time-dependent cellular profiles (TCRPs) of HCC827 in response to a panel of protein kinase inhibitors on xCelligence system (Roche/ACEA). The TCRP was continuously recorded every 15 minutes for over 190 hours. The cell index (CI) was normalized at time of compound addition. At the indicated time point of treatment (arrow), increasing concentrations of (A) Masitinib, (B) Imatinib, (C) Sunitinib, (D) b-Raf inhibitor (from 0 to 10 uM) and (E) c-MET inhibitor (PF02341066) (from 0 to 1 uM) were added to the cells and the cell response was monitored. These kinase inhibitors did not inhibit HCC827 cell growth (long-term decrease in CI), except that Sunitinib inhibited the cell growth at the highest concentration (10 uM) due to its nonspecific inhibition to EGFR.
Figure 21:
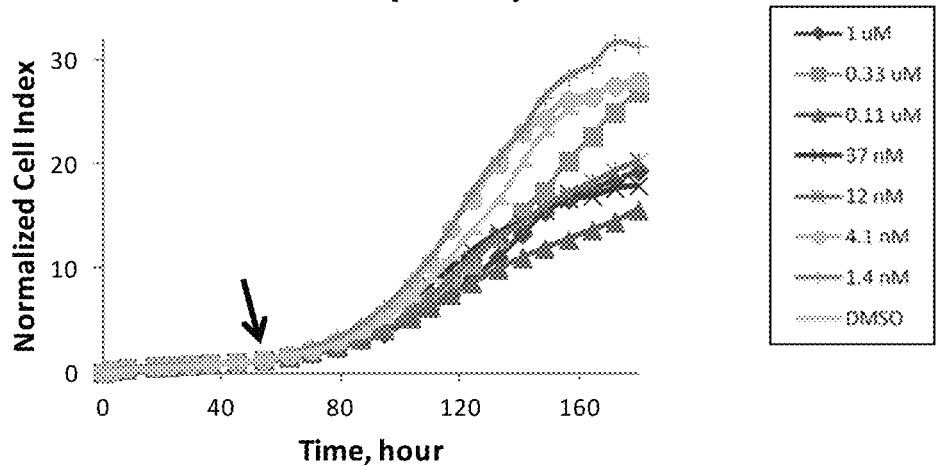

FIG. 19 shows impedance-based time-dependent cellular profiles (TCRPs) of HCC827 in response to EGFR inhibitors on xCelligence system (Roche/ACEA). HC827 cells were seeded into wells of 96 well E-plate devices (Roche applied sciences) with an initial seeding density of 5000 cells per well and were pre-incubated in incubator under standard cell culture condition for about 24 hours. Kinase inhibitors including EGFR inhibitors at different concentrations in DMSO were added into wells following the incubation period. The cell status was monitored prior to and after the compound addition using xCelligence system (Roche applied sciences). The Cell index was normalized against the cell index values at a time point just before compound addition. These EGFR inhibitors led to a dose-dependent short-term and long-term decrease in Cell Index (CI). The dose response curves demonstrate that the growth and proliferation of HC827 cells were extremely sensitive to EGFR inhibitor treatment. Plotting the Long-term (96 hours post compound treatment) CI versus the corresponding log concentration allows for calculation of the IC50 of these compounds for the mutant EGFR (Del E746_A750) in HCC827 (FIG. 20). The calculated IC50 for lapatinib, erlotinib and gefitinib is 38.8 nM, 5.50 nM and 5.26 nM, respectively. In contrast, the growth and proliferation (as demonstrated by the TCRP) of HC827 were not significantly altered by the inhibition by PDGFR inhibitors (mastitinib, imatinib and sunitinib), B-raf inhibitor and Met inhibitor (FIG. 21 A-E), These results suggest the sensitivity of HC827 (as demonstrated by the TCRP) is specific to EGFR inhibitors.

Example 5

Figure 22:
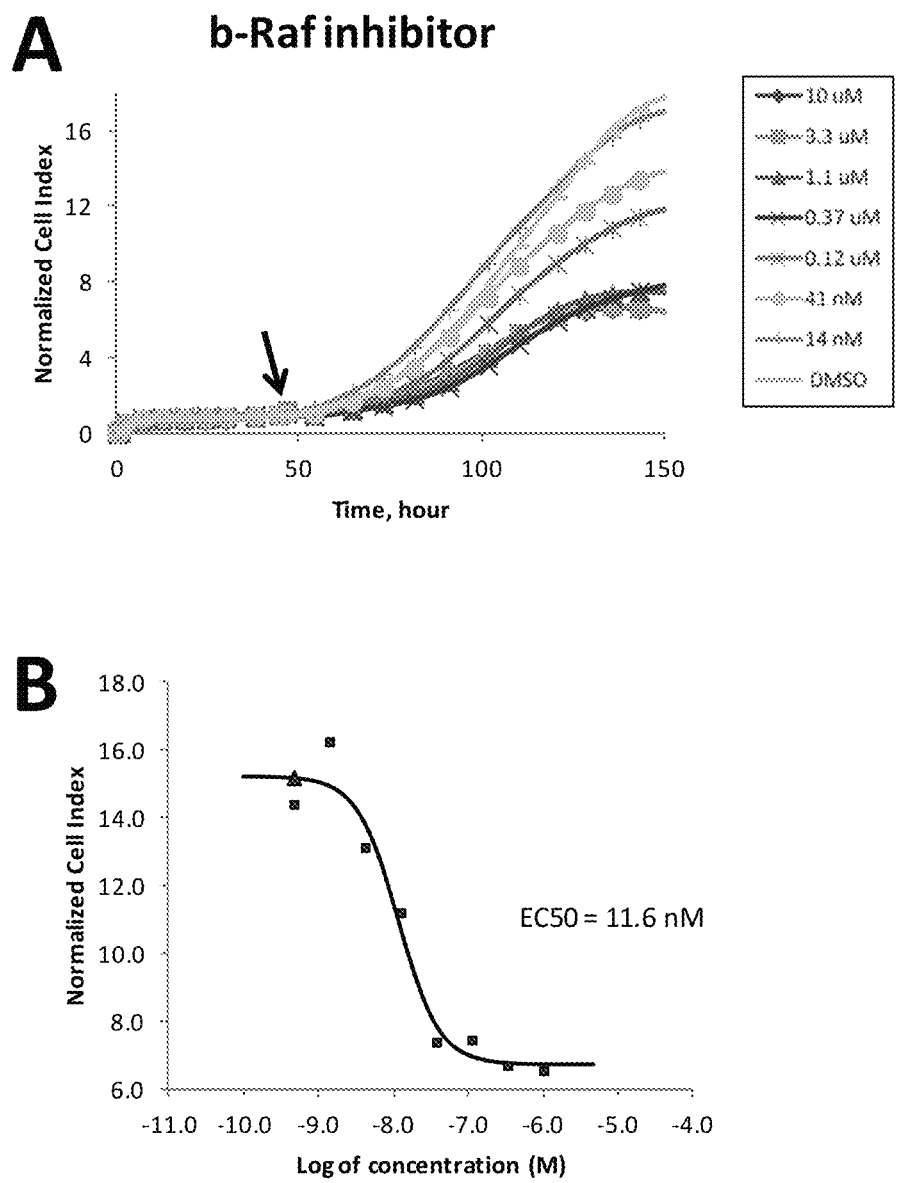
FIG. 22 shows the effect of b-Raf inhibitor on colo205, a b-Raf (V600E) mutation-positive colon cell line. (A) The impedance-based time-dependent cellular profiles (TCRPs) of colo205 in response to b-Raf inhibitor on xCelligence system (Roche/ACEA). The TCRP was continuously recorded every 15 minutes for over 150 hours. The cell index (CI) was normalized at time of the compound addition. At the indicated time point of treatment (arrow), increasing concentrations of b-Raf inhibitor (from 0 to 10 uM) were added to the cells and the cell response was monitored. These EGFR inhibitors led to a dose-dependent long-term decrease in Cell Index (CI). (B) IC50 of b-Raf derived from impedance-based TCRP. Plotting the Long-term (96 hours post compound treatment) CI versus the corresponding log concentration allows for calculation of the IC50 of b-Raf inhibitor for the mutant b-Raf (V600E) in Colo205.
Figure 23:
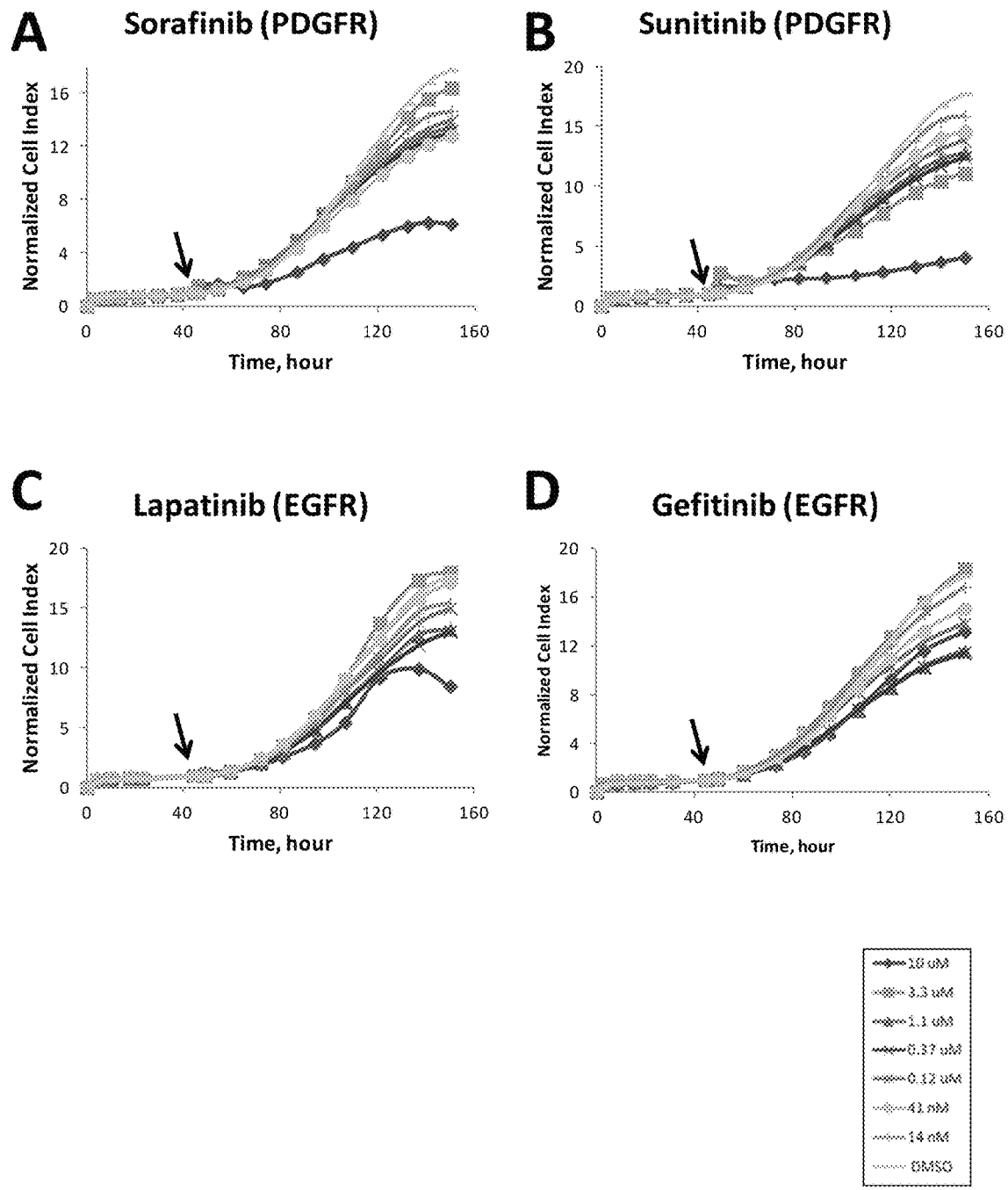
FIG. 23 shows impedance-based time-dependent cellular profiles (TCRPs) of colo205 in response to a panel of protein kinase inhibitors on xCelligence system (Roche/ACEA). The TCRP was continuously recorded every 15 minutes for over 150 hours. The cell index (CI) was normalized at time of compound addition. At the indicated time point of treatment (arrow), increasing concentrations of (A) Sorafinib, (B) Sunitinib, (C) Lapatinib, (D) Gefitinib (from 0 to 10 uM) and (E) c-MET inhibitor (PF02341066) (from 0 to 1 uM) were added to the cells and the cell response was monitored. These kinase inhibitors did not inhibit Colo205 cell growth, except that Sorafinib, Sunitinib and Lapatinib inhibited the cell growth at the highest concentration (10 uM) due to their nonspecific inhibition to b-Raf.
Figure 23:
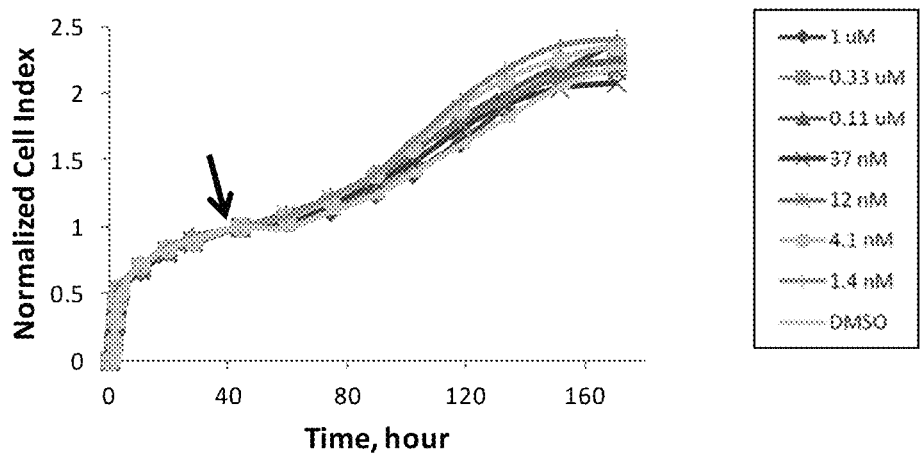

B-raf Addicted Cell Lines Show Characteristic Time-dependent Cell Response Profiles (TCRP) to b-raf Inhibitors Cell lines. Colo-205 human colon cancer cell line and SK-MEL-28 human melanoma cell line expressing a mutant form of b-Raf (V600E) are a b-Raf addictive cell line. Colo-205 cells were seeded into wells of 96 well E-plate devices (Roche applied sciences) with an initial seeding density of 5000 cells per well and were pre-incubated in incubator under standard cell culture condition for about 24 hours. Kinase inhibitors including b-Raf inhibitors at different concentrations in DMSO were added into wells following the incubation period. The cell status was monitored prior to and after the compound addition using xCelligence system (Roche applied sciences). FIG. 22A shows the normalized cell index as a function of time prior to and after compound addition. The Cell index was normalized against the cell index values at a time point just before compound addition. The dose response curves (TCRP) demonstrate that the growth and proliferation of Colo-205 cells were sensitive to b-Raf inhibitor treatment. The calculated IC50 (96 hours post compound addition) for b-Raf inhibitor is 11.6 nM (FIG. 22B). In contrast, the growth and proliferation (as demonstrated by the TCRP) of Colo-205 were not significantly altered by PDGFR inhibitors (sorafenib and sunitinib), EGF inhibitors (lapatinib and gefitinib) and Met inhibitor (PF02341066) treatment (FIG. 23). These results suggest the sensitivity of Colo-205 (as demonstrated by the TCRP) is specific to b-Raf inhibition.

Figure 24:
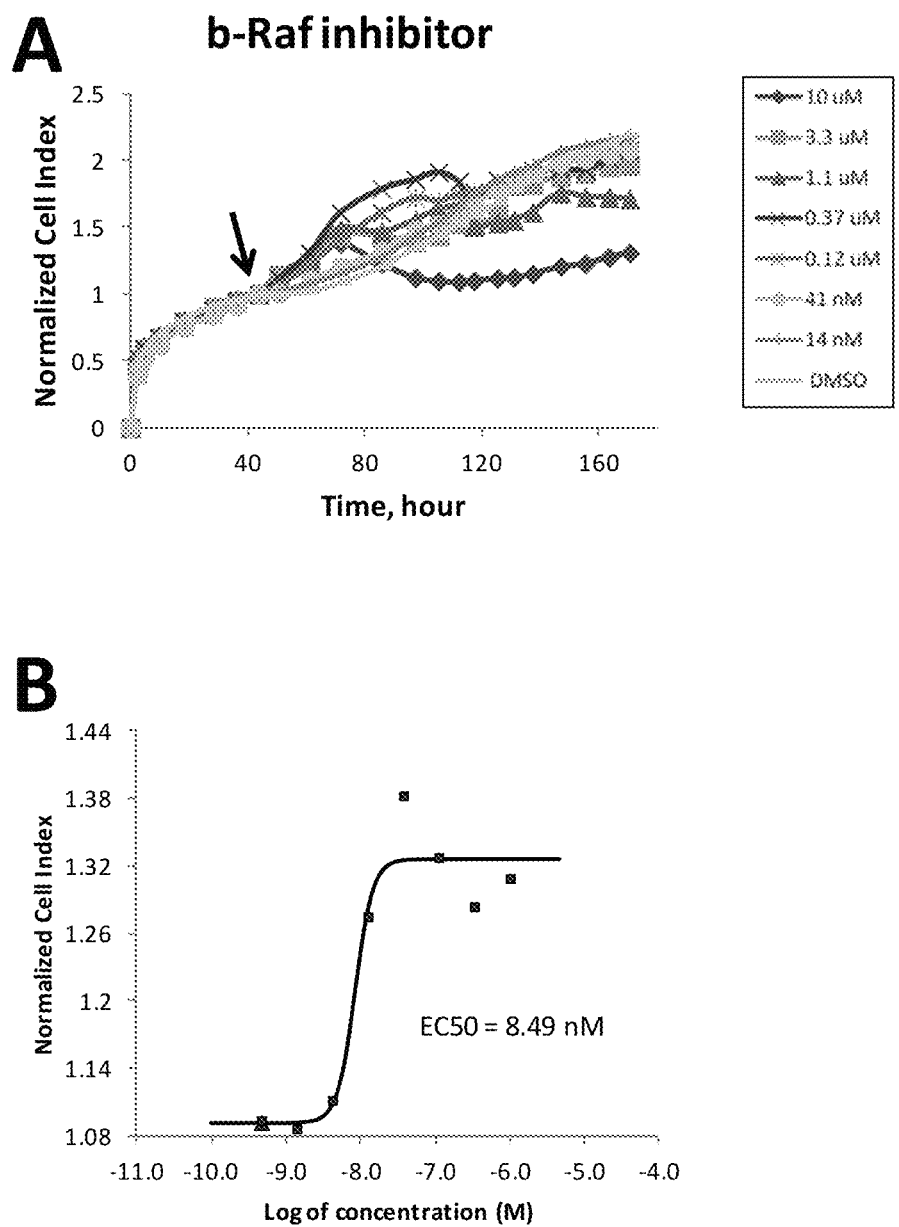
FIG. 24 shows the effect of b-Raf inhibitor on SK-MEL28, a b-Raf (V600E) mutation-positive melanoma cell line. (A) The impedance-based time-dependent cellular profiles (TCRPs) of SK-MEL28 in response to b-Raf inhibitor on xCelligence system (Roche/ACEA). The TCRP was continuously recorded every 15 minutes for over 170 hours. The cell index (CI) was normalized at time of the compound addition. At the indicated time point of treatment (arrow), increasing concentrations of b-Raf inhibitor (from 0 to 10 uM) were added to the cells and the cell response was monitored. The b-Raf inhibitor led to a dose-dependent short-term increase and long-term decrease in Cell Index (CI). (B) EC50 of b-Raf derived from impedance-based TCRP. Plotting the short-term (20 hours post compound treatment) CI versus the corresponding log concentration allows for calculation of the EC50 of b-Raf inhibitor for the mutant b-Raf (V600E) in SK-MEL28.
Figure 25:
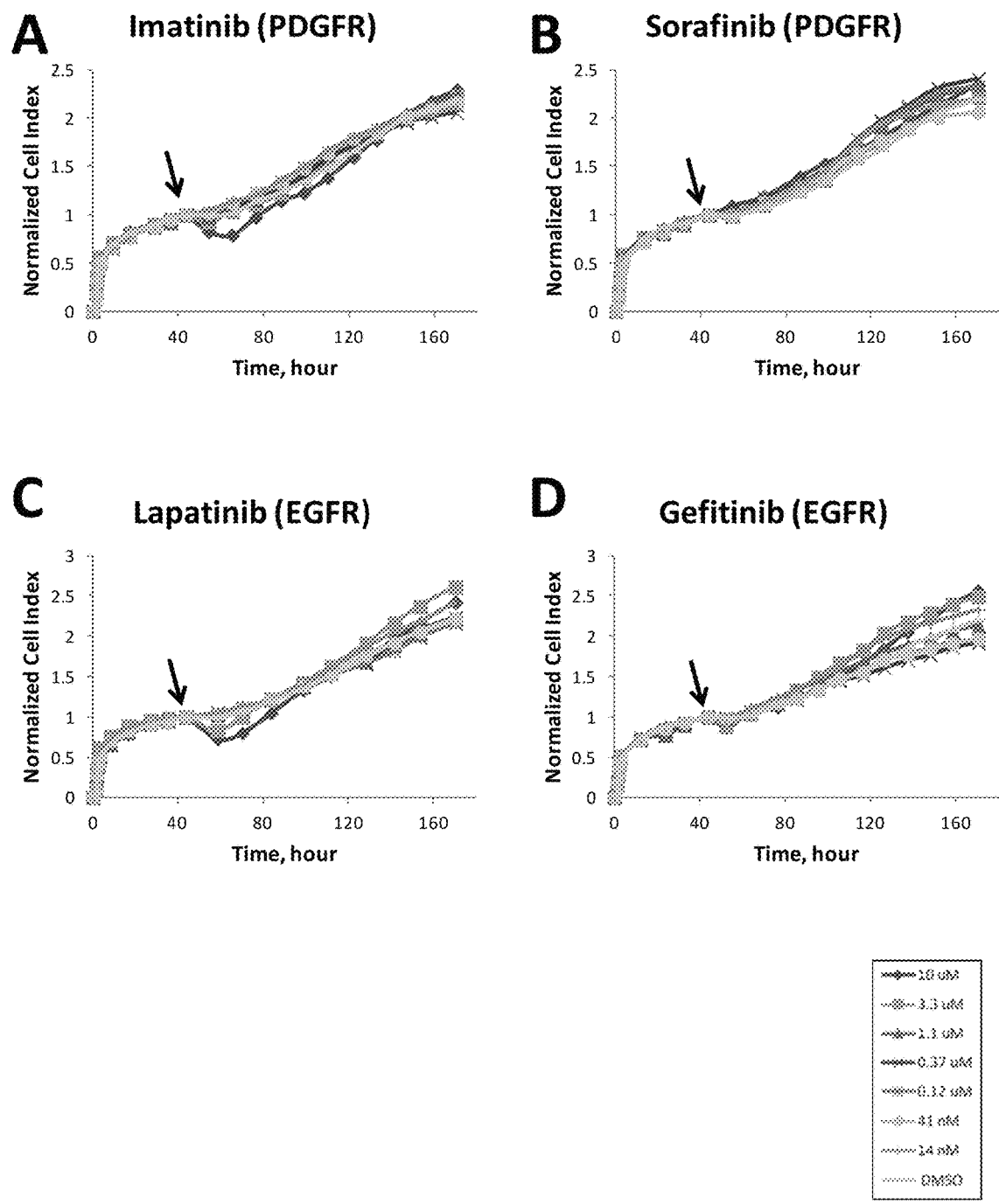
FIG. 25 shows impedance-based time-dependent cellular profiles (TCRPs) of SK-MEL28 in response to a panel of protein kinase inhibitors on xCelligence system (Roche/ACEA). The TCRP was continuously recorded every 15 minutes for over 170 hours. The cell index (CI) was normalized at time of compound addition. At the indicated time point of treatment, increasing concentrations of (A) Imatinib, (B) Sorafinib, (C) Lapatinib, (D) Gefitinib (from 0 to 10 uM) and (E) c-MET inhibitor (PF02341066) (from 0 to 1 uM) were added to the cells and the cell response was monitored. These kinase inhibitors did not led to either short or long term response (changes in CI) in SK-MEL28.
Figure 25:
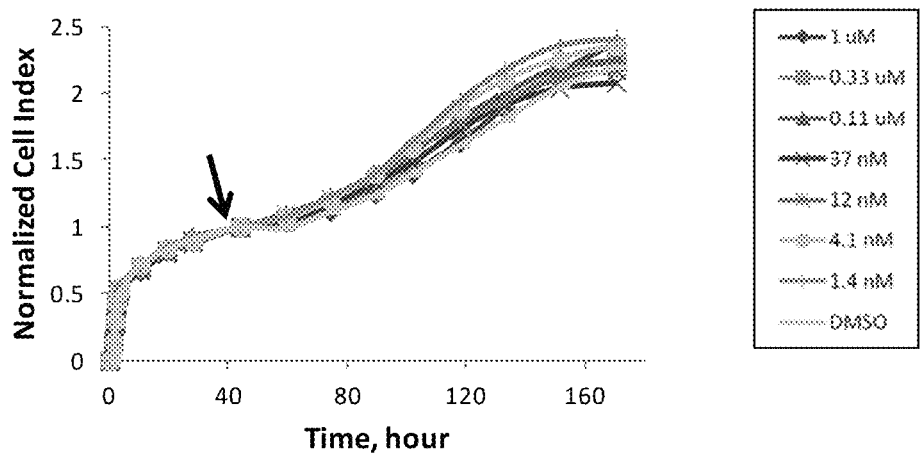

SK-MEL-28 cells were seeded into wells of 96 well E-plate devices (Roche applied sciences) with an initial seeding density of 5000 cells per well and were pre-incubated in incubator under standard cell culture condition for about 24 hours. Kinase inhibitors including b-Raf inhibitors at different concentrations in DMSO were added into wells following the incubation period. The cell status was monitored prior to and after the compound addition using xCelligence system (Roche applied sciences). FIG. 24A shows the normalized cell index as a function of time prior to and after compound addition. The Cell index was normalized against the cell index values at a time point just before compound addition. Upon b-Raf inhibitor treatment (0-10 uM), SK-MEL-28 showed an initial increase (within 40 hr, short-term response) in the cell index followed by a steady decrease (long-term response) in the cell index (FIG. 24A). Plotting the short-term (20 hours post compound addition) normalized CI response versus the corresponding log concentration allows for calculation of the EC50 (8.49 nM) b-Raf inhibitor acting on SK-MEL-28 (FIG. 24B). To confirm the specificity of the time-dependent cell response profiles (TCRP) to b-Raf inhibitors, we also tested the TCRP in response to PDGFR inhibitors (Imatinib and sorafenib), EGF inhibitors (lapatinib and gefitinib) and Met inhibitor (PF02341066) treatment (FIG. 25 These inhibitors did not affect CI changes that are significantly different from the negative control (DMSO treated cells). In addition, non-b-Raf addicted cell lines C6 (FIG. 10A) and HCC827 (FIG. 17D) did not respond to b-Raf inhibition. These results indicate that the characteristic impedance-based TCRP observed for b-Raf inhibiton is specific to SK-MEL-28 treated with PDGFR inhibitor. A recent publication (Klein, et. al. *Mol Biol Cell.* 2008 19:498-508) demonstrated that inhibition of b-Raf or its signaling pathway led to increased actin stress fiber formation and stabilized focal adhesion dynamics in human melanoma cells. These morphological/adhesion changes could well translate to changes in impedance signals resulting in increased CI. Since SK-MEL-28 is addicted to b-Raf, the long term effect of b-Raf inhibition will results in cell death (thus decrease in CI). Taken together, the characteristic TCRP to b-Raf inhibitors demonstrated by SK-MEL-28 not only gives us a method in screening for b-Raf inhibitor but also gives insights to the molecular mechanism of this inhibition.

Example 6

ALK Addicted Cell Lines Show Characteristic Time-dependent Cell Response Profiles (TCRP) to ALK Inhibitors Cell lines. SH-SY5Y human neuroblastoma cell line expressing a mutant form of ALK (F1174L) is an ALK addicted cell line. Karpas-299 human ALCL cell line expressing a fusion NPM-ALK is also ALK addicted cell line. Both mutation (F1176L) and fusion (NPM-ALK) leads to constitutive activation of ALK.

Figure 26:
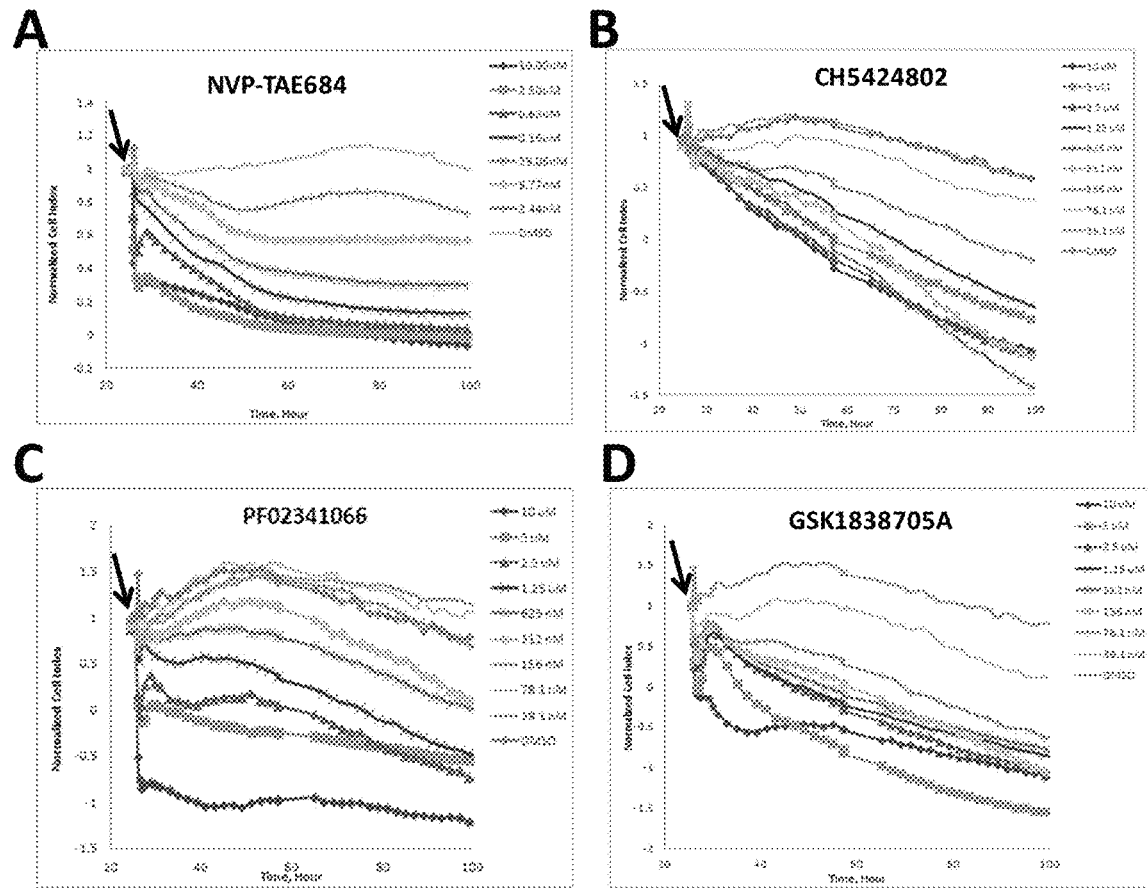
FIG. 26 shows impedance-based time-dependent cellular profiles (TCRPs) of SH-SY5Y in response to ALK inhibitors on xCelligence system (Roche/ACEA). The TCRP was continuously recorded every 15 minutes for over 100 hours. The cell index was normalized at time of compound addition. At the indicated time point of treatment (arrow), increasing concentrations of (A) NVP-TAE684, (B) CH5424802, (C) PF02341066 and (D) GSK1838705A (from 0 to 10 uM) were added to the cells and the cell responses were monitored. All these ALK inhibitors led to dose-dependent short-term and long-term decrease in Cell Index (CI).
Figure 27:
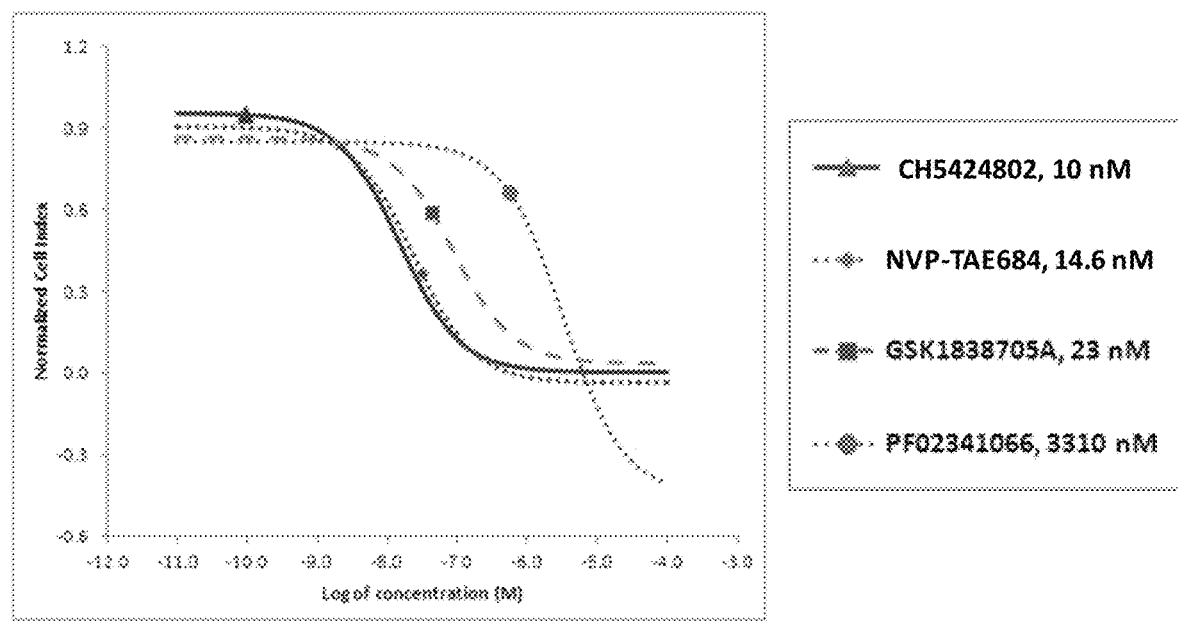
FIG. 27 IC50 of ALK derived from impedance-based TCRP. Plotting the long-term (72 hours post compound treatment) CI versus the corresponding log concentration allows for calculation of the IC50 of ALK inhibitors for the mutant ALK (F1174L) in SH-SY5Y.

SH-SY5Y cells were seeded into wells of 384 well E-plate devices (Roche applied sciences) with an initial seeding density of 20,000 cells per well and pre-incubated in RPMI-1640 plus 2% fetal bovine serum overnight. Increasing concentrations of NVP-TAE684, CH5424802, PF02341066 and GSK1838705A (from 0 to 10 uM) were added to the cells and the cell responses were monitored (FIG. 26). The cell index was normalized at time of compound addition. DMSO at the same dose was served as solvent control. ALK inhibitors triggered both short-term and long-term Cell Index decreases. Plotting the long-term (72 hours post compound treatment) CI versus the corresponding log concentration allows for calculation of the IC50 of ALK inhibitors for the mutant ALK (F1174L) in SH-SY5Y (FIG. 27). The calculated IC50 for TAE687, PF02341066, CH8029 and GSK705A is 10.4 nM, 3.0 uM, 3.5 uM and 137 nM, respectively.

Figure 28:
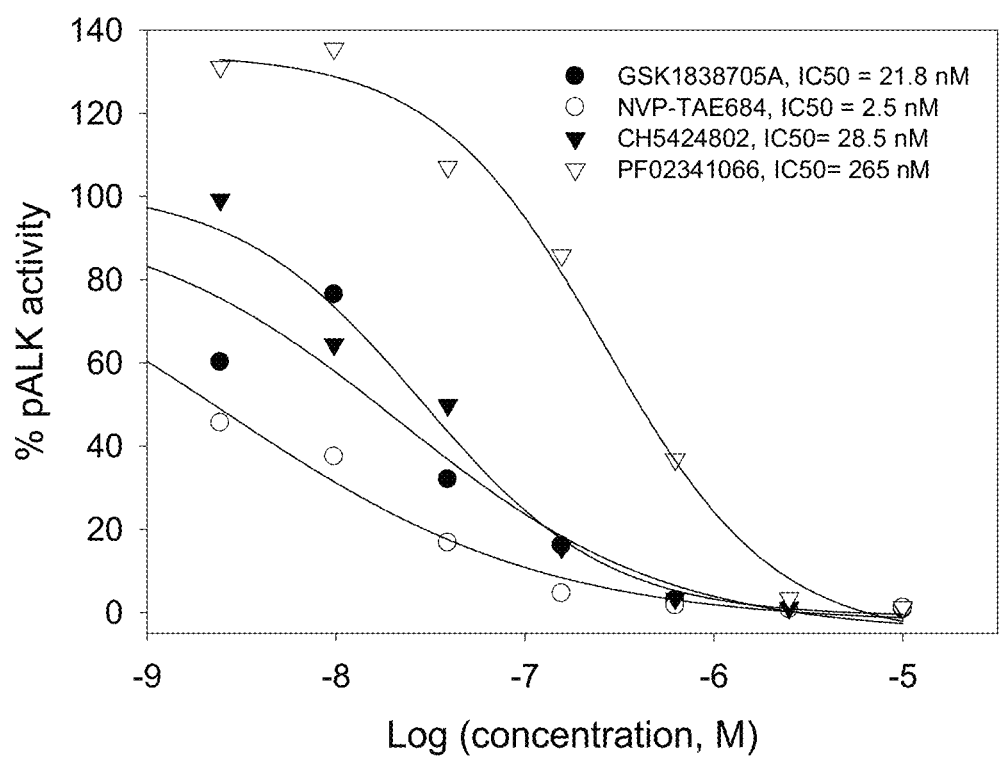
FIG. 28 shows the effect of four ALK inhibitors NVP-TAE684, CH5424802, PF02341066 and GSK1838705A on the phosphorylation status of ALK in Karpas-299 cells. Plotting the phospho-ALK (Y1604) (1 hour post compound treatment) versus the corresponding log concentration allows for calculation of the IC50 of the ALK inhibitors for the mutant ALK (F1174L). IC50 was calculated based on curve fitting software (Sigma Plot).

FIG. 28 shows the effect of four ALK inhibitors TAE684, CH8029, PF02341066 and GSK705A on the phosphorylation status of ALK in Karpas-299 cells. Plotting the phospho-ALK (Y1604) (1 hour post compound treatment) versus the corresponding log concentration allows for calculation of the IC50 of the ALK inhibitors for the fusion mutant ALK (NPM-ALK). The IC50 for NVP-TAE684, PF02341066, CH5424802, and GSK1838705A is 2.5 nM, 0.265 uM, 28.5 nM and 21.8 nM, respectively. The ranking of the IC50 derived from ELISA assay correlates well with that from TCRP (FIG. 26-27).

Figure 29:
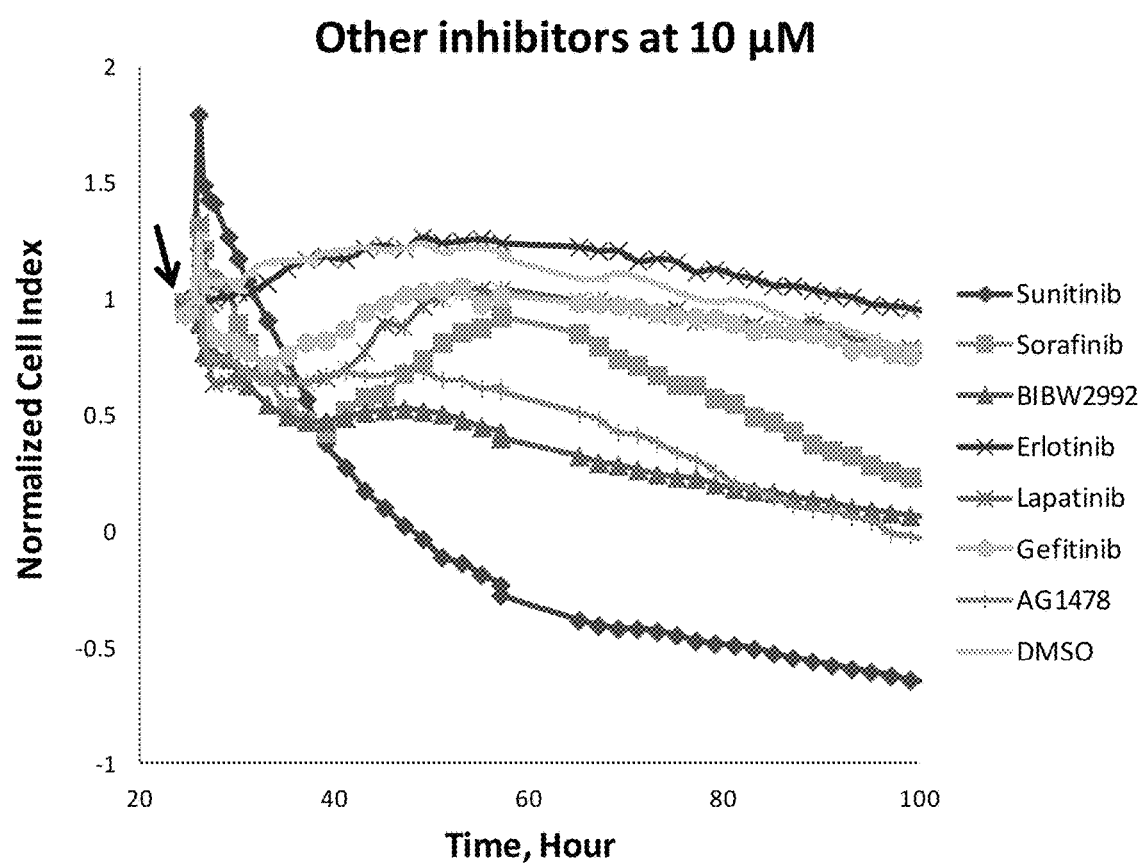
FIG. 29 shows time-dependent cellular profiles (TCRPs) of SH-SY5Y in response to a panel of protein kinase inhibitors on xCelligence system (Roche/ACEA). The TCRP was continuously recorded every 15 minutes for over 100 hours. The cell index (CI) was normalized at time of compound addition. At the indicated time point of treatment (arrow), 10 uM Sunitinib, Sorafinib, BIBW2992, Erlotinib, Lapatinib, Gefitinib, and AG1478 were added to the cells and the cell response was monitored. DMSO was served as solvent control.

FIG. 29 shows time-dependent cellular profiles (TCRPs) of SH-SY5Y in response to a panel of protein kinase inhibitors on xCelligence system (Roche/ACEA). The TCRP was continuously recorded every 15 minutes for over 100 hours. The cell index (CI) was normalized at time of compound addition. At the indicated time point of treatment, 10 uM Sunitinib, Sorafinib, BIBW2992, Erlotinib, Lapatinib, Gefitinib, and AG1478 were added to the cells and the cell response was monitored. None trigged a TCRP representative to that trigger by ALK inhibitors. Although some inhibitors trigger Cell Index decrease (e.g. Lapatinib), but the kinetics are different. During a screen setting, this type of TCRP can be easily sort out by mathematic algorithms. Overall, the ALK addicted cell line show characteristic time-dependent cell response profiles (TCRP) to ALK inhibitors.

Example 7

Constitutive Active PI3Kα Mutant Cell Lines Show Characteristic Time-dependent Cell Response Profiles (TCRP) to PI3K Inhibitors Cell lines. A mouse fibroblast 10T1/2 expressing the cell-surface receptor TVA, which is specific for subgroup-A avian retroviruses was used. The cells were transformed by infection with human p110α (H1047R)-expressing avian retrovirus and are referred to as 10T1/2 tva-H1047R. A549 is a human lung cancer cell line expressing wild-type p110α. T47D and BT20 are human breast cancer cell lines expressing mutant p110α (T47D) and p110α (P539R/H1047R), respectively.

Figure 30:
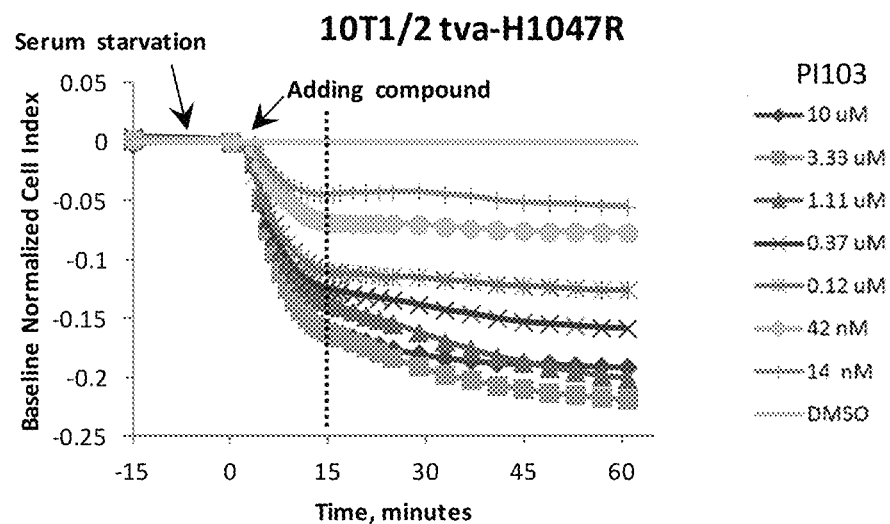
FIG. 30 shows the effect of PI3K inhibitor on the engineered mouse fibroblast cell line, 10T1/2 expressing human p110α (H1047R). Cells were serum starved for 5 hour. The cell index was normalized at time of compound addition. At the indicated time point of treatment, increasing concentrations of PI103 (0-10 uM) was added to the cells and the cell responses were monitored. (A) 10T1/2 tva-H1047R showed show sharp decreases (within 10 min of compound addition) in CI upon PI3K inhibition. Plotting the peak normalized CI responses versus the corresponding log concentration allows for calculation of the IC50 of PI103 for the mutant p110α
Figure 30:
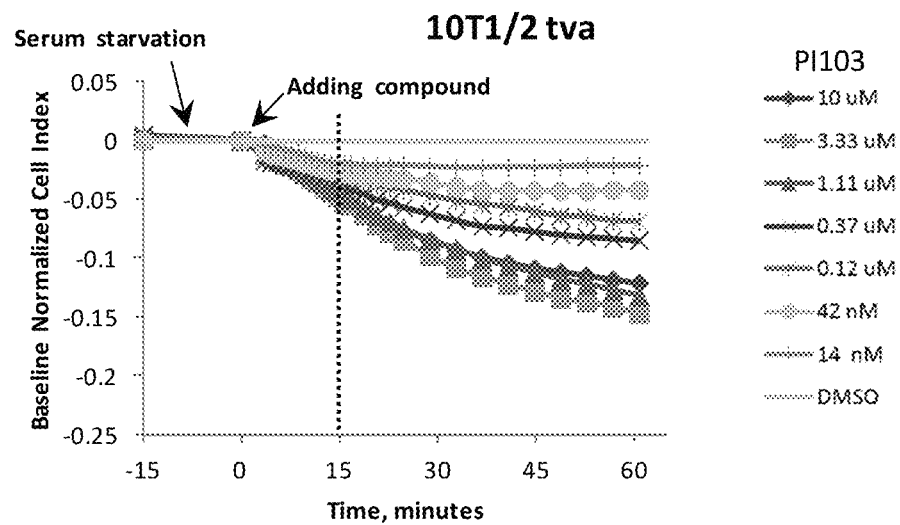

Both the control cells (10T1/2 tva) and PI3Kα mutant cells (10T1/2 tva-H1047R) were seeded into wells of 96 well E-plate devices (Roche) with an initial seeding density of 10,000 cells per well and were pre-incubated in incubator under standard cell culture condition for about 24 hours. Then the normal growth medium (10% FBS) was exchanged with medium containing 0% FBS. The cells were incubated for additional 5 hours before compound treatment. A PI3K inhibitor (PI103) at different concentrations in DMSO was added into wells following the incubation period. The cell status was monitored prior to and after the compound addition using xCelligence system (Roche applied sciences). FIG. 30 shows the baseline normalized cell index (normalized cell index with baseline subtraction) as a function of time prior to and after compound addition. Cell index of the cells treated with solvent DMSO control was used as baseline. The Cell index was normalized against the cell index values at a time point just before compound addition.

As shown in FIG. 30A, the cell index of 10T1/2 tva-H1047R was subjected to an immediate decrease upon PI103 treatment. The decrease in cell index reached a plateau 15 min after compound addition. The IC50 (89.0 nM) was calculated based on the dose response curves. In contrast, the control cell line (10T1/2 tva) did not show a clear dose response to PI103 treatment (FIG. 30B). Thus, the response profiles (impedance based TCRP) of 10T1/2 tva-H1047R to PI1-03 treatment as shown in FIG. 30A could be used as signature for the response of PI3Kα mutant cell lines to PI3K inhibitors.

To confirm the observed dose response was due to the oncogene p110α (H1047R), we checked whether knocking down this oncogene by siRNA would abolish the characteristic TCRP. First we verified that p110α (H1047R) protein expression level in 10T1/2 tva-H1047R upon siRNA knockdown led to more than 95% decrease in the p110α protein expression level (FIG. 34). Next, we tested the cell responses (TCRP) in 10T1/2 tva-H1047R treated with either control siRNA or siRNA specifically targeting human p110α. As shown in FIG. 31, control siRNA did not alter the characteristic TCRP in 10T1/2 tva-H1047R, whereas siRNA specifically targeting human p110α totally abolished the characteristic TCRP.

To test if the characteristic TCRP is specific to PI3K inhibition, we also test the cell responses in several other cell lines (FIG. 35). A549 expressing wild-type p110α did not show clear dose response to PI103 treatment. In contrast, T47D (p110α T47D) and BT20 (p110α P539R/H1047R), which express constitutively active PI3K, demonstrated the characteristic TCRP and a clear dose response to PI103 treatment. The calculated IC50 for T47D (p110α T47D) and BT20 (p110α P539R/H1047R) are 126 nM and 165 nM, respectively. These results indicate that this characteristic TCRP is likely a common phenomenon for all constitutively active PI3K mutant cell lines upon PI3K inhibition. Such characteristic TCRP could be used for identifying or screening unknown biologically active agents which may act as PI3K inhibitors.

To further confirm the specificity of the TCRP to PI3K inhibitor, we also tested the cell response to other control compounds in 10T1/2-tva-H1047R (FIG. 32) and 10T1/2-tva (FIG. 33). These inhibitors include PI3K/mTOR due kinase inhibitor (BEZ235), mTOR inhibitor (KU0063794 & Temsirolimus), pan-kinase inhibitor (Staurosporine), tubulin inhibitor (vincristine), PDGFR inhibitor (sorafenib), c-Raf1 inhibitor (GW5074), AKT1/2/3 inhibitor (AKT inhibitor VIII), EGFR inhibitor (lapatinib), p38 MAPK inhibitor (SB202190), JNK inhibitor (SP600125), MEK1/2 inhibitor (U0126), FLT3/JAK2/TrkA-C inhibitor (lestaurtinib), PKG inhibitor (KT5823), CaM kinase inhibitor (KN-62), EGFR inhibitor (erlotinib), MAPK/MEK inhibitor (PD98059) and PKA inhibitor (KT5720).

The mTOR inhibitor BEZ235, KU0063794 and Temsirolimus also triggered 10T1/2-tva-H1047R specific cell index drop, which was not present in the control cell line 10T1/2-tva. However, the kinetics of this drop is different from that triggered by PI3K inhibitor. Staurosporine, vincristine, sorafenib, GW5074, AKT inhibitor VIII, lapatinib and lestaurtinib led to cell index decreases in both the control cell line and H1047R cell line. This means that the CI drop induced by these inhibitors is not specific to PI3K. SB202190, SP600125, U0126, KT5823, CaM kinase inhibitor, erlotinib, PD98059 and KT5720 did not introduce significant cell index changes in either cell line. These results further validate that the observed TCRP induced by PI3K inhibitor is specific to the inhibition of p110α (H1047R) expressed in 10T1/2-tva-H1047R.

What is claimed is:

1. A method of designating a biologically active agent as a therapeutic that affects an oncogene addicted pathway within a cancer cell, the method comprising:
   a) providing a system for monitoring cell-substrate impedance comprising at least two impedance monitoring wells;
   b) culturing a population of cancer cells in each of the wells, wherein the cancer cells are primary cells or cells from a tumor;
   c) introducing a biologically active agent suspected of affecting an oncogene addicted pathway to a first well and a negative control to a second well, and introducing a stimulating agent that stimulates the oncogene addicted pathway to both wells;
   d) monitoring cell-substrate impedance of the two wells before and after adding the stimulating agent;
   e) generating an impedance-based curve for each of the two wells from the impedance values;
   f) comparing the impedance-based curves to determine a degree of similarity; and if significantly different,
   g) designating the biologically active agent as a therapeutic that affects the oncogene addicted pathway within the cancer cells.

2. The method of claim 1, wherein the cancer cells are selected from the group consisting of breast cancer cells, lung cancer cells, and colon cancer cells.

3. The method of claim 1, wherein the cancer cells are selected from the group consisting of gastric cancer cells, melanoma cells, and neuroblastoma cells.

4. The method of claim 1, wherein the biologically active agent is selected from the group consisting of Imatinib, Sorafinib, Sunitinib, Masitinib, BIBW2992 (Giotrif), WZ4002, Certinib, Lapatinib, Erlotinib, and Gefitinib.

5. The method of claim 4, wherein the biologically active agent is selected from the group consisting of Imatinib, Sorafinib, Sunitinib and Masitinib, further wherein the stimulating agent is platelet-derived growth factor (PDGF).

6. The method of claim 4, wherein the biologically active agent is selected from the group consisting of BIBW2992 (Giotrif), WZ4002, and Certinib, further wherein the stimulating agent is epidermal growth factor (EGF).

7. The method of claim 4, wherein the biologically active agent is selected from the group consisting of Lapatinib, Erlotinib, and Gefitinib, further wherein the stimulating agent is epidermal growth factor (EGF).

8. The method of claim 1, wherein the biologically active agent is added before the stimulating agent.

9. The method of claim 1, wherein the stimulating agent is a growth factor.

10. The method of claim 1, wherein the oncogene addicted pathway is selected from the group consisting of a cMET pathway, an EGFR pathway, a PDGFR pathway, an ALK pathway, a P13K pathway, a serine/threonine kinase pathway, and a b-Raf pathway.

11. The method of claim 1, wherein the monitored impedance measures cell adhesion to an electrode within one of the wells or cell morphology.

12. The method of claim 1, wherein the impedance-based curves are of cell indices determined from measured impedance values.

13. The method of claim 1, wherein the cancer cells are cultured in serum free media.

14. A method of designating a biologically active agent as a therapeutic that affects an oncogene addicted pathway within a cancer cell, the method comprising:
   a) providing a system for monitoring cell-substrate impedance comprising at least two impedance monitoring wells;
   b) culturing a population of cancer cells in each of the wells, wherein the cancer cells are primary cells or cells from a tumor;
   c) introducing a biologically active agent suspected of affecting an oncogene addicted pathway to a first well and a negative control to a second well, and introducing a stimulating agent that stimulates the oncogene addicted pathway to both wells;
   d) monitoring cell-substrate impedance of the two wells before and after adding the stimulating agent;
   e) generating a time-dependent cellular response profile (TCRP) from the monitored impedance for each of the two wells from the impedance values;
   f) comparing the TCRPs to determine a degree of similarity; and if significantly different,
   g) designating the biologically active agent as a therapeutic that affects the oncogene addicted pathway within the cancer cells.

15. The method according to claim 14, wherein the cancer cells are selected from the group consisting of breast cancer cells, lung cancer cells, and colon cancer cells.

16. The method according to claim 14, wherein the cancer cells are selected from the group consisting of gastric cancer cells, melanoma cells, and neuroblastoma cells.

17. The method of claim 14, wherein the biologically active agent is selected from the group consisting of Imatinib, Sorafinib, Sunitinib, Masitinib, BIBW2992 (Giotrif), WZ4002, Certinib, Lapatinib, Erlotinib, and Gefitinib.

18. The method of claim 17, wherein the biologically active agent is selected from the group consisting of Imatinib, Sorafinib, Sunitinib and Masitinib, further wherein the stimulating agent is platelet-derived growth factor (PDGF).

19. The method of claim 17, wherein the biologically active agent is selected from the group consisting of BIBW2992 (Giotrif), WZ4002, and Certinib, further wherein the stimulating agent is epidermal growth factor (EGF).

20. The method of claim 17, wherein the biologically active agent is selected from the group consisting of Lapatinib, Erlotinib, and Gefitinib, further wherein the stimulating agent is epidermal growth factor (EGF).

* * * * *